(12) United States Patent
Clemmer et al.

(10) Patent No.: US 8,618,475 B2
(45) Date of Patent: Dec. 31, 2013

(54) ION MOBILITY SPECTROMETER WITH ONE OR MORE INTEGRAL ION ACTIVATION REGIONS

(75) Inventors: David E. Clemmer, Bloomington, IN (US); Stormy L. Koeniger, Evanston, IL (US); Stephen J. Valentine, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 183 days.

(21) Appl. No.: 13/038,544

(22) Filed: Mar. 2, 2011

(65) Prior Publication Data
US 2011/0198493 A1 Aug. 18, 2011

Related U.S. Application Data

(62) Division of application No. 11/286,608, filed on Nov. 23, 2005.

(51) Int. Cl.
*H01J 49/40* (2006.01)
(52) U.S. Cl.
USPC .............................. 250/287; 250/282; 250/286
(58) Field of Classification Search
USPC .............................................................. 250/287
See application file for complete search history.

(56) References Cited

U.S. PATENT DOCUMENTS

| | | | |
|---|---|---|---|
| 3,668,383 A | 6/1972 | Carroll | |
| 5,095,206 A | 3/1992 | Bacon, Jr. et al. | |
| 5,162,649 A * | 11/1992 | Burke | 250/287 |
| 6,323,482 B1 | 11/2001 | Clemmer et al. | |
| 6,744,043 B2 | 6/2004 | Loboda | |
| 6,818,890 B1 | 11/2004 | Smith et al. | |
| 6,967,325 B2 | 11/2005 | Smith et al. | |
| 7,170,053 B2 * | 1/2007 | Shvartsburg et al. | 250/287 |
| 7,227,134 B2 | 6/2007 | Miller et al. | |
| 7,388,195 B2 * | 6/2008 | Zapata et al. | 250/288 |
| 2002/0185606 A1 | 12/2002 | Smith et al. | |

FOREIGN PATENT DOCUMENTS

| | | |
|---|---|---|
| EP | 1646068 A2 | 4/2006 |
| JP | 2006-107929 A | 4/2008 |
| JP | 2005-524196 A | 8/2008 |
| WO | 2005-043115 A2 | 5/2005 |
| WO | 2005-052546 A2 | 6/2005 |
| WO | 2007-062303 A2 | 5/2007 |

OTHER PUBLICATIONS

Structural information from ion mobility measurements: applications to semiconductor clusters; Chem. Soc. Rev. v. 30, pp. 26-35, 2001.*

(Continued)

*Primary Examiner* — Phillip A Johnston
(74) *Attorney, Agent, or Firm* — Barnes & Thornburg LLP

(57) ABSTRACT

An ion mobility spectrometer comprises a drift tube defining a drift tube inlet configured to receive ions and a drift tube outlet. The drift tube is configured to separate ions in time as a function of ion mobility. The drift tube defines a first ion activation region between the drift tube inlet and the drift tube outlet. The first ion activation region is configured to selectively induce structural changes in at least some of the ions.

26 Claims, 22 Drawing Sheets

(56) References Cited

OTHER PUBLICATIONS

Badman, E. R. at al., Dissociation of Different Conformations of Ubiquitin Ions, J. Am. Soc. of Mass Spectrom 2002, 13, pp. 719-723.
Badman, Ethan R., et al. Gas-Phase Separations of Protein and Peptide Ion Fragments Generated by Collision-Induced Dissociation in an Ion Trap, Oct. 1, 2002, vol. 74, No. 19, pp. 4889-4894.
Barran, P. E., et al., Is it Biologically Relevant to Measure the Structures of Small Peptides in the Gas-Phase?, Int. J. Mass Spectrom. 2005, 240, pp. 273-284.
Breuker, K. at al., Detailed Unfolding and Folding of Gaseous Ubiquitin Ions Characterized by Electron Capture Dissociation, J. Am. Chem. Soc 2002, 124, pp. 6407-6420.
Clauser, K R. et al., Role of Accurate Mass Measurement (±10 ppm) in Protein identification strategies Employing MS or MS/MS and Database Searching, Anal. Chem. 1999, 71, pp. 2871-2882.
Clemmer, D. E. et al., Naked Protein Conformations: Cytochrome c in the Gas Phase, J. Am. Chem. Soc. 1995, 117, pp. 10141-10142.
Clowers, B. H. et al., Separation of Sodiated Isobaric Disaccharides and Trisaccharides Using Electrospray Ionization-Atmospheric Pressure Ion Mobility-Time of Flight-Mass Spectrometry, J. Am Soc Mass Spectrom, 2005, 16, pp. 660-669.
Collins, D.C. et al., Developments in Ion Mobility Spectrometry-Mass Spectrometry, Anal. Bioanal. Chem. 2002, 372, pp. 66-73.
Counterman, A. E. at al., Cis-Trans Signatures of Proline-Containing Tryptic Peptides in the Gas Phase, Anal. Chem. 2002, 74, pp. 1946-1951.
Counterman, A.E. et al., High-Order Structure and Dissociation of Gaseous Peptide Aggregates that are Hidden in Mass Spectra, J. Am. Soc. Mass Spectrom, 1998, 9, pp. 743-759.
Covey, T., et al., Collision Cross Sections for Protein Ions, J. Am. Soc. Mass Spectrom, 1993, 4, pp. 616-623.
Creaser, C. S. et al., Ion Mobility Spectrometry: a review. Part 1. Structural analysis by mobility measurement, Analyst 2004, 129, pp. 984-994.
European Supplementary Search Report dated Sep. 24, 2010 for related European Patent Application No. 06839885.8 (10 pages).
Freitas, M. A. et al., Rate and Extent of Gas-Phase Hydrogen/Deuterium Exchange of Bradykinins: Evidence for Peptide Zwitterions in the Gas Phase, Int. J. Mass Spectrom. 1999, 183, pp. 221-231.
Geller, O. et al., A Fast Flow Tube Study of Gas Phase H/D Exchange of Multiply Protonated Ubiquitin, J. Phys. Chem. A 2005, 109, pp. 2217-2222.
Gill, A. C. et al., Conformations of Biopolymers in the Gas Phase: a New Mass Spectrometric Method, Int. J. Mass Spectrom 2000, 195, pp. 685-697.
Gillig, K. J. et al., Coupling High-Pressure MALDI with Ion Mobility/Orthogonal Time-of-Flight Mass Spectrometry, Anal. Chem. 2000, 72, pp. 3965-3971.
Gimon-Kinsel, M.E. et al., Conformations of Protonated Gas-Phase Bradykinin Ions: Evidence for Intramolecular Hydrogen Bonding, J. Mass Spectrom. 1999, 34, pp. 124-136.
Henderson. S. C. et al., ESI/Ion Trap/Ion Mobilily/Time-of-Flight Mass Spectrometry for Rapid and Sensitive Analysis of Biomolecular Mixtures, Anal. Chem 1999, 71, 291-301.
Hoaglund, C. S. et al., An Ion Trap Interface for ESI-Ion Mobility Experiments, Anal. Chem. 1997, 69, pp. 4156-4161.
Hoaglund, Cherokee S., et al., Three-Dimensional Ion Mobility/TOFMS Analysis of Electrosprayed Biomolecules, Analytical Chemistry, Jun. 1, 1998, vol. 70, No. 11, pp. 2236-2242.
Hoaglund-Hyzer C S et al: "Coupling Ion Mobility Separations, Collisional Activation Techniques, and Multiple Stages of MS for Analysis of Complex Peptide Mixtures." Analytical Chemistry, American Chemical Society, US LNKD—DOI:10.1021/Ac010837s vol. 74, No. 5, Feb. 2, 2002, pp. 992-1006, XP002371949.
Hoaglund-Hyzer, Cherokee S. et al., Mobility Labeling for Parallel CID of Ion Mixtures, Analytical Chemistry, Jul. 1, 2000, vol. 72, No. 13, pp. 2737-2740.

Jackson, S.N. et al., Direct Tissue Analysis of Phospholipids in Rat Brain Using MALDI-TOFMS and MALDI-Ion Mobility-TOFMS, J. Am. Soc. Mass Spectrom. 2005, 16, pp. 133-138.
Jarrold, M. F., Peptides and Proteins in the Vapor Phase, Annu. Rev. Phys. Chem 2000, 51, pp. 179-207.
Jarrold, M.F. et al., Silicon Cluster Ions: Evidence for a Structural Transition, Phys. Rev. Lett. 1991, 67, pp. 2994-2997.
Karas, M. et al., Laser Desorption Ionization of Proteins with Molecular Masses Exceeding 10 000 Daltons, Anal. Chem. 1988, 60, pp. 2299-2301.
Karas, M. et al., Matrix-Assisted Ultraviolet Laser Desorption of Non-Volatile Compounds, J. Mass Spectrom. Ion Processes 1987, 78, pp. 53-68.
Kim, S.H. et al., Ion Mobility Spectrometry/Mass Spectrometry of Two Structurally Different Ions Having Identical Ion Mass, Anal. Chem. 1985, 57, pp. 567-569.
Kim, T et al., Design and Implementation of a New Electrodynamic Ion Funnel, Anal. Chem. 2000, 72, pp. 2247-2255.
Koeniger, S. L. et al., Development of Field Modulation in a Split-Field Drift Tube for High-Throughput Multidimensional Separations, J. of Proteome Research 2005, 4, pp. 25-35.
Li, J. et al., Coupling Capillary Electrophoresis and High-Field Asymmetric Waveform Ion Mobility Spectrometry Mass Spectrometry for the Analysis of Complex Lipopolysaccharides, Anal. Chem. 2004; 76, pp. 4676-4683.
Li, J. et al., Influence of Solvent Composition and Capillary Temperature on the Conformations of Electrosprayed Ions: Unfolding of Compact Ubiquitin conformers from Pseudonative and Denatured Solutions, Int. J. Mass Spectrom. 1999, 187, pp. 37-47.
Lifshitz, C., A Review of Gas-Phase H/D Exchange Experiments: The Protonated Arginine Dimer and Bradykinin Nonapeptide Systems, Int. J. Mass Spectrom. 2004, 234, pp. 63-70.
Liu X. et al., Development of High Throughput Dispersive LC-Ion Mobility-TOFMS Techniques for Analysing the Human Plasma Proteome, Briefings of Funct. Genomics & Proteomics 2004, 3, pp. 177-186.
Liu, Yansheng, et al., Analytical Chemistry, Jul. 1, 1997, vol. 69, No. 13, pp. 2504-2509.
Mao, D. et al., H/D Exchange of Gas Phase Bradykinin Ions in a Linear Quadrupole Ion Trap, J. Am. Soc. Mass Spectrom. 2003, 14, pp. 85-94.
Mesleh, M. F. et al., Structural Information from Ion Mobility Measurements: Effects of the Long-Range Potential, J. Phys. Chem. 1996, 100, pp. 16082-16086.
Moon M. H. et al., Nanoflow LC/Ion Mobility/CID/TOF for Proteomics: Analysis of a Human Urinary Proteome, J. of Proteome Research 2003, 2, pp. 589-597.
Myung, S. et al. Development of High-Sensitivity Ion Trap Ion Mobility Spectrometry Time-of-Flight Techniques: A High-Throughput Nano-LC-IMS-TOF Separation of Peptides Arising from a Drosophila Protein Extract, Anal. Chem. 2003, 75, pp. 5137-5145.
Myung, S. et al., Structural Transitions of Electrosprayed Ubiquitin Ions Stored in an Ion Trap Over~10 ms to 30 St, J. Phys. Chem. A 2002, 106, pp. 9976-9982.
Ochoa, M. L. et al., Chemometric Studies for the Characterization and Differentiation of Microorganisms Using in Situ Derivatization and Thermal Desorption Ion Mobility Spectrometry. Anal. Chem. 2005, 77, pp. 854-863.
PCT Search Report Apr. 29, 2008 cited in PCT/US 06/60902 (2 pages).
PCT Written Opinion Apr. 29, 2008 cited in PCT/US 06/60902 (9 pages).
Purves, R W. at al. Separation of Protein Conformers Using Electrospray-High Field Asymmetric Waveform Ion Mobility Spectrometry-Mass Spectrometry, Int. J. Mass Spectrom, 2000, 197, pp. 163-177.
Purves, R.W. et al., Gas-Phase Conformers of the [M + 2H] 2+ ion of Bradykinin Investigated by Combining High-Field Asymmetric Waveform Ion Mobility Spectrometry, Hydrogen/Deuterium Exchange, and Energy-Loss Measurements, Rapid Commun. Mass Spectrom. 2001, 15, pp. 1453-1456.

(56) References Cited

OTHER PUBLICATIONS

Qian, M. G. et al., A Marriage Made is MS, Anal. Chem. 1995, 67, pp. 234-242.

Reid, G. E. et al., Charge-State-Dependent Sequence Analysis of Protonated Ubiquitin Ions via Ion Trap Tandem Mass Spectrometry, Anal. Cham. 2001, 73, pp. 3274-3281.

Schneider, B. B. et al., Collision-Induced Dissociation of Bradykinin Ions in the Interface Region of an ESI-MS. J. Am. Soc. Mass Spectrom. 2001, 12, pp. 772-779.

Schnier, P.D. et al., Blackbody Infrared Radiative Dissociation of Bradykinin and Its Analogues: Energetics, Dynamics, and Evidence for Salt-Bridge Structures in the Gas Phase, J. Am. Chem. Soc. 1996, 118, pp. 7178-7189.

Shaffer, S. A. el al., Characterization of an Improved Electrodynamic Ion Funnel Interface for Electrospray Ionization Mass Spectrometry, Anal. Chem. 1999, 71, pp. 2957-2964.

Shaffer, S. A. et al., An Ion Funnel Interface for Improved Ion Focusing and Sensitivity Using Electrospray Ionization Mass Spectrometry, Anal. Chem. 1998, 70, pp. 4111-4119.

Shaffer. S. A. et al., Novel Ion Funnel for Focusing Ions at Elevated Pressure Using Electrospray Ionization Mass Spectrometry, Rapid Commun. Mass Spectrom. 1997, 11, pp. 1813-1817.

Shelimov, K. B. et al., Conformations, Unfolding, and Refolding of Apomyoglobin in Vacuum: An Activation Barrier for Gas-Phase Protein Folding, J. Am. Chem. Soc. 1997, 119, pp. 2987-2994.

Shelimov, K. B. et al., Protein Structure in Vacuo: Gas-Phase Conformations of BPTI and Cytochrome c, J. Am. Chem. 1997, 119, pp. 2240-2248.

Shvartsburg, A. A, et al., An Exact Hard-Spheres Scattering Model for the Mobilities of Polyatomic Ions, Chem. Phys. Lett. 1996, 261, pp. 86-91.

Snyder A. P. et al., Correlation of Mass Spectrometry Identified Bacterial Biomarkers from a Fielded Pyrolysis-Gas Chromatography-Ion Mobility Spectrometry Biodetector with the Microbiological Gram Stain Classification Scheme, Anal. Chem. 2004, 76, pp. 6492-6499.

Stone, E. et al., Surface-Induced Dissociation on a MALDI-Ion Mobility-Orthogonal Time-of-Flight Mass Spectrometer: Sequencing Peptides from an "In-Solution" Protein Digest. Anal. Chem. 2001, 73, pp. 2233-2238.

Suckau, D. et al., Coexisting Stable Conformations of Gaseous Protein Ions, Proc, Natl. Acad. Sci. USA 1993, 90, pp. 790-793.

Tang, Keqi et al., High-Sensitivity Ion Mobility Spectrometry/Mass Spectrometry Using Electrodynamic Ion Funnel Interfaces, Analytical Chemistry, May 15, 2005, vol. 77, No. 10, pp. 3330-3339.

Taylor, J. A. et al., Sequence Database Searches Via de Novo Peptide Sequencing by Tandem Mass Spectrometry, Rapid Commun. Mass Spectrom. 1997, 11, pp. 1067-1075.

Thalassinos, K. et al., Ion Mobility Mass Spectrometry of Proteins in a Modified Commercial Mass Spectrometer, Int. J. Mass Spectrom, 2004, 236, pp. 55-63.

Valentine, S. J. at al., A Database of 660 Peptide Ion Cross Sections: Use of Intrinsic Size Parameters for Bona Fide Predictions of Cross Sections, J. Am. Soc. Mass Spectrom. 1999, 10, pp. 1188-1211.

Valentine, S. J. et al., Conformer-Dependent Proton-Transfer Reactions of Ubiquitin Ions, J. Am. Soc. Mass Spectrom. 1997, 8, pp. 954-961.

Valentine, S. J. et al., Disulfide-Intact and -Reduced Lysozyme in the Gas Phase: Conformations and Pathways of Folding and Unfolding, J. Phys. Chem. B. 1997, 101, pp. 3891-3900.

Valentine, S. J. et al., Multidimensional Separations of Complex Peptide Mixtures: a Combined High-Performance Liquid Chromatography/Ion Mobility/Time-of-Flight Mass Spectrometry Approach, Int. J. Mass Spectrom. 2001, 212, pp. 97-109.

Valentine, S. J. et at., H/D Exchange Levels of Shape-Resolved Cytochrome c Conformers in the Gas Phase, J. Am. Chem. Soc, 1997, 119, pp. 3558-3566.

Valentine, Stephen J., et al., A Split-Field Drift Tube for Separation and Efficient Fragmentation of Biomolecular Ions, Analytical Chemistry, Nov. 15, 2003, vol. 75, No. 22, pp. 6202-6208.

Venne, K. et al., Improvement in Peptide Detection for Proteomics Analyses Using NanoLC-MS and High-Field Asymmetry Waveform Ion Mobility Mass Spectrometry, Anal. Chem. 2005, 77, pp. 2176-2186.

Von Helden, G. et al., M.T. Science 1993, 259, pp. 1230-1231.

Woenckhaus. J. at al., Hydration of Gas Phase Proteins: Folded +5 and Unfolded +7 Charge States of Cytochrome c, J. Phys. Chem. B. 1997, 101, pp. 847-851.

Wu, C. et al., Electrospray Ionization High-Resolution Ion Mobility Spectrometry-Mass Spectrometry, Anal. Chem. 1998, 70, pp. 4929-4938.

Wyttenbach, T. et al., Design of a New Electrospray Ion Mobility Mass Spectrometer, Int. J. Mass Spectrom 2001, 212, pp. 13-23.

Wyttenbach, T. et al., Effect of the Long-Range Potential on Ion Mobility Measurements, J. Am. Soc. Mass Spectrom. 1997, 8, pp. 275-282.

Wyttenbach, Thomas, et al., Design of a New Electrospray Ion Mobility Mass Spectrometer, International Journal of Mass Spectrometry 212 Jul. 14, 2001, 13-23 (11 pages).

Wyttenbach. T. et al., Gas-Phase Conformation of Biological Molecules: Bradykinin, J. Am. Chem. Soc 1996, 118, pp. 8355-8364.

Young, C.E. et al, Water Cluster Ions: Rates of Formation and Decomposition of Hydrates of the Hydronium Ion, J. Chem. Phys. 1970, 53, pp. 4295-4302.

English Translation of counterpart Japanese Office Action for JP Application No. 2008-542497, received May 16, 2012 (4 pages).

* cited by examiner

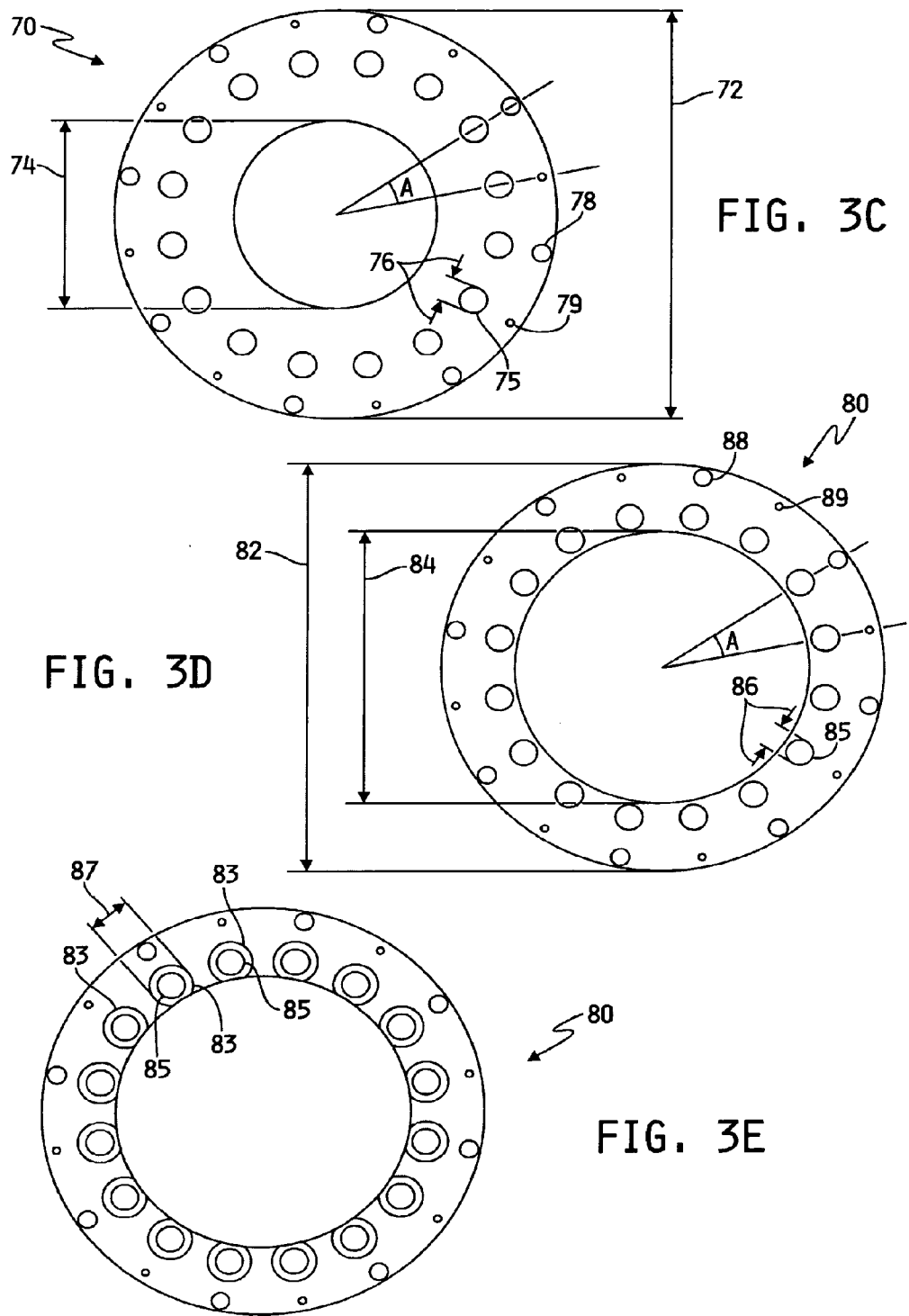

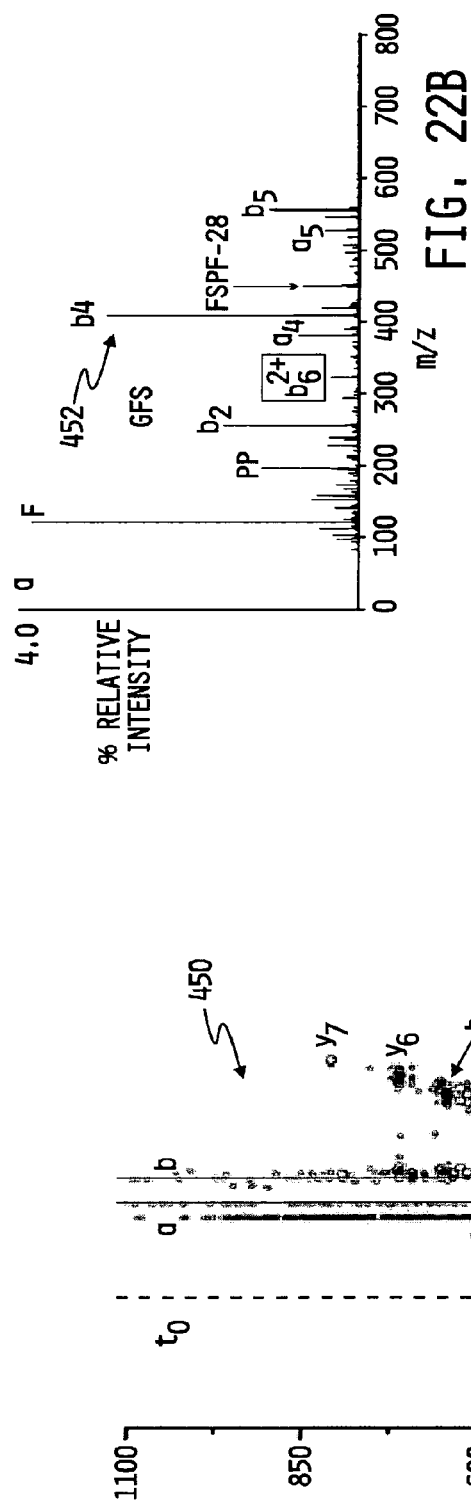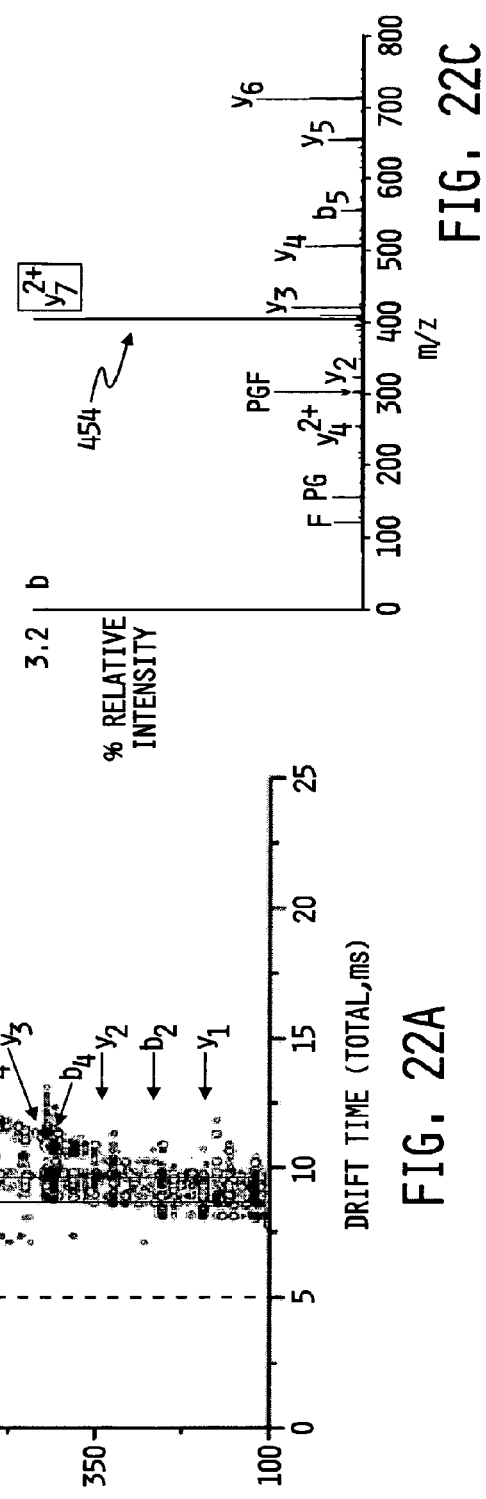

ION MOBILITY SPECTROMETER WITH ONE OR MORE INTEGRAL ION ACTIVATION REGIONS

CROSS-REFERENCE TO RELATED U.S. APPLICATION

This is a divisional of U.S. patent application Ser. No. 11/286,608, filed Nov. 23, 2005, and entitled ION MOBILITY SPECTROMETER, the disclosure of which is incorporated herein by reference.

This invention was made with government support under AG024547 awarded by the National Institutes of Health and under CHE-0078737 awarded by the National Science Foundation. The U.S. Government has certain rights in the invention.

FIELD OF THE INVENTION

The present invention relates generally to the field of spectrometry, and more specifically to instruments for separating ions in time as a function of ion mobility.

BACKGROUND

Ion mobility spectrometers are analytical instruments that are used to investigate properties of charged particles. Generally, ion mobility spectrometers separate ions in time as a function of ion mobility. It is desirable with such instruments to investigate properties of charged particles produced from a variety of sources including, for example, but not limited to, complex biological samples.

SUMMARY

The present invention may comprise one or more of the features recited in the attached claims, and/or one or more of the following features and combinations thereof. An ion mobility spectrometer may comprise a drift tube defining a drift tube inlet configured to receive ions and a drift tube outlet. The drift tube may be configured to separate ions in time as a function of ion mobility. The drift tube may define a first ion activation region between the drift tube inlet and the drift tube outlet. The first ion activation region may be configured to selectively induce structural changes in at least some of the ions.

The ion mobility spectrometer may further comprise a source of buffer gas. The drift tube may be configured to receive buffer gas therein from the source of buffer gas. The ion mobility spectrometer may further include at least one voltage source coupled to the first ion activation region. The at least one voltage source may be configured to selectively establish an electric field in the first ion activation region that is sufficient to induce structural changes in the at least some of the ions by fragmenting the at least some of the ions via collisions with the buffer gas. Alternatively, the at least one voltage source may be configured to selectively establish an electric field in the first ion activation region that is sufficient to induce structural changes in the at least some of the ions by inducing conformational changes in the at least some of the ions via collisions with the buffer gas without fragmenting the at least some of the ions.

The ion mobility spectrometer may further comprise an ion source region configured to supply ions to the drift tube inlet. The ion mobility spectrometer may further include an ion gate normally impeding passage of ions from the ion source region into the drift tube inlet. The ion gate may be responsive to an ion gate control signal to allow passage of ions from the ion source region into the drift tube inlet. The ion source region may define a funnel therein. The funnel may have one end defining a first opening with a first cross-sectional area and an opposite end defining a second opening with a second cross-sectional area smaller than the first cross-sectional area. The funnel may be configured to receive ions in the first opening and to supply ions to the drift tube inlet via the second opening. The funnel may define a cavity between the first and second openings configured to radially focus ions between the first and second openings. The ion mobility spectrometer may further include a voltage source coupled to the funnel. The voltage source may be configured to selectively create a second ion activation region within the funnel. The second ion activation region within the funnel may be configured to induce structural changes in at least some of the ions within the funnel. The ion mobility spectrometer may further include an ion gate positioned between the second opening of the funnel and the drift tube inlet. The ion gate may normally impeding passage of ions from the funnel into the drift tube inlet. The ion gate may be responsive to an ion gate control signal to allow passage of ions from the funnel into the drift tube inlet. The ion mobility spectrometer may further include a voltage source coupled to the funnel. The funnel may be responsive to voltage produced by the voltage source to collect therein ions received via the first opening. The ion gate may be responsive to the ion gate control signal to allow passage of at least some of the ions collected in the funnel into the drift tube inlet. The ion source region may be configured to receive ions generated externally thereto. Alternatively or additionally, the ion source region may be configured to generate ions from a sample source.

The ion mobility spectrometer may further comprise an ion gate positioned between the drift tube inlet and the drift tube outlet and partitioning the drift tube into a first drift tube region between the drift tube inlet and the ion gate and a second drift tube region between the ion gate and the drift tube outlet. The ion gate may be responsive to a first control signal to impede passage of ions from the first drift tube region into the second drift tube region and to a second control signal to allow passage of ions from the first drift tube region into the second drift tube region. The ion mobility spectrometer may further comprise a voltage source configured to produce the first and second control signals. The voltage source may be programmable to produce the second control signal at a predetermined time relative to passage of ions into the first drift tube region to thereby allow passage into the second drift tube region only of ions having a corresponding predetermined mobility range. The drift tube may define a funnel therein between the drift tube inlet and the drift tube outlet. The funnel may have one end defining a first opening with a first cross-sectional area and an opposite end defining a second opening with a second cross-sectional area smaller than the first cross-sectional area. The funnel may be configured to receive ions in the first opening and to supply ions via the second opening. The funnel may define a cavity between the first and second openings configured to radially focus ions between the first and second openings. The first opening of the funnel may be positioned adjacent to the ion gate with the ion gate disposed between the first drift tube region and the first opening of the funnel and with the second drift tube region extending between the second end of the funnel and the drift tube outlet. The ion activation region may be positioned between the second end of the funnel and the second drift tube region.

The ion mobility spectrometer may further comprise a third ion activation region positioned adjacent to the drift tube outlet. The third ion activation region may be configured to selectively induce structural changes in at least some of the ions exiting the drift tube outlet. The ion mobility spectrometer may further comprise a source of buffer gas. The drift tube may be configured to receive buffer gas therein from the source of buffer gas. The ion mobility spectrometer may further comprise at least one voltage source coupled to the third ion activation region and configured to selectively establish an electric field in the third ion activation region sufficient to induce structural changes in the at least some of the ions exiting the drift tube outlet by fragmenting the at least some of the ions exiting the drift tube outlet via collisions with the buffer gas. Alternatively, the at least one voltage source may be configured to selectively establish an electric field in the third ion activation region sufficient to induce structural changes in the at least some of the ions exiting the drift tube outlet by inducing conformational changes in the at least some of the ions exiting the drift tube outlet via collisions with the buffer gas without fragmenting the at least some of the ions exiting the drift tube outlet.

The ion mobility spectrometer may further comprise an ion detector positioned to detect ions exiting the drift tube outlet and produce electrical signals indicative thereof. The ion mobility spectrometer may further comprise a processor electrically coupled to the ion detector. The processor may be configured to process the electrical signals produced by the ion detector to determine corresponding ion mobility spectral information.

The ion mobility spectrometer may further comprise an ion mass spectrometer positioned to receive ions exiting the drift tube outlet. The ion mass spectrometer may be configured to separate in time as a function of ion mass-to-charge ratio at least some of the ions exiting the drift tube outlet. The ion mobility spectrometer may further comprise an ion detector positioned to detect ions exiting the ion mass spectrometer and produce electrical signals indicative thereof. The ion mobility spectrometer may further comprise a processor electrically coupled to the ion detector. The processor may be configured to process the electrical signals produced by the ion detector to determine ion spectral information as a function of ion mobility and of ion mass-to-charge ratio.

An ion mobility spectrometer may comprise an ion source configured to produce ions, and a drift tube defining a drift tube inlet configured to receive ions from the ion source and a drift tube outlet. The drift tube may include an ion gate positioned between the drift tube inlet and the drift tube outlet and partitioning the drift tube into a first drift tube region between the drift tube inlet and the ion gate and a second drift tube region between the ion gate and the drift tube outlet. The ion gate may be responsive to a first control signal to impede passage of ions from the first drift tube region into the second drift tube region and to a second control signal to allow passage of ions from the first drift tube region into the second drift tube region. The drift tube may be configured to separate ions in time as a function of ion mobility between the drift tube inlet and the ion gate and also between the gate and the drift tube outlet. The drift tube may define an ion activation region configured to selectively induce structural changes in at least some of the ions exiting the first drift tube region.

The ion mobility spectrometer may further comprise a source of buffer gas. The drift tube may be configured to receive buffer gas therein from the source of buffer gas. The ion mobility spectrometer may further include at least one voltage source coupled to the ion activation region. The at least one voltage source may be configured to selectively establish an electric field in the ion activation region sufficient to induce structural changes in the at least some of the ions exiting the first drift tube region by fragmenting the at least some of the ions exiting the first drift tube region via collisions with the buffer gas. Alternatively, the at least one voltage source may be configured to selectively establish an electric field in the ion activation region sufficient to induce structural changes in the at least some of the ions exiting the first drift tube region by inducing conformational changes in the at least some of the ions exiting the first drift tube region via collisions with the buffer gas without fragmenting the at least some of the ions exiting the first drift tube region. The ion source may include a protein solution. The ion source may be configured to produce protein ions from the protein solution. The ion mobility spectrometer may further include an ion detector positioned to detect ions exiting the drift tube outlet. The ion activation region may be positioned adjacent to the gate with the ion activation region disposed between the gate and the drift tube outlet.

A method of separating ions in time as a function of ion mobility may comprise introducing ions into a first drift tube, separating the ions in time as a function of ion mobility in the first drift tube, inducing structural changes in at least some of the ions exiting the first drift tube, and separating in time the ions exiting the first drift tube, after inducing structural changes in at least some of the ions exiting the first drift tube, as a function of ion mobility in a second drift tube.

The act of inducing structural changes in at least some of the ions exiting the first drift tube may comprise exposing the ions exiting the first drift tube to an electric field in the presence of a buffer gas, the electric field sufficient to fragment the at least some of the ions via collisions with the buffer gas. Alternatively the act of inducing structural changes in at least some of the ions exiting the first drift tube may comprise exposing the ions exiting the first drift tube to an electric field in the presence of a buffer gas, the electric field sufficient to induce conformational changes in the at least some of the ions via collisions with the buffer gas without fragmenting the at least some of the ions.

The method may further comprise allowing only ions having a predefined ion mobility range to exit the first drift tube region.

The method may further comprise inducing structural changes in at least some of the ions prior to introducing the ions into the drift tube.

The method may further comprise separating in time as a function of ion mass-to-charge ratio at least some of the ions exiting the second drift tube.

The method may further comprise inducing structural changes in at least some of the ions exiting the second drift tube. The method may further comprise separating in time ions exiting the second drift tube, after inducing structural changes in at least some of the ions exiting the second drift tube, as a function of ion mass-to-charge ratio.

The first drift tube may comprise a first region of a single drift tube and the second drift tube comprises a second region of the single drift tube. The act of inducing structural changes in at least some of the ions exiting the first drift tube may be carried out in an ion activation region of the single drift tube that is positioned between the first and second drift tube regions.

The method may further include radially focusing the ions exiting the first drift tube in a funnel structure prior to inducing structural changes in at least some of the ions exiting the first drift tube.

The method may further include radially focusing the ions in a funnel structure prior to introducing the ions into the first drift tube.

The method may further include radially focusing ions in the second drift tube in a funnel structure prior to exiting the second drift tube.

An ion mobility spectrometer may comprise a drift tube defining a drift tube inlet configured to receive ions and a drift tube outlet, an ion fragmentation region, a source of buffer gas configured to supply buffer gas to at least the ion fragmentation region, a source of doping gas configured to supply pressurized doping gas to at least the ion fragmentation region and at least one voltage source coupled to the ion fragmentation region. The drift tube may be configured to separate the ions in time as a function of ion mobility. The at least one voltage source may be configured to selectively establish an electric field in the ion fragmentation region that is sufficient to fragment at least some of the ions via collisions with a mixture of the buffer gas and the doping gas. The doping gas may be selected such that a magnitude of the electric field that can be sustained in the ion fragmentation without breaking down in the presence of the ions and the mixture of the buffer gas and the doping gas is higher than the magnitude of the electric field that can be sustained in the ion fragmentation region without breaking down in the presence of ions and only the buffer gas.

The ion fragmentation region may be contained within the drift tube. Alternatively, the ion fragmentation region may be positioned adjacent to the drift tube outlet.

The ion mobility spectrometer may further include an ion source configured to supply ions to the drift tube inlet. The ion fragmentation region may be positioned to fragment at least some of the ions prior to entrance into the drift tube.

The buffer gas may be helium. The doping gas may be nitrogen.

The mixture of the buffer gas and the doping gas may consist of approximately 1-5 mole percent of the nitrogen gas and approximately 95-99 mole percent of the helium gas.

A method of increasing the magnitude of an electric field that can be sustained without breaking down in the presence of ions and a buffer gas may comprise selecting a doping gas to mix with the buffer gas to form a mixture gas such that a magnitude of an electric field that can be sustained without breaking down in the presence of ions and the mixture gas is higher than the magnitude of the electric field that can be sustained without breaking down in the presence of ions and the buffer gas, and mixing the doping gas with the buffer gas to form the mixture gas. The buffer gas may be helium. The doping gas may be nitrogen. The mixture gas may consist of approximately 1-5 mole percent of the nitrogen gas and approximately 95-99 mole percent of the helium gas.

BRIEF DESCRIPTION OF THE DRAWINGS

FIG. 3C is a front elevational view of an electrically conductive end ring member used in the construction of the drift tube section of FIG. 2.

FIG. 3D is a rear elevational view of an electrically conductive end plate member used in the construction of the drift tube section of FIG. 2.

FIG. 3E is a front elevational view of the electrically conductive end plate member of FIG. 3D.

FIG. 22A is a plot of drift time vs. mass-to-charge ratio illustrating an example distribution of 1° and 2° fragments generated from a distribution of ions that were mobility selected by pulsing G2 at time $t_0$.

FIG. 22B is a plot of mass-to-charge ratio vs. relative intensity of 2° fragments resulting from dissociation of $b_6^{2+}$ 1° fragment precursor ions of the distribution of FIG. 22A.

FIG. 22C is a plot of mass-to-charge ratio vs. relative intensity of 2° fragments resulting from dissociation of $y_7^{2+}$ 1° fragment precursor ions of the distribution of FIG. 22A.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
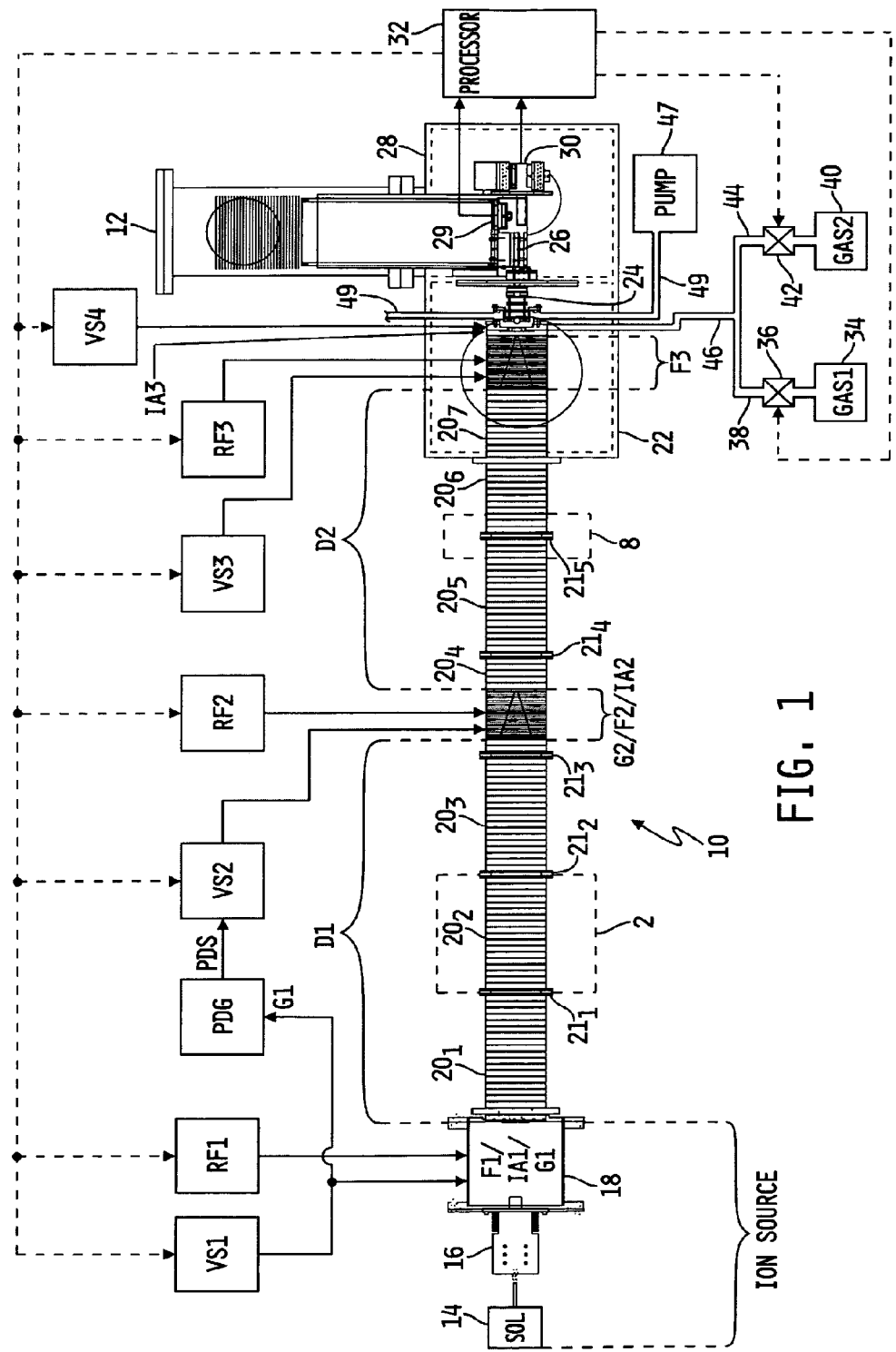
FIG. 1 is a diagram of one illustrative embodiment of an ion mobility spectrometer operatively coupled to a mass spectrometer.

Referring now to FIG. 1, one illustrative embodiment of an ion mobility spectrometer (IMS) 10 is shown. In the illustrated embodiment, the IMS 10 is shown coupled to a mass spectrometer 12 such that an ion outlet of the IMS 10 supplies ions to an ion acceleration region of the mass spectrometer 12. The IMS 10 includes an ion source coupled to a drift tube structure, and is operable, as will be described in greater detail hereinafter, to separate in time ions received from the ion source region as a function of ion mobility, and the mass spectrometer 12 is operable in a conventional manner to separate in time ions received from the IMS 10 as a function of ion mass-to-charge ratio. The result is a two-dimensional spectrum of molecular information; one in ion mobility and the other in ion mass-to-charge ratio. The mass spectrometer 12 may be conventional in its construction and may be provided in any of a variety of conventional forms including, for example, but not limited to, a linear time-of-flight (TOF) mass spectrometer, a reflectron time-of-flight mass spectrometer, a Fourier Transform Ion Cyclotron Resonance (FTICR) mass spectrometer, or other conventional ion mass spectrometer or analyzer. It will be understood, however, that the ion mobility spectrometer 10 need not be coupled to the mass spectrometer 12, and may instead be operable on its own to produce one-dimensional information relating only to ion mobility. One embodiment of such an analytical instrument will be illustrated and described hereinafter with respect to FIG. 18.

The ion source is illustrated in FIG. 1 as comprising a conventional electrospray ionizer 16 having an inlet receiving sample droplets of a solution provided by a conventional syringe 14 that may include a conventional syringe pump, and an outlet in fluid communication with an ion source region 18. The electrospray ionizer 16 is operable in a known manner to ionize the sample droplets received from the syringe 14, and provide the ions in the form of a ionized droplets, spray or mist to the ion source region 18. The solution may be or contain biomolecules and/or other molecules. Examples of biomolecules contained in solution include, but are not limited to, DNA, RNA, one or more proteins, peptides, carbohydrates, glycoconjugates and/or the like. In alternative embodiments, sample ions may be generated from samples of any type by one or more other conventional ion generation structures and techniques, and in any case may be supplied to the ion source chamber 18 and/or generated within the ion source chamber 18. Examples of alternative sample ionization structures and techniques include, but are not limited to, laser desorption ionization structures and techniques, such as matrix assisted laser desorption ionization (MALDI), irradiation of samples via other radiation sources, and the like.

The drift tube structure of the IMS 10 of FIG. 1 is illustratively formed by connecting in series any number of drift tube sections, each constructed by compressing between opposing end plates any number of electrically conductive and electrically insulating ring members with an electrically insulating ring member positioned between each adjacent pair of electrically conductive ring members. In the illustrated embodiment, seven such drift tube sections $20_1$-$20_7$ are joined together to define the drift tube structure of the IMS 10. Adjacent ends of the first six drift tube sections $20_1$-$20_6$ are joined together by corresponding drift tube joining structures $21_1$-$21_5$, and adjacent ends of the last two drift tube sections $20_6$ and $20_7$ are joined at an interface with a vacuum chamber 22 in which the last drift tube section $20_7$ resides. Generally, the ion source region 18 defines a first gate, funnel and ion activation region, F1/IA1/G1, and the seven drift tube sections $20_1$-$20_7$ define, when joined together as illustrated in FIG. 1, a first drift tube region, D1, a second gate, funnel and ion activation region, G2/F2/IA2, a second drift tube region, D2, a third funnel region, F3, and a third ion activation region, IA3. An ion inlet of the first drift tube section, D1, is coupled to an ion outlet of the ion source region 18, and an ion outlet of D1 is coupled to an ion inlet of the second gate, funnel and ion activation region G2/F2/IA2. An ion outlet of the second gate, funnel and ion activation region G2/F2/IA2 is coupled to an inlet of the second drift tube region, D2, and an ion outlet of D2 is coupled to an ion inlet of the third funnel region, F3. An ion outlet of the funnel region, F3, is coupled to an ion inlet of the third ion activation region, IA3, which is coupled to a conventional split-field region. An ion outlet of split field region is coupled, via conventional ion focusing optics 24, to the ion acceleration region 26 of the mass spectrometer 12 which resides in a conventional vacuum chamber 28.

In the illustrated embodiment, the mass spectrometer 12 is provided in the form of a reflectron time-of-flight (TOF) mass spectrometer, and a conventional ion detector 29 is positioned to detect ions processed by the mass spectrometer 12. Another ion detector 30 is positioned on-axis with the longitudinal axis of the drift tube structure of the IMS 10, and is used to detect ions exiting the IMS 10. The ion detector 30 may illustratively be a conventional micro-channel plate (MCP) detector, although other known ion detectors may alternatively be used. Moreover, it will be appreciated that one or more additional ion detectors may alternatively be used in the illustrated embodiment as well as with other forms of the mass spectrometer 12. In any case, the ion detector 29 and ion detector 30 are electrically connected to a conventional processor 32. The processor 32 may illustratively be or include any one or more of a conventional personal computer (PC), laptop or notebook computer, hand-held computer device; e.g., personal data assistant (PDA), application specific computer, signal analyzer, or the like, and may include any one or more of a data input device; e.g., keyboard, keypad, point-and-click device, etc., a data storage device, a data display device, data communication device configured for wired or wireless (including internet; e.g., world-wide-web, intranet, infrared, radio frequency, blue-tooth, etc.) communication with one or more other electronic devices. In any case, the ion detectors 29 and 30 are operable in a known manner to detect arrival of ions, and to produce electrical signals corresponding to the ion arrival times. The processor 32 is operable to process the signals provided by the ion detector 30 and determine therefrom ion drift times through the IMS 10 and to process the signals provided by the ion detector 29 and determine therefrom ion flight times through the mass spectrometer A conventional vacuum pump 47 is illustratively coupled via a pair of conduits 49 to the split field region of the IMS 10. By operation of the pump 47, the vacuum chamber 22 is typically maintained at pressures between approximately $3 \times 10^{-5}$-$2 \times 10^{-4}$ Torr, although other operating pressures of the chamber 22 outside of this range are contemplated.

Figure 14:
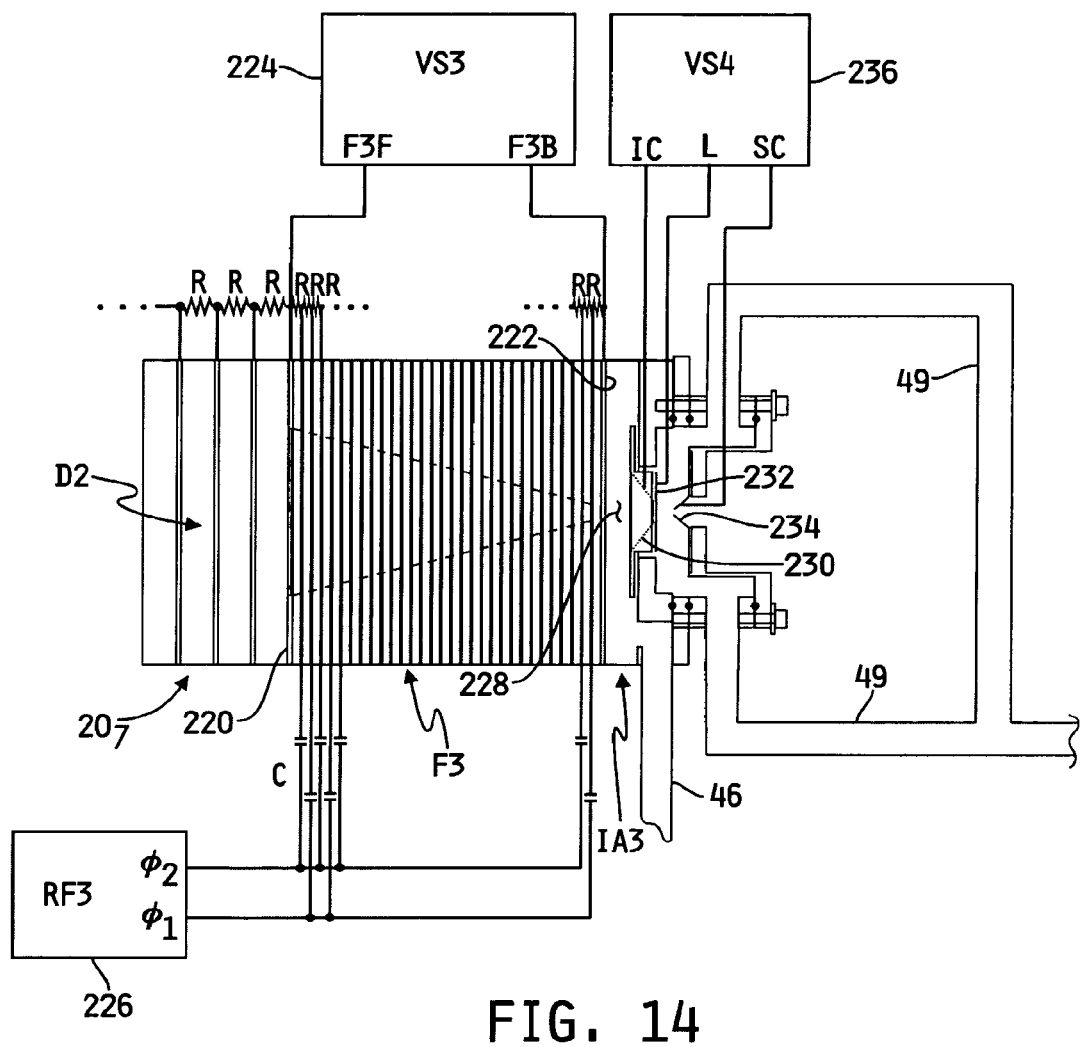
FIG. 14 is a magnified and detailed view of the drift tube section of the ion mobility spectrometer of FIG. 1 that contains the third funnel and ion activation regions.

The IMS 10 defines a gas inlet adjacent to the ion outlet end of the section 20$_7$, which is illustrated in greater detail in FIG. 14. In the embodiment illustrated in FIG. 1, a first gas source 34 is fluidly coupled to an inlet of a first conventional valve 36 having an outlet coupled to a pipe or conduit 38. A second gas source 40 may optionally be included, and if so is fluidly coupled to an inlet of a second conventional valve 42 having an outlet coupled to another pipe or conduit 44. The pipes or conduits 38 and 44 are both fluidly coupled via another pipe or conduit 46 through the chamber 22 to the gas inlet defined by the IMS 10. Illustratively, the first gas source 34 is a buffer gas, and the valve 36 is controllable to selectively provide the buffer gas to the interior of the IMS 10. An example of a suitable buffer gas includes, but is not limited to, helium. The second gas source 40 may illustratively be a doping gas suitable for mixing with the buffer gas supplied by the first gas source 34, as will be described in greater detail hereinafter. An example of a suitable mixing gas includes, but is not limited to, nitrogen. In any case, the valves 36 and 42 may be conventionally controlled or may alternatively be programmably controlled by the processor 32 as shown in phantom.

A number of voltage sources control the operation of the IMS 10 and the operation of the mass spectrometer 12. Operation of the mass spectrometer 12 is conventional, and any voltage sources required for controlling operation of the mass spectrometer 12 are therefore not shown in FIG. 1. With regard to the IMS 10, a first DC voltage source, VS1, and a first radio frequency voltage source, RF1, are each electrically connected to the ion source, which includes the sample solution 14, the electrospray ionizer 16 and the ion source region 18. A second DC voltage source, VS2, and a second radio frequency voltage source, RF2, are each electrically connected to the second gate, funnel and ion activation region, G2/F2/IA2. A programmable delay generator, PDG, is electrically connected between the first and second DC voltage sources VS1 and VS2, the purpose of which will be described hereinafter. A third DC voltage source, VS3, and a third radio frequency voltage source, RF3, are each electrically connected to the third funnel region, F3. A fourth DC voltage source, VS4, is electrically connected to the split-field region at the ion outlet end of the section 20$_7$. Details relating to exemplary embodiments of each of these voltage sources will be described hereinafter. In any case, any one or more of the voltage sources VS1-VS4 and RF1-RF3 may be, and/or may include one or more individual voltage supplies that are, manually controlled and/or programmable to operate at least semi-automatically. Alternatively or additionally, any one or more of the voltage sources VS1-VS4 and RF1-RF3 may be, and/or may include one or more individual voltage supplies that are, electrically connected to the processor 32, as shown in phantom in FIG. 1, so that the processor 32 may control, at least partially, any one or more of the voltage sources VS1-VS4 and RF1-RF3 and/or one or more individual voltage supplies included therein.

Figure 2:
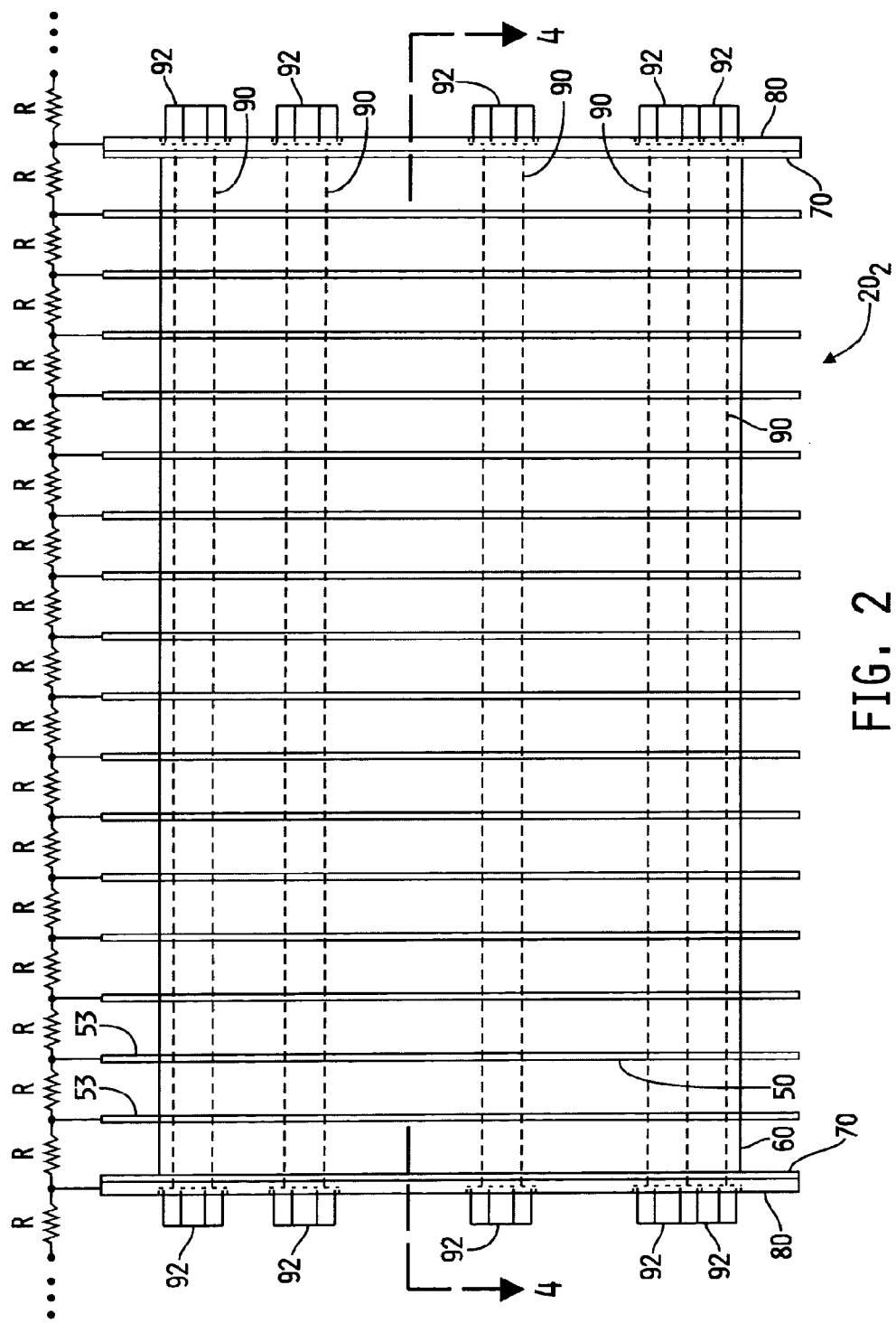
FIG. 2 is a magnified and detailed view of one of the drift tube sections of the ion mobility spectrometer of FIG. 1.

Referring now to FIGS. 2-5, details relating to one complete drift tube section of the drift tube structure comprising the IMS 10 is shown. Specifically, FIGS. 2-5 illustrate details relating to the section 20$_2$ of the first drift tube region D1 outlined by the dashed-line block 2 of FIG. 1, although it will be understood that the section 20$_2$ is generally representative of any of the other drift tube sections 20$_1$, 20$_3$, 20$_5$ and 20$_6$. Referring particularly to FIG. 2, the section 20$_2$ comprises a series of electrically conductive ring members 50 with electrically insulating ring members 60 positioned between each adjacent pair of electrically conductive ring members 50. In the exemplary embodiment, the drift tube section 20$_2$ illustratively includes 16 electrically conductive ring members 50 and 17 electrically insulating ring members 60, although it should be understood that the drift tube section 20$_2$ may alternatively include more or fewer such ring members 50 and 60. Generally, the lengths of the drift tube regions D1 and D2 are defined by the number of ring members 50 and 60 and drift tube region end sections making up these regions, and the lengths of these regions D1 and D2 may accordingly be modified simply by including more or fewer ring members 50 and 60 and/or by including more or fewer drift tube sections.

Figure 3A:
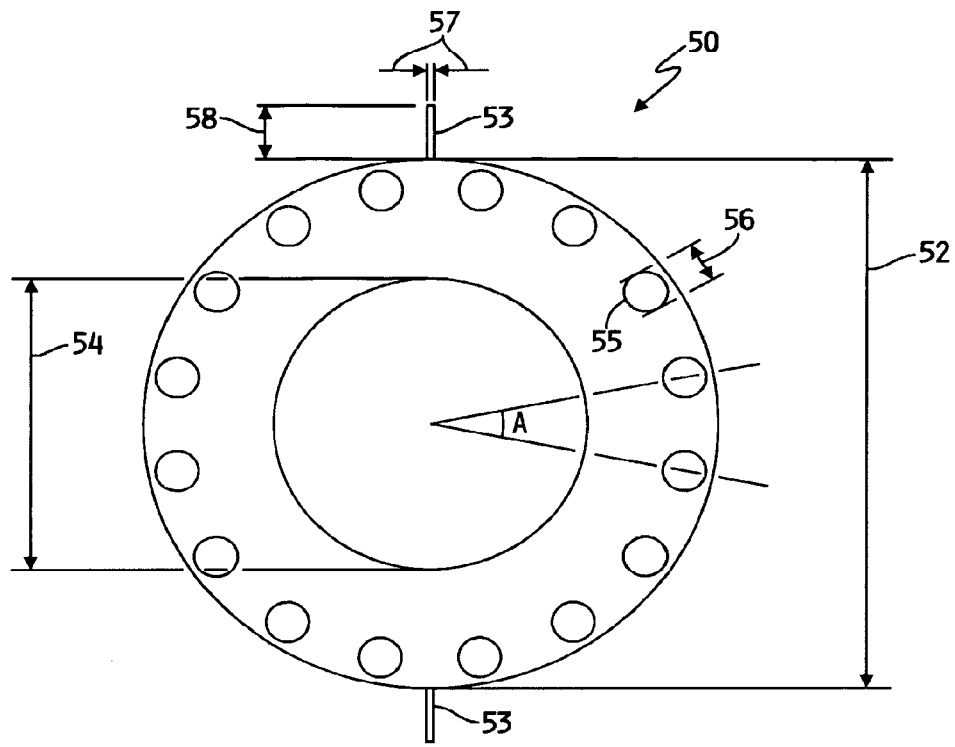
FIG. 3A is a front elevational view of an electrically conductive ring member used in the construction of the drift tube section of FIG. 2.

Referring now to FIG. 3A, one illustrative embodiment of one of the electrically conductive drift tube ring members 50 is shown. In the illustrated embodiment, the electrically conductive drift tube ring member 50 is an annular ring member having an outer diameter 52 and a smaller inner diameter 54 defined by an annular passageway extending centrally therethrough. A plate region is defined between the outer periphery and the inner periphery of the ring member 50, and the plate region has a predefined thickness. Just inboard of the outer periphery of the plate region, the ring member 50 defines therethrough a number of equi-angularly spaced holes 55 each having a predefined hole diameter 56. In the illustrated embodiment, 16 such holes 55 are shown, although it will be understood that the ring member 50 may alternatively define more or fewer such holes 55 therethrough. In any case, the holes 55 are each spaced apart by an angle of "A" relative to a center of the ring member 50. Opposing faces of the ring member 50 are, in the illustrated embodiment, identical.

A pair of posts 53 extend from the outer periphery of the ring member 50 at opposite ends of a plane bisecting the ring member 50. Each post 53 is positioned midway between two adjacent holes 55. The posts 53 have a predefined height 58 and a predefined width 57, and are of the same thickness as the plate region of the ring member 50. The ring member 50 may illustratively be constructed of stainless steel, although other electrically conductive materials may alternatively or additionally be used. The following Table I provides example dimensional information for one specific implementation of the ring members 50, although it will be understood that any one or more of the example dimensions may be modified to suit alternate implementations of the IMS 10.

TABLE I

| Drift Tube Ring Member 50 | Dimension/Units |
| --- | --- |
| outer diameter 52 | 12.7 cm |
| inner diameter 54 | 6.985 cm |
| ring member thickness | 0.15875 cm |
| diameter 56 of the holes 55 | clearance for 0.9525 cm (3/8 inch) rod |
| position of holes 55 relative to the ring member 50 | 11.43 cm diameter B.C. |
| angle "A" | 22.5 degrees |
| height 58 of the posts 53 | 1.27 cm |
| width 57 of the posts 53 | 0.15875 cm |

Figure 3B:
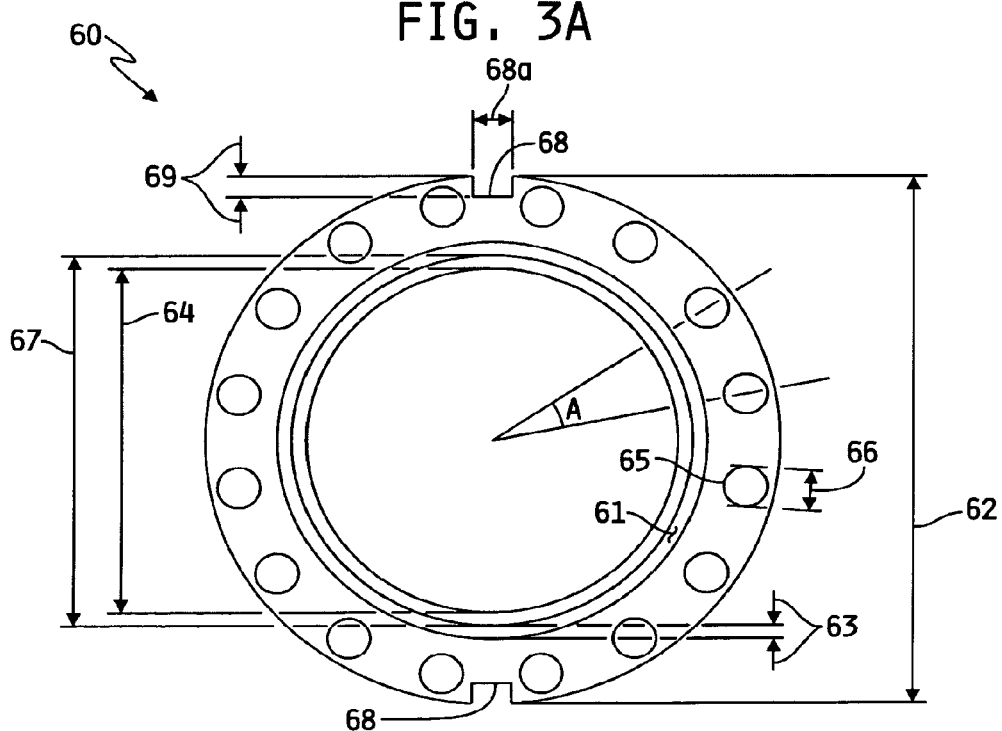
FIG. 3B is a front elevational view of an electrically insulating ring member used in the construction of the drift tube section of FIG. 2.

Referring now to FIG. 3B, one illustrative embodiment of one of the electrically insulating drift tube ring members 60 is shown. In the illustrated embodiment, the electrically insulating drift tube ring member 60 is an annular ring member having an outer diameter 62 and a smaller inner diameter 64 defined by an annular passageway extending centrally therethrough. A plate region is defined between the outer periphery and the inner periphery of the ring member 60, and the plate region has a predefined thickness. Just inboard of the outer periphery of the plate region, the ring member 60 defines therethrough a number of equi-angularly spaced holes 65 each having a predefined hole diameter 66. In the illustrated embodiment, 16 such holes 65 are shown that align with the 16 holes 55 of the example ring member 50 illustrated in FIG. 3A when the ring members 50 and 60 are juxtaposed, although it will be understood that the ring member 60 may alternatively define more or fewer such holes 65 therethrough. In any case, the holes 65 are each spaced apart by an angle of "A" relative to a center of the ring member 60.

A pair of channels 68, each having a predefined depth 69, extend into the outer periphery of the ring member 60 at opposite ends of a plane bisecting the ring member 60. Each channel 68 is positioned midway between two adjacent holes 65, and each channel 68 aligns with a corresponding one of the posts 53 extending from the outer periphery of the ring member 50 when the ring members 50 and 60 are juxtaposed such that the posts 53 are centered relative to a width 68a of each of the channels 68. The ring member 60 further defines an annular channel 61 about the plate region inboard of its inner periphery. The annular channel 61 defines a channel width 63 and an inner diameter 67. The annular channel 61 is sized to receive therein an annular sealing ring, or O-ring (not shown in FIG. 3B). Opposing faces of the ring member 60 are, in the illustrated embodiment, identical.

The electrically insulating ring member 60 may illustratively be constructed of Delrin® acetal resin although other electrically insulating materials may alternatively or additionally be used. The following Table II provides example dimensional information for one specific implementation of the ring members 60, although it will be understood that any one or more of the example dimensions may be modified to suit alternate implementations of the IMS 10.

TABLE II

| Drift Tube Ring Member 60 | Dimension/Units |
| --- | --- |
| outer diameter 62 | 12.7 cm |
| inner diameter 64 | 8.255 cm |
| ring member thickness | 1.27 cm |
| diameter 66 of the holes 55 | clearance for 0.9525 cm (3/8 inch) rod |

TABLE II-continued

| Drift Tube Ring Member 60 | Dimension/Units |
| --- | --- |
| position of holes 65 relative to the ring member 60 | 11.43 cm diameter B.C. |
| angle "A" | 22.5 degrees |
| depth 69 of the channel 68 | 0.508 cm |
| width 68a of the channel 68 | 0.889 cm |
| width 63 of the annular channel 61 | sized to receive and hold therein a 0.3175 cm (1/8 inch) thick flexible O-ring |
| inner diameter 67 of the annular channel 61 | 8.89 cm |

Referring again to FIG. 2, the section $20_2$ further includes a pair of electrically conductive drift tube end ring members 70 each positioned adjacent to the last electrically insulating ring member 60 at each end of the section $20_2$, followed by a pair of electrically conductive drift tube end plate members 80 each positioned adjacent to corresponding ones of the drift tube end ring member 70.

Referring now to FIG. 3C, one illustrative embodiment of one of the electrically conductive drift tube ring members 70 is shown. In the illustrated embodiment, the electrically conductive drift tube end ring member 70 is an annular ring member having an outer diameter 72 and a smaller inner diameter 74 defined by an annular passageway extending centrally therethrough. A plate region is defined between the outer periphery and the inner periphery of the ring member 70, and the plate region has a predefined thickness. Between the outer periphery and the inner periphery of the ring member 70, the plate region defines therethrough a number of equi-angularly spaced holes 75 each having a predefined hole diameter 76. In the illustrated embodiment, 16 such holes 75 are shown that align with the 16 holes 55 and 65 of the example ring members 50 and 60 illustrated in FIGS. 3A and 3B respectively when the ring members 70 are juxtaposed with the last ring members 60 at the ends of the drift tube section $20_2$, although it will be understood that the ring member 70 may alternatively define more or fewer such holes 75 therethrough. In any case, the holes 75 are each spaced apart by an angle of "A" relative to a center of the ring member 70. Just inboard of the outer periphery of the plate region, the ring member 70 further defines therethrough a number of equi-angularly spaced and alternating holes 78 and 79, each having predefined hole diameters. In the illustrated embodiment, 16 such holes are shown in an alternating pattern of holes 78 and 79 although it will be understood that the ring member 70 may alternatively define more or fewer such holes therethrough. In any case, adjacent pairs of the holes 78 and 79 are each spaced apart by an angle of "A" relative to a center of the ring member 70. Opposing faces of the ring member 70 are, in the illustrated embodiment, identical. The ring member 70 may illustratively be constructed of stainless steel, although other electrically conductive materials may alternatively or additionally be used. The following Table III provides example dimensional information for one specific implementation of the ring members 70, although it will be understood that any one or more of the example dimensions may be modified to suit alternate implementations of the IMS 10.

TABLE III

| Drift Tube End Ring Member 70 | Dimension/Units |
| --- | --- |
| outer diameter 72 | 15.24 cm |
| inner diameter 74 | 6.985 cm |
| ring member thickness | 0.15875 cm |
| diameter 76 of the holes 55 | clearance for 0.9525 cm (3/8 inch) rod |

TABLE III-continued

| Drift Tube End Ring Member 70 | Dimension/Units |
|---|---|
| position of holes 75 relative to the ring member 70 | 11.43 cm diameter B.C. |
| angle "A" | 22.5 degrees |
| diameter of the holes 78 | clearance for 0.635 cm (¼ inch) rod |
| position of holes 78 relative to the end ring member 70 | 14.478 cm diameter B.C. |
| diameter of holes 79 | clearance for #32 screw |
| position of holes 79 relative to the end ring member 70 | 14.478 cm diameter B.C. |

Referring now to FIGS. 3D and 3E, one illustrative embodiment of one of the electrically conductive drift tube end plate members 80 is shown. In the illustrated embodiment, the electrically conductive drift tube end plate member 80 is an annular plate member having an outer diameter 82 and a smaller inner diameter 84 defined by an annular passageway extending centrally therethrough. A plate region is defined between the outer periphery and the inner periphery of the plate member 80, and the plate region has a predefined thickness. Between the outer periphery and the inner periphery of the plate member 80, the plate region defines therethrough a number of equi-angularly spaced holes 85 each having a predefined hole diameter 86. In the illustrated embodiment, 16 such holes 85 are shown that align with the 16 holes 55, 65 and 75 of the example ring members 50, 60 and 70 illustrated in FIGS. 3A-3C respectively when the end plate members 80 are juxtaposed with the end ring members 70 at the ends of the drift tube section $20_2$, although it will be understood that the plate member 80 may alternatively define more or fewer such holes 85 therethrough. In any case, the holes 85 are each spaced apart by an angle of "A" relative to a center of the plate member 80. Just inboard of the outer periphery of the plate region, the plate member 80 further defines therethrough a number of equi-angularly spaced and alternating holes 88 and 89, each having predefined hole diameters. In the illustrated embodiment, 16 such holes are shown in an alternating pattern of holes 88 and 89 although it will be understood that the plate member 80 may alternatively define more or fewer such holes therethrough. In any case, adjacent pairs of the holes 88 and 89 are each spaced apart by an angle of "A" relative to a center of the plate member 80.

Opposing faces of the plate member 80 are, in the illustrated embodiment, not identical. Rather one face of the plate member 80, i.e., the face illustrated in FIG. 3D, is juxtaposed with a corresponding one of the end ring members 70, whereas the opposite face of the plate member, i.e., the face illustrated in FIG. 3E, is configured differently. More specifically, each hole 85 extending through the plate region is surrounded on the face illustrated in FIG. 3E with a channel 83 having an outer diameter 87 and a predefined depth. In the illustrated embodiment, the channels 83 are configured to receive therein correspondingly sized nuts configured to engage compression rods extending through the drift tube section $20_2$ as will be described more fully hereinafter. The end plate member 80 may illustratively be constructed of stainless steel, although other electrically conductive materials may alternatively or additionally be used. The following Table IV provides example dimensional information for one specific implementation of the end plate members 80, although it will be understood that any one or more of the example dimensions may be modified to suit alternate implementations of the IMS 10.

TABLE IV

| Drift Tube End Plate Member 80 | Dimension/Units |
|---|---|
| outer diameter 82 | 15.24 cm |
| inner diameter 84 | 10.16 cm |
| ring member thickness | 0.3175 cm |
| diameter 86 of the holes 85 | clearance for 0.9525 cm (⅜ inch) rod |
| position of holes 85 relative to the end plate member 80 | 11.43 cm diameter B.C. |
| angle "A" | 22.5 degrees |
| diameter of the holes 88 | clearance for 0.635 cm (¼ inch) rod |
| position of holes 88 relative to the end plate member 80 | 14.478 cm diameter B.C. |
| diameter of the holes 89 | clearance for #32 screw |
| position of holes 89 relative to the end plate member 80 | 14.478 cm diameter B.C. |
| diameter 87 of the channels 83 | clearance for 0.9525 cm (⅜ inch) threaded nut centered over hole 85 |
| depth of the channels 83 | 0.15875 cm |

Referring again to FIG. 2, a number of rods 90 extend through a corresponding number of aligned holes 55, 65, 75 and 85 of the series of juxtaposed rings 50, 60, 70 and plates 80 respectively. Correspondingly sized nuts 92 are configured to engage opposite ends of each rod 90, and the nuts 92 are configured to be advanced onto the opposite ends of the rods 90 to thereby compress the rings 50, 60, 70 and plates 80 together. In the illustrated embodiment, as most clearly illustrated in FIGS. 2 and 5, eight such rods 90 extend through every other set of aligned holes 55, 65, 75 and 85 of the rings 50, 60, 70 and plates 80, and 16 correspondingly sized nuts 92 engage opposite ends of the rods 90. At least the opposite ends of the rods 90 are threaded, and the nuts 92 are correspondingly threaded so that they may be advanced onto the rods 90. The rods 90 are sized in length so that the nuts 92, when fully advanced onto the rods 90 so that the rings 50, 60, 70 and plates 80 are sufficiently compressed to form an airtight seal between the rings 50, 60 and 70, are received within the channels 83 surrounding the holes 85 in the end plates 80 with the ends of the rods 90 flush with or slightly recessed within the opposite ends of the nuts 90. It will be understood, however, that more or fewer rods 90 and corresponding nuts 92 may be used to compress the rings 50, 60, 70 and end plates 80 together to form the drift tube section $20_2$. In any case, the rods and nuts 90 are illustratively formed of electrically insulating materials, one example of which is, but should not be limited to, nylon. Those skilled in the art will recognize that other suitable electrically insulating materials may be used for the rods 90 and/or nuts 92.

As illustrated in FIG. 2, a string of equal-valued resistors, R, are connected in series with each other, and each resistor, R, is connected between the posts 53 of adjacent rings 50 and also between the posts 53 of the last rings 50 and the adjacent end rings 70 or end plates 80. Unless otherwise noted herein, the resistor string comprising the series connection of resistors, R, extends the entire length of the IMS 10 from the first ring 50 in the first drift tube, D1, to the last ring 50 of the third funnel section, F3. Although not shown in an assembly view, the channels 68 formed in the electrically insulating rings 60 align between the posts 53 in the drift tube section $20_2$ to facilitate electrical connection access to the posts 53.

Figure 4:
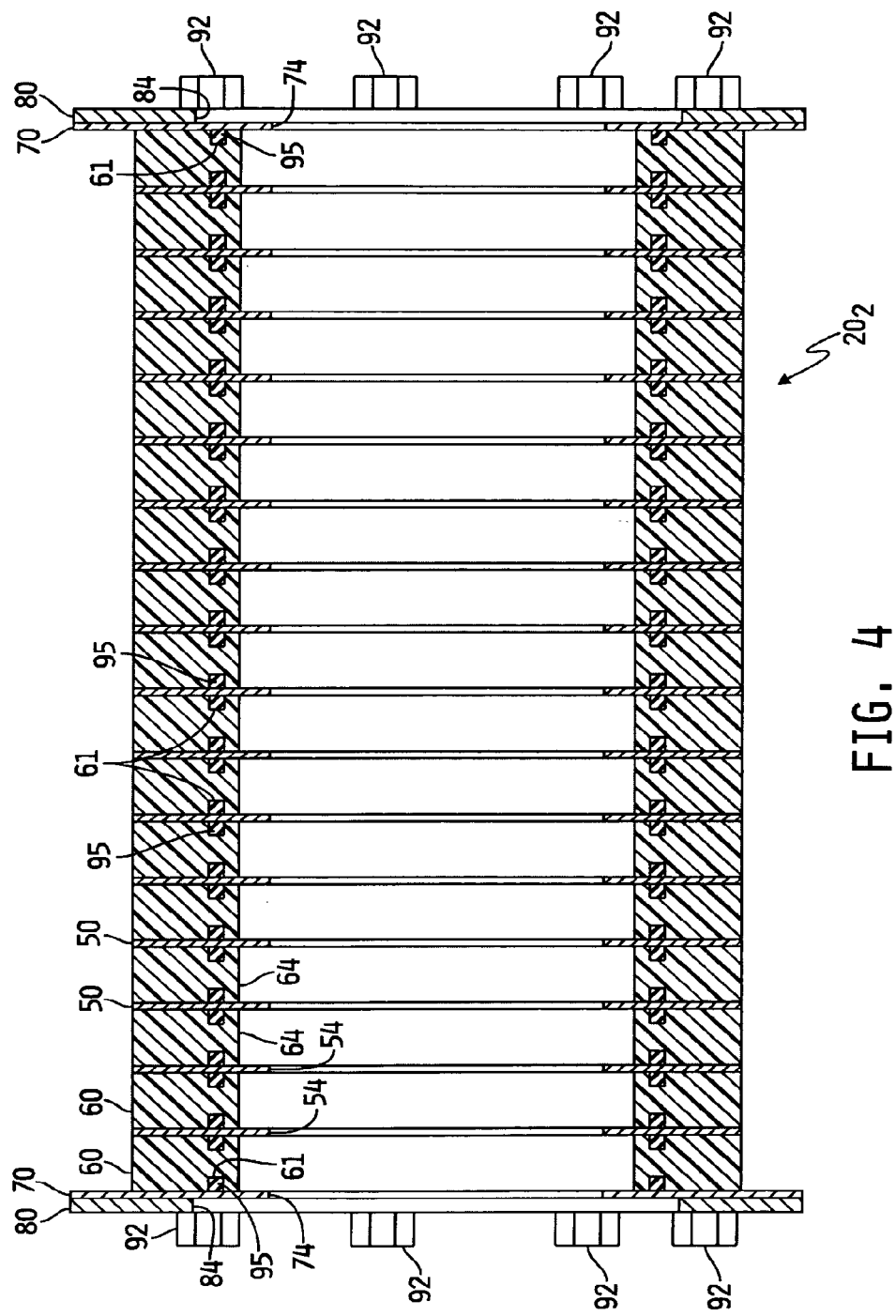
FIG. 4 is a cross-sectional view of the drift tube section of FIG. 2, viewed along section lines 4-4.

Referring now to FIG. 4, a cross-section of the drift tube section $20_2$ is shown as viewed along section lines 4-4 of FIG. 2. In this figure, a sealing ring 95 is received in each of the annular channels 61 formed in both faces of each electrically insulating ring member 60. The sealing ring 95 may illustratively be a flexible O-ring formed of a suitable material that facilitates an air-tight seal between both faces of each electrically insulating member 60 and an adjacent ring member 50 or 70 when the ring members 50, 60, 70 and plate members 80 are compressed by the rods 90 and nuts 92 as previously described. Examples of materials that may be used to form the sealing rings 95 include, but are not limited to, rubber, nylon, flexible polymer material, and the like. Alternatively, the sealing rings 95 may be formed from one or more suitable rigid and/or semi-rigid material. In any case, the sealing rings 95 and ring members 50, 60 and 70 cooperate, when compressed by the rods 90 and nuts 92, to form an air-tight chamber within the drift tube section $20_2$ between each end ring member 70.

Figure 6:
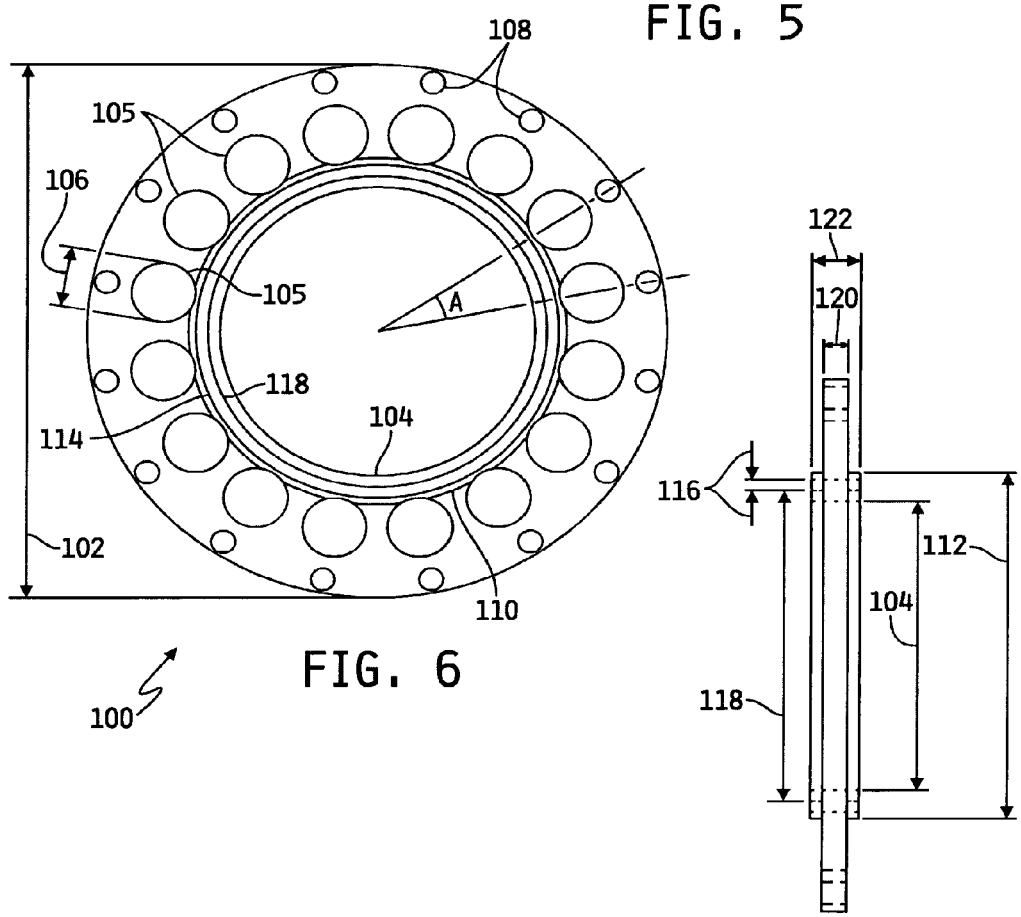
FIG. 6 is a front elevational view of a junction ring member used to connect together two adjacent drift tube sections.
Figure 7:
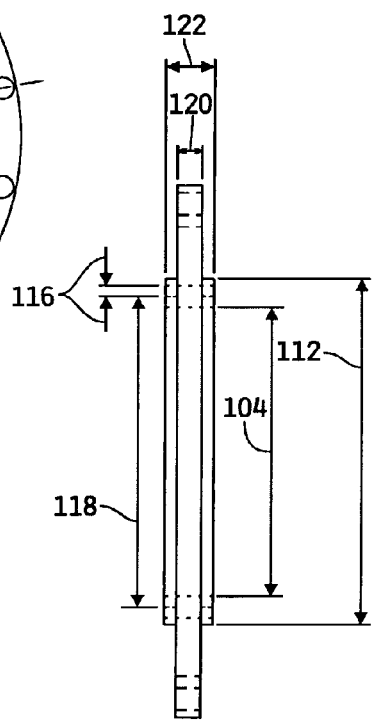
FIG. 7 is a side elevational view of the junction ring member of FIG. 6.

The drift tube sections $20_1$-$20_7$ of the IMS 10 are joined together via electrically insulating junction plate members 100 that cooperate with the end plate members 80 of each drift tube section and also with the drift tube end rings 70 of each section to form an air-tight connection between each section. Referring to FIGS. 6 and 7, one illustrative embodiment of one of the electrically insulating junction plate members 100 is shown. In the illustrated embodiment, the electrically insulating junction plate member 100 is an annular ring member having an outer diameter 102 and a smaller inner diameter 104 defined by an annular passageway extending centrally therethrough. A stepped plate region 110 is defined between the outer periphery and the inner periphery of the plate member 100. An annular outer plate region extends between the outer periphery of the plate member 100 and the stepped plate region 110, and the outer plate region has a predefined thickness 120. The stepped plate region 110 is likewise annular in shape and extends between the outer plate region and the inner periphery of the plate member 100. The stepped plate region 110 has a thickness 122 that is greater than the thickness 120 of the outer plate region. The thickness of the stepped plate region 110 is selected so that the faces of the stepped plate region 110 are juxtaposed with the faces of the drift tube end ring members 70 when the junction plate member 100 is compressed between the ends of two drift tube sections.

Just inboard of the outer periphery of the plate member 100, the outer plate region defines therethrough a number of equi-angularly spaced holes 105 each having a predefined hole diameter 106. In the illustrated embodiment, 16 such holes 105 are shown that align with the 16 holes 85 of the end plate members 80 illustrated in FIGS. 3D, 3E and 5 when the plate members 80 and 100 are juxtaposed, although it will be understood that the junction plate member 100 may alternatively define more or fewer such holes 105 therethrough. In any case, the holes 105 are each spaced apart by an angle of "A" relative to a center of the plate member 100. Just inboard of the outer periphery of the outer plate region, the plate member 100 further defines therethrough a number of equi-angularly spaced holes 108 having predefined hole diameters. In the illustrated embodiment, 16 such holes are shown although it will be understood that the plate member 100 may alternatively define more or fewer such holes 108 therethrough. In any case, the holes 108 are each spaced apart by an angle of "A" relative to a center of the plate member 100.

The plate member 100 further defines an annular channel 114 in and about the stepped plate region 110 inboard of the inner periphery of the plate member 100. The annular channel 114 defines a channel width 116 and an inner diameter 118. The annular channel 114 is sized to receive therein an annular sealing ring, or O-ring (not shown in FIGS. 6 and 7), such as a flexible O-ring 95 as described hereinabove. Opposing faces of the junction plate member 100 are, in the illustrated embodiment, identical.

The electrically insulating junction plate member 100 may illustratively be constructed of Delrin® acetal resin although other electrically insulating materials may alternatively or additionally be used. The following Table V provides example dimensional information for one specific implementation of the junction plate members 100, although it will be understood that any one or more of the example dimensions may be modified to suit alternate implementations of the IMS 10.

TABLE V

| Junction Plate Member 100 | Dimension/Units |
|---|---|
| outer diameter 102 | 15.24 cm |
| inner diameter 104 | 8.255 cm |
| plate member thickness 120 | 0.635 cm |
| stepped region thickness 122 | 1.27 cm |
| diameter 106 of the holes 105 | clearance for 0.9525 cm (⅜ inch) nut (1.7 cm dia.) |
| position of holes 105 relative to the junction plate member 100 | 11.43 cm diameter B.C. |
| angle "A" | 22.5 degrees |
| diameter of the holes 108 | clearance for 0.635 cm rod or post |
| position of holes 108 relative to the junction plate member 100 | 14.478 cm diameter B.C. |
| width 116 of the annular channel 114 | sized to receive and hold therein a 0.3175 cm (⅛ inch) thick flexible O-ring |
| inner diameter 118 of the annular channel 114 | 8.89 cm |

Figure 8:
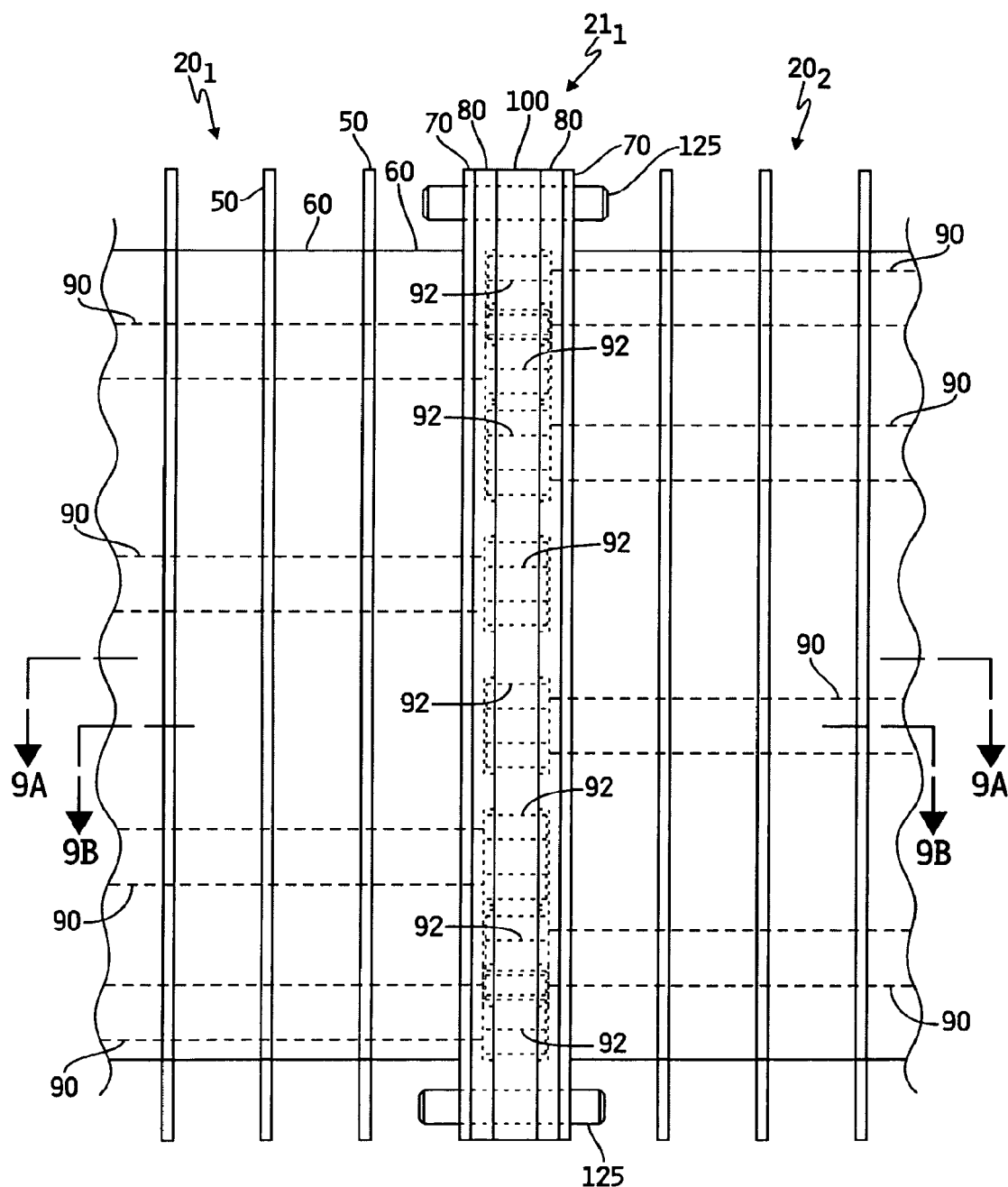
FIG. 8 is a magnified view of one of the drift tube joining structures of the ion mobility spectrometer of FIG. 1.
Figure 9A:
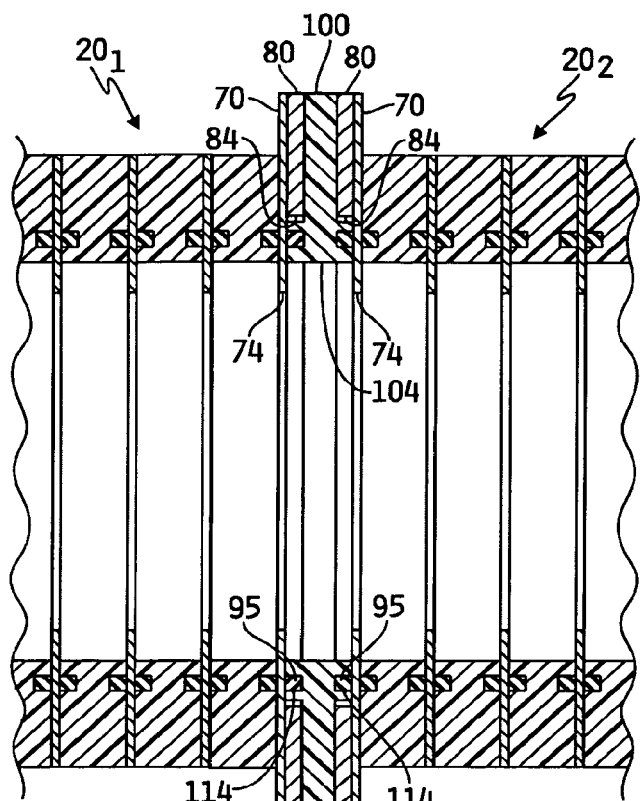
FIG. 9A is a cross-sectional view of the drift tube joining structure of FIG. 8, viewed along section lines 9A-9A.
Figure 9B:
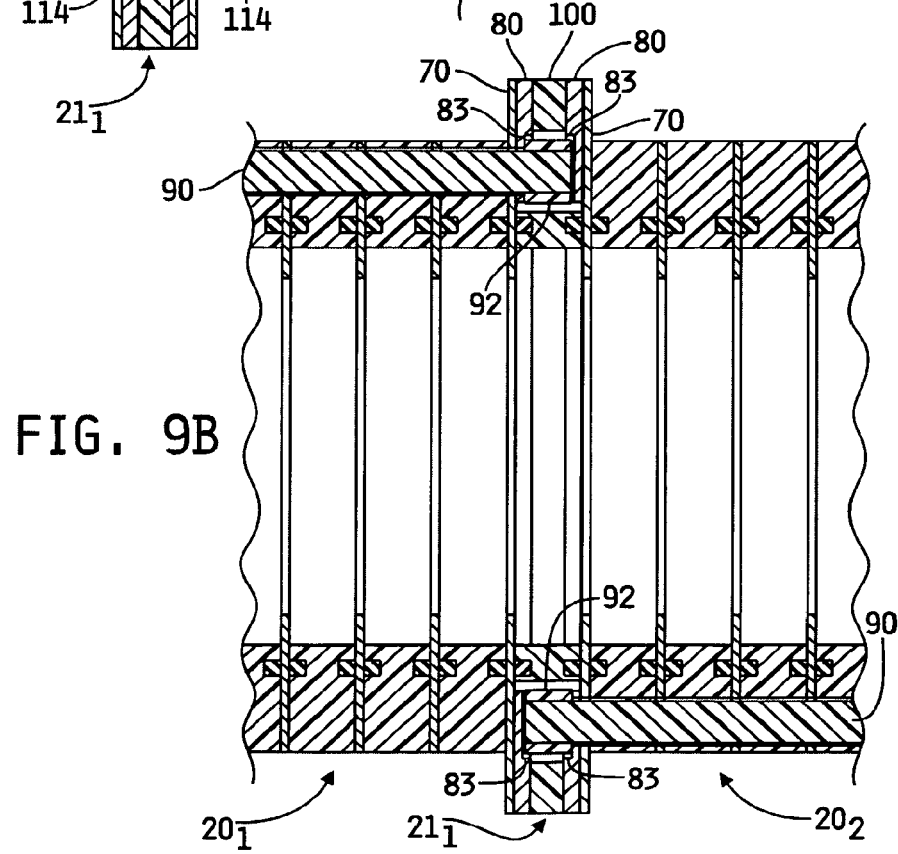
FIG. 9B is a cross-sectional view of the drift tube joining structure of FIG. 8, viewed along section lines 9B-9B.

Referring now to FIGS. 8, 9A and 9B, details relating to the connection of two adjacent drift tube sections, using the electrically insulating junction plate member 100 of FIGS. 6 and 7, is shown. Specifically, FIGS. 8, 9A and 9B illustrate details relating to the drift tube connection structure $21_5$, outlined by the dashed-line block 8 of FIG. 1, that connects the drift tube sections $20_5$ and $20_6$, although it will be understood that the drift tube connection structure $21_5$ is generally representative of any of the other drift tube connection structures $21_1$-$21_4$. Referring particularly to FIG. 8, the drift tube connection structure section $21_5$ comprises the drift tube end ring 70 and the drift tube end plate 80 of the drift tube section $20_5$, the drift tube end ring 70 and the drift tube end plate 80 of the drift tube section $20_6$ and the junction plate 100 positioned between the drift tube sections $20_5$ and $20_6$.

Figure 5:
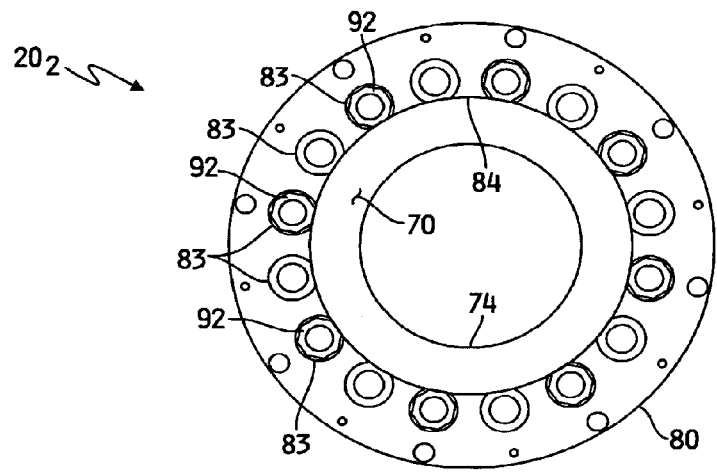
FIG. 5 is an end elevational view off the drift tube section of FIG. 2.

As described hereinabove with respect to FIGS. 2 and 5, the compression rods 90 in the illustrated example extend through every other sets of aligned holes 55, 65, 75 and 85 of the rings 50, 60, 70 and plate 80. For drift tube sections that will be connected together as shown in FIGS. 8, 9A and 9B, the rods 90 extend through one set of eight holes 55, 65, 75 and 85 in one drift tube section $20_5$ or $20_6$, and the rods 90 extend through the other set of eight hoes 55, 65, 75 and 85 in the other drift tube section $20_5$ or $20_6$. When the two drift tube sections $20_5$ and $20_6$ are joined together with the junction plate 100 positioned therebetween as illustrated in FIGS. 8, 9A and 9B, 16 rods 90 and nuts 92 therefore extend through each of the 16 holes 105 in the junction plate 100; eight from one direction and eight from the other. As most clearly shown in FIG. 9B, the rods 90 and nuts 92 extend into the channels 83 defined in each of the drift tube end plates 80 when two drift tube sections $20_5$ and $20_6$ are brought together.

With the junction plate 100 in place, the two drift tube sections $20_5$ and $20_6$ are secured together by a number of fixation members 125 extending through the holes 78 and/or 79, 88 and/or 89 and 108 defined through the ring 70, end plate 80 and junction plate 100 respectively. A sealing ring 95 is received in each of the annular channels 114 formed in both faces of the electrically insulating junction plate member 100. The sealing ring 95 may illustratively be a flexible O-ring formed of a suitable material that facilitates an air-tight seal between the two faces of the electrically insulating junction plate member 100 and corresponding faces of the adjacent ring members 70 when the ring members 70 and plate members 80 and 100 are compressed together by the fixation members 125. Examples of materials that may be used to form the sealing rings 95 include, but are not limited to, rubber, nylon, flexible polymer material, and the like. Alternatively, the sealing rings 95 may be formed from one or more suitable rigid and/or semi-rigid material. In any case, the sealing rings 95, ring members 70 and plate member 100 cooperate, when compressed by the fixation members 125, to form an air-tight seal between the chambers defined by the drift tube sections $20_5$ and $20_6$.

Figure 10:
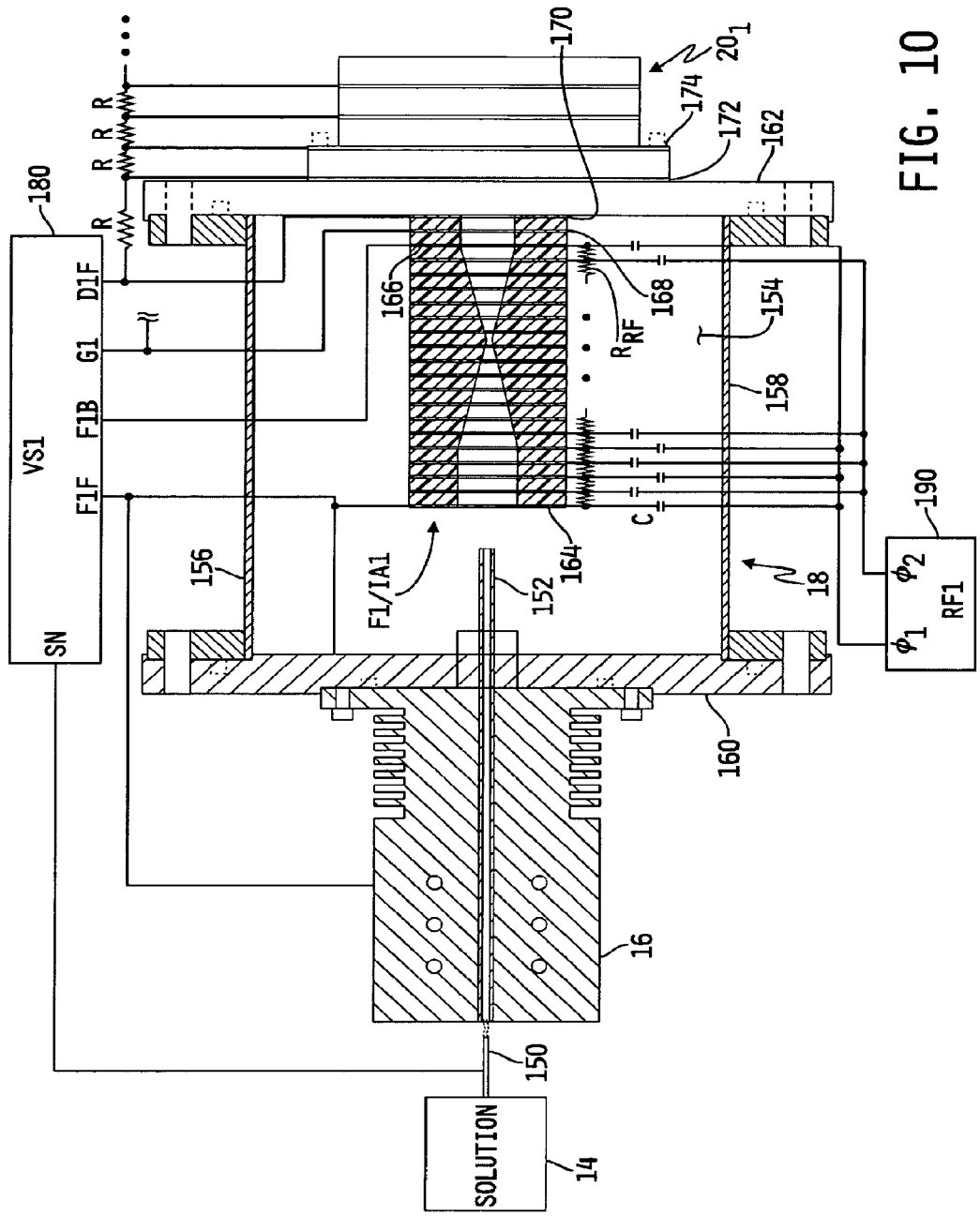
FIG. 10 is a magnified and partial cross-sectional view of the ion source section of the ion mobility spectrometer of FIG. 1.

Referring now to FIG. 10, a partial cross-sectional view of one illustrative embodiment of the ion source portion of the IMS 10 of FIG. 1 is shown. In the illustrated embodiment, the ion source includes a conventional electrospray ionizer 16 having an inlet receiving sample droplets of a solution provided by a needle 150 of a conventional syringe 14, and an outlet, in the form of a capillary 152, in fluid communication with an ion source region 18. The capillary 152 may illustratively be a conventional pull-tip capillary having an inner diameter of, e.g., 75 μm, and an outer diameter of, e.g., 360 μm. A PEEK microtee may be used in the electrospray assembly to couple the tip of the capillary 152, an electrically conductive wire and the syringe 14. As described hereinabove, the electrospray ionizer 16 is operable in a known manner to ionize the sample droplets received from the syringe 14, and provide the ions in the form of a ionized droplets, spray or mist to the ion source region 18. The syringe 14 may include a conventional pump, and solution flow rates may be, for example, but should not be limited to, 0.25 μL/min. The solution may be or contain biomolecules and/or other molecules, examples of which are described hereinabove. In alternative embodiments, sample ions may be generated from one or more samples of any type by one or more other conventional ion generation structures and techniques, examples of which are described hereinabove, and in any case may be supplied to the ion source chamber 18 and/or generated within the ion source chamber 18.

In the illustrated embodiment, the ion source region 18 includes a chamber 154 defined between a pair of side walls 156 and 158, a front wall 160 and a back wall 162. The electrospray ionizer 16 is mounted to the front wall 160, and the capillary 152 of the ionizer 16 extends through the front wall 160 into the chamber 154. The back end of a funnel and ion activation structure, F1/IA1, is mounted to the rear wall 162, and a front end of the funnel and ion activation structure, F1/IA1, extends from the rear wall 162 into the chamber 154. The funnel and ion activation structure, F1/IA1, defines an ion passageway therethrough, and the front end of the funnel and ion activation structure, F1/IA1, is positioned within the chamber 154 so that an entrance to the ion passageway of F1/IA1 is approximately centered with the longitudinal axis of the capillary 154.

The funnel and ion activation structure, F1/IA1, is illustratively formed by compressing together a number of alternating electrically conductive and electrically insulating ring members, or lenses, similarly as described hereinabove with respect to FIGS. 2-9B. The resulting funnel and ion activation structure, F1/IA1, is generally defined between a first or front lens 164 and a last or back lens 166. In one exemplary embodiment, the funnel and ion activation structure, F1/IA1, is formed by compressing together 96 concentric brass electrodes, e.g., 0.5 mm thick, that are each electrically isolated by Teflon® fluoropolymer resin ring members, e.g., 0.76 mm thick. The first 36 concentric electrodes, or lenses, maintain a constant inner diameter, e.g., 25.4 mm, followed by 34 lenses with linearly decreasing inner diameters, e.g., from 25.4 mm to 2.1 mm. The last section of the funnel and ion activation structure, F1/IA1, comprises 26 lenses having inner diameters that increase linearly, e.g., from 2.82 mm to 20.45 mm. An electrically insulating ring member is positioned between the back funnel lens 166 and a gate lens (G1) 168, and another electrically insulating ring member is positioned between the gate lens 168 and the first ring or lens 170 of the first drift tube region, D1. The second and third rings or lenses 172 and 174 are also identified in FIG. 10. In the exemplary embodiment, the gate lens 168 and the first lens of D1 170 are both brass lenses, e.g., 20.45 mm inner diameter. The gate lens 168 also includes a nickel mesh grid, e.g., 90% ion transmittance, over its face. Illustratively, a number of rods and nuts may be used to mount the funnel and ion activation structure, F1/IA1, to the rear wall 162, as described hereinabove with respect to FIGS. 2-5, although such a mounting structure is not shown in FIG. 10 in favor of promoting clarity of the other illustrated components.

The ion source region illustrated in FIG. 10 is controlled by a number of voltage sources. For example, a DC voltage source 180 (VS1) supplies a number of DC voltages to the ion source region and to the first drift region, D1., and a radio frequency voltage source 190 (RF1) supplies a number of radio frequency (RF) voltages to the funnel and ion activation structure, F1/IA1. In the illustrated embodiment, the DC voltage source has a source needle output, SN, which is electrically connected to the needle 150 of the sample solution. A funnel 1 front lens output, F1F, is electrically connected to the first lens 164 of the funnel and ion activation structure, F1/IA1, to the electrospray ionizer 16 (and the capillary 152) and to the front wall 160 of the chamber 154. Alternatively, the first lens 164 may be biased differently than the ionizer 16, capillary 152 and front wall 160 to create an electric field between the end of the capillary 152 and the first lens 164 that may enhance or facilitate directing of ions from the capillary 152 into the funnel an ion activation structure, F1/IA1. In any case, a funnel 1 back lens output, F1B, is electrically connected to the last or back lens 166 of the funnel and ion activation structure, F1/IA1, a gate 1, G1, output is electrically connected to the gate lens 168, and a drift region 1 front lens output, D1F, is electrically connected to the first lens 170 of the first drift tube region, D1. The gate 1 output, G1, is also electrically connected to the programmable delay generator, PDG, illustrated in FIG. 1. The RF voltage source 190 is a conventional RF voltage source, and produces two RF voltages, $\phi_1$ and $\phi_2$. The RF voltage $\phi_1$ is supplied through series capacitors, C, to every other lens of the funnel and ion activation structure, F1/IA1, beginning with the first lens 164, and the RF voltage $\phi_2$ is supplied through series capacitors, C, to the remaining lenses of the funnel and ion activation structure, F1/IA1. The voltages $\phi_1$ and $\phi_2$ are, in the illustrated embodiment, 180 degrees out of phase with each other, and in one exemplary embodiment the RF voltage source 190 produces $\phi_1$ and $\phi_2$ voltages of 50-70 $V_{p-p}$ at 450 kHz, although the RF voltage source 190 may alternatively be configured to produce other voltages at other frequencies and/or with other phase relationships to suit alternate implementations of the IMS 10. In any case, a chain of resistors, $R_{RF}$, is connected across the funnel and ion activation structure, F1/IA1, with each resistor $R_{RF}$ being electrically connected between adjacent lenses of F1/IA1. The chain or resistors, R, connected across the drift tube sections $20_1$-$20_7$ as described hereinabove, begins with the first lens 170 of D1, and continues to the end of the drift tube section $20_7$ unless otherwise noted herein. In one exemplary embodiment, R=5 MΩ, 1%, $R_{RF}$=1

MΩ, 0.1% and C=1000 pF, 10%, although other values of these components may alternatively be used.

Figure 11:
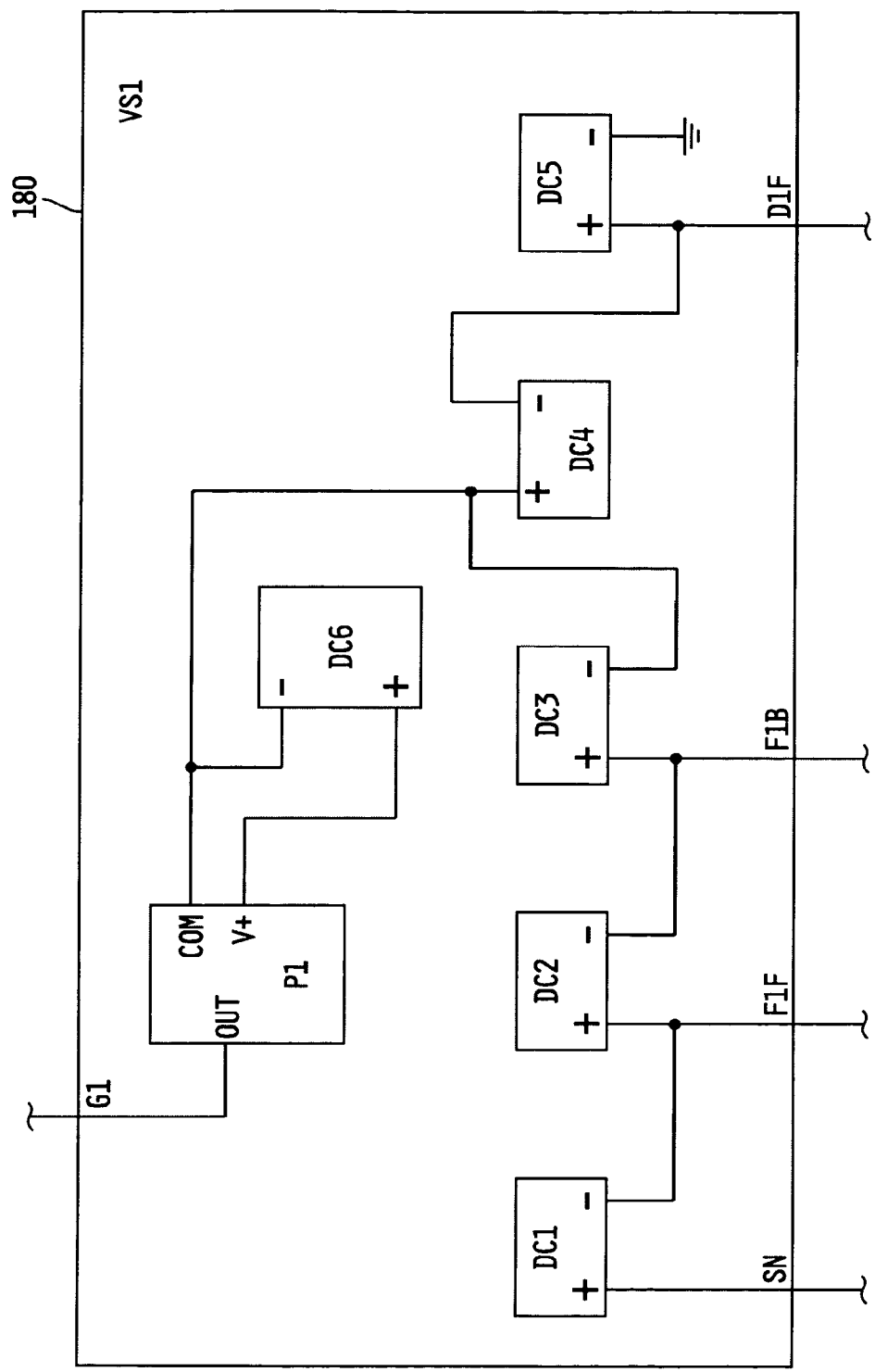
FIG. 11 is a block diagram of one illustrative embodiment of the DC voltage source, VS1, of FIG. 10.

Referring now to FIG. 11, one illustrative embodiment of the DC voltage source 180 (VS1) is shown. In the illustrated embodiment, the DC voltage source 180 includes a number of individual DC voltage sources and a voltage pulsing source. All such sources are conventional in their construction and operation. A first DC voltage source, DC1, has a positive output defining the sample needle voltage, SN, and a negative output electrically connected to the positive output of another DC voltage supply, DC2, and also defining the funnel 1 front lens output voltage, F1F. The negative output of DC2 is electrically connected to the positive output of another DC voltage supply, DC2, and this connection also defines the funnel 1 back lens output voltage, F1B. The negative output of DC3 is electrically connected to the positive output of another DC voltage supply, DC4, and the negative output of DC4 is electrically connected to the positive output of yet another DC voltage supply, DC5. This connection also defines the drift region front lens output voltage, D1F. The negative output of DC5 is connected to a ground or other reference potential. The positive output of DC4 is also electrically connected to a negative output of another DC voltage source, DC6, and to a common input, COM, of a voltage pulsing source, P1. The positive output of DC6 is electrically connected to a V+ input of P1, and the output, OUT, of P1 defines the gate 1 output voltage, G1. The following Table VI provides example voltage values and/or ranges typical for one specific implementation of the DC voltage source 180, although it will be understood that any one or more of the example values and/or ranges may be modified to suit alternate implementations of the IMS 10.

TABLE VI

| DC Voltage Source 180 | Voltage Values/Ranges |
|---|---|
| DC1 (SN) | 1.8-2.2 kvolts |
| DC2 (F1F) | 135-200 volts |
| DC3 (F1B) | 30-70 volts |
| DC4 | 15 volts typical |
| DC5 (D1F) | 2285 typical |
| DC6 | 60-110 volts |
| P1 (G1) | pulse between DC6 and DC4 |

The DC voltage source 180 and the RF voltage source 190 may be controlled to accomplish a number of operational goals. For example, DC voltage source 180 and the RF voltage source 190 may be controlled to collect and accumulate ions produced by the electrospray ionizer 16 in the funnel and ion activation region F1/IA1. To do this using the example DC source voltages illustrated in Table VI, i.e., with DC5=D1F=2285 volts, DC1 is controlled to produce a DC voltage at SN that is approximately 2.2 kvolts relative to D1F, DC3 is controlled to produce a DC voltage at F1B that is approximately 65 volts relative to D1F, DC2 is controlled to produce an electric field between the first lens 164 and the last lens 166 of the funnel and ion activation structure, F1/IA1, of approximately 11 volts/cm (typical), and DC6 and P1 are controlled to produce a DC voltage at G1 that is approximately 85 volts relative to D1F. When it is desirable to "gate" (e.g., inject or allow entrance of) ions accumulated in F1/IA1 into the first drift tube region, D1, P1 is controlled to drop the bias voltage, G1, on the gate lens 168 by approximately 60 volts; e.g., to 15 volts. Ion activation, as this term will be defined hereinafter, can also be made to selectively occur within F1/IA1 by suitably controlling the magnitude of the electric field within F1/IA1 via control of the amplitude of the RF voltage source 190 and/or one or more of the individual voltage sources of the DC voltage source 180.

Generally, the gate, G1, as well as any ion gate described herein, may be selectively controlled to accomplish any of a number of functions. For example, when it is desirable to allow ions transmit ions through the gate, G1, the voltage on the gate, G1, is held at its low potential. Conversely, when it is desirable to inhibit the flow of ions through the gate, G1, the voltage on the gate, G1, is held at its high potential. When it is desirable to selectively allow passage of ions through the gate, G1, the voltage on the gate, G1, is pulsed from its high potential to its low potential for a suitable duration. It will further be understood that the voltage and electric field values and/or ranges indicated above and herein are provided only by way of example, and that this disclosure contemplates other values and/or ranges of operation with respect to such parameters.

Figure 12:
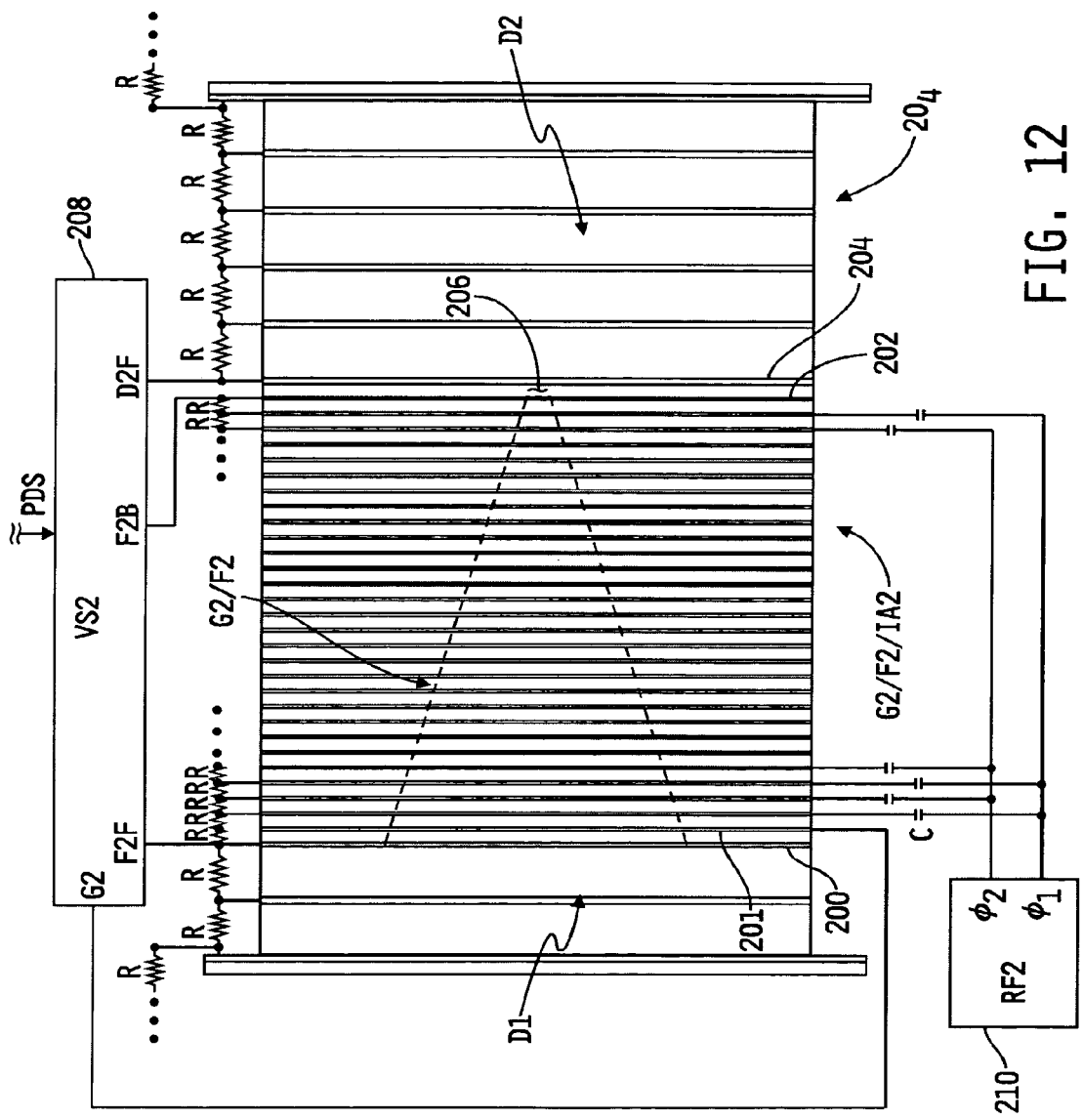
FIG. 12 is a magnified and detailed view of the drift tube section of the ion mobility spectrometer of FIG. 1 that contains the second gate, funnel and ion activation region.

Referring now to FIG. 12, one illustrative embodiment of the drift tube section $20_4$ is shown. The drift tube section $20_4$ contains the end of the first drift tube region, D1, the second ion gate, funnel and activation region, G2/F2/IA2 and the beginning of the second drift tube region, D2. The second ion gate, funnel and ion activation structure, G2/F2/IA2, is illustratively formed by compressing together a number of alternating electrically conductive and electrically insulating ring members, or lenses, similarly as described hereinabove with respect to FIGS. 2-9B. The resulting second ion gate and funnel, G2/F2 is generally defined between a first or front lens 200 and a last or back lens 202, and the second ion activation region 206 (IA2), is generally defined between the back lens 202 of the second gate and funnel, G2/F2, and the first or front lens 204 of the second drift tube region, D2.

The ion gate of the second ion gate and funnel, G2/F2, is defined by the first and second lenses 200, 201 and the electrically insulating ring member positioned between the lenses 200 and 201. The first and second lenses are each, e.g., 0.07 cm, thick, e.g., 14 cm outer diameter, and e.g., 7 cm inner diameter, annular stainless steel ring members, each having a grid attached thereto, and the electrically insulating ring member positioned between the lenses 200 and 201 is an annular, e.g., 0.32 cm, Delrin® acetal resin spacer.

The funnel structure of the second ion gate and funnel, G2/F2, is defined by a series of alternating electrically conductive ring members and electrically insulating ring members. In one exemplary embodiment, the funnel structure of the second ion gate and funnel, G2/F2, is formed by compressing together 31 concentric stainless steel electrodes, e.g., 0.07 cm thick and 14 cm outer diameter, that are each electrically isolated by Delrin® acetal resin ring members, e.g., 0.32 mm thick, each configured to receive, e.g., 0.24 cm, flexible O-rings on each side to provide a vacuum seal between all of the ring members. The 31 concentric stainless steel electrodes have inner diameters that decrease linearly from, e.g., 7 cm to 0.56 cm.

The drift tube section $20_4$ of FIG. 12 is controlled by a number of voltage sources. For example, a DC voltage source 208 (VS2) supplies a number of DC voltages to the first drift tube region, D1, the second ion gate and funnel, G2/F2, to the second ion activation region, 206, and to the second drift tube region, D2. A radio frequency voltage source 210 (RF2) supplies a number of radio frequency (RF) voltages to the second ion gate and funnel structure, G2/F2. In the illustrated embodiment, the DC voltage source 208 has a funnel 2 front lens output, F2F, that is electrically connected to the first lens 200 of the second ion gate and funnel structure, G2/F2, a gate 2 output, G2, that is electrically connected to the second lens 201 of the second ion gate and funnel structure, G2/F2, a funnel 2 back lens output, F2B, that is electrically connected to the last or back lens 202 of the second ion gate and funnel structure, G2/F2, and a second drift tube front lens output, D2F, that is electrically connected to the first or front lens 204 of the second drift tube region, D2. The DC voltage source 208 also has an input receiving a programmable delay signal, PDS, produced by the programmable delay generator, PDG (see FIG. 1). The RF voltage source 210 is a conventional RF voltage source, and produces two RF voltages, $\phi_1$ and $\phi_2$. The RF voltage $\phi_1$ is supplied through series capacitors, C, to every other lens of the second ion gate and funnel structure, G2/F2, and the RF voltage $\phi_2$ is supplied through series capacitors, C, to the remaining lenses of the second ion gate and funnel structure, G2/F2. Generally, the $\phi_1$ and $\phi_2$ voltages are applied to the second ion gate and funnel structure, G2/F2 beginning with the lens following the second gate lens 201 and ending with the lens positioned just prior to the last or back lens 202. As with the RF voltage source 190, the voltages $\phi_1$ and $\phi_2$ are, in the illustrated embodiment, 180 degrees out of phase with each other, and in one exemplary embodiment the RF voltage source 210 produces $\phi_1$ and $\phi_2$ voltages of approximately 100 $V_{p-p}$ at 480 kHz, although the RF voltage source 210 may alternatively be configured to produce other voltages at other frequencies and/or with other phase relationships to suit alternate implementations of the IMS 10. In any case, the chain of resistors, R, that is connected across the electrically conductive ring members of the first drift tube region, D1, is continued across each of the electrically conductive ring members of the second ion gate, funnel and ion activation region, G2/F2/IA2, and also across the electrically conductive ring members of the second drift tube region, D2, with two exceptions. Specifically, the second lens 201 of the second ion gate is skipped, i.e., not connected, in the resistor chain, and no resistor is connected across the second ion activation region 206, i.e., between the electrically conductive ring members 202 and 204. In one exemplary embodiment, R=5 M$\Omega$, 1%, as described hereinabove, and C=500 pF, 10%, although other values of these components may alternatively be used.

Figure 13:
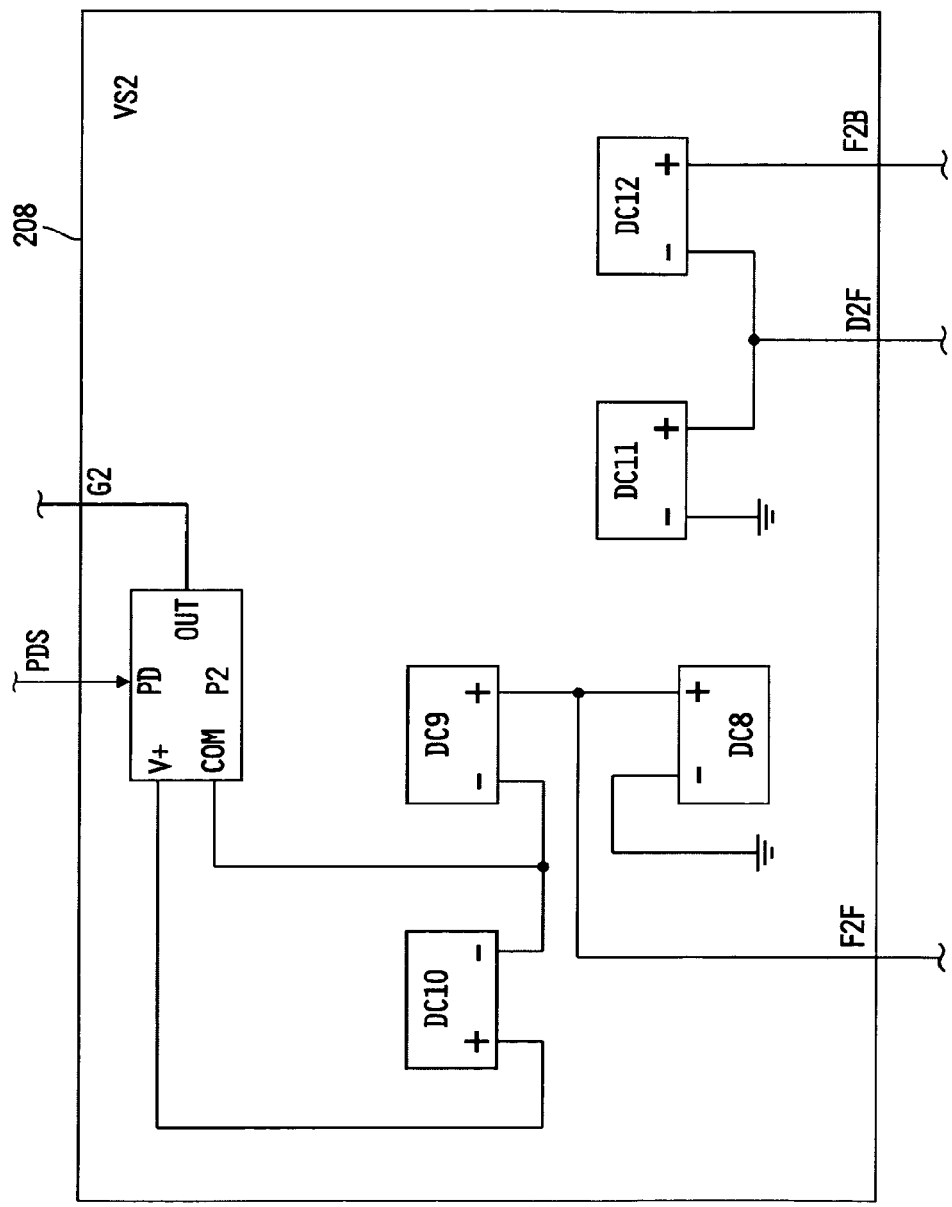
FIG. 13 is a block diagram of one illustrative embodiment of the DC voltage source, VS2, of FIG. 12.

Referring now to FIG. 13, one illustrative embodiment of the DC voltage source 208 (VS2) is shown. In the illustrated embodiment, the DC voltage source 208 includes a number of individual DC voltage sources and a voltage pulsing source. All such sources are conventional in their construction and operation. A first DC voltage source, DC8, has a positive output defining the funnel 2 front lens output, F2F, and a negative output electrically connected to a ground reference. Another voltage source, DC11, has a positive output that defines the second drift tube front lens voltage, D2F, and is also electrically connected to a negative output of yet another voltage source, DC12. The negative output of the voltage source, DC11, is electrically connected to the ground reference, and the positive output of the voltage source, DC12, defines the funnel 2 back lens voltage, F2B. The positive output of the voltage source DC8 is electrically connected to the positive output of another voltage source, DC9. The negative output of the voltage source, DC9, is electrically connected to the negative output of another voltage source, DC10, and also to a common input (COM) of a voltage pulsing source, P2. The pulse delay signal, PDS, supplied by the pulse delay generator, PDG, (see FIG. 1) is electrically connected to a pulse delay input, PD, of the voltage pulsing source, P2. The positive output of the voltage source DC10 is electrically connected to a V+ input of the voltage pulsing source P2, and the output, OUT, of the voltage pulsing source P2 defines the gate 2 output voltage, G2. The following Table VII provides example voltage values and/or ranges typical for one specific implementation of the DC voltage source 208, although it will be understood that any one or more of the example values and/or ranges may be modified to suit alternate implementations of the IMS 10.

TABLE VII

| DC Voltage Source 208 | Voltage Values/Ranges |
|---|---|
| DC8 (F2F) | 1240 volts typical |
| DC9 | 5-10 volts |
| DC10 | 20 volts typical |
| DC11 (D2F) | 1061 volts typical |
| DC12 (F2B) | 5-200 volts |
| P2 (G2) | pulse between 0 and −20 volts typical |

The DC voltage source 180 and the RF voltage source 190 may be controlled to accomplish a number of operational goals. For example, the DC voltage source, DC8, is controlled to maintain a desired electric field, e.g., approximately 12 volts/cm, through the first drift tube region, D1. Likewise, the DC voltage sources, DC8, DC9, DC10, DC11 and DC12 are controlled to maintain a desired electric field, e.g., approximately 14 volts/cm, through the second ion gate, funnel and ion activation region, G2/F2/IA2 under non-gating and non-ion activation operation. When it is desirable to "gate" (e.g., allow passage of) ions from the first drift tube region, D1, into the second drift tube region, D2, the voltage pulsing source P2 is responsive to the pulse delay signal, PDS, supplied by the pulse delay generator, PDG, to drop the bias voltage, G2, on the gate lens 201 by approximately 20 volts. The pulse delay generator, PDG, is, in the illustrated embodiment, a conventional programmable pulse generator, e.g., model DG535, Stanford Research Systems, Inc., that is responsive to pulsed activation of the first gate voltage, G1, to produce the pulse delay signal, PDS, after a programmable delay period. Via suitable choice of the delay period, ions having only a predefined mobility or range of mobilities may be passed from the first drift region, D1, to the second drift region, D2. Alternatively, the processor 32 may be programmed to control timing of the G2 pulse. In either case, this process of controlling the G2 to allow passage from D1 to D2 only of ions having a predefined mobility or range of mobilities may be referred to hereinafter as "mobility selection." Ion activation, as this term will be defined hereinafter, can be made to selectively occur within the second ion activation region 206 by suitably controlling the magnitude of the electric field within the region 206 via control of the amplitude of the DC voltage source, DC 12, relative to the amplitude of the DC voltage source, DC11. In this embodiment, the electrically conductive ring member 204 that defines the first lens of the second ion drift region, D2, contains a grid to prevent RF fields, resulting from the RF voltages produced by the RF voltage source 210, from extending into the second drift tube region, D2. It will be appreciated that the RF voltage source 210 and/or another suitable RF voltage source may alternatively be electrically connected across the ion activation region 206 to create an RF electric field within the ion activation region 206 that is suitable for ion activation, as this term will be described hereinafter. It will also be appreciated that the second ion gate, 200, 201, may alternatively be positioned at or near the end of the second funnel region, e.g., at or near the last or back lens 202 of the second funnel structure.

Referring now to FIG. 14, one illustrative embodiment of the drift tube section $20_7$ is shown. The drift tube section $20_7$ contains the end of the second drift tube region, D2, and the third funnel structure, F3. The third activation region, IA3, is mounted to the ion outlet end of the third funnel structure, F3.

The third funnel structure, F3, is illustratively formed in the same manner as G2/F2/IA2, i.e., by compressing together a number of alternating electrically conductive and electrically insulating ring members, or lenses, similarly as described hereinabove with respect to FIGS. 2-9B. The resulting third funnel structure, F3, is generally defined between a first or front lens 220 and a last or back lens 222, and in one exemplary embodiment the third funnel structure, F3, is formed by compressing together 31 concentric stainless steel electrodes, e.g., 0.07 cm thick and 14 cm outer diameter, that are each electrically isolated by Delrin® acetal resin ring members, e.g., 0.32 mm thick, each configured to receive, e.g., 0.24 cm, flexible O-rings on each side to provide a vacuum seal between all of the ring members. The 31 concentric stainless steel electrodes have inner diameters that decrease linearly from, e.g., 7 cm to 0.56 cm. The front lens 220 and the last or back lens 222 are covered by a grid, e.g., 90% ion transmittance, to prevent RF fields within F3 to extend into the third ion activation region, IA3.

The second drift tube region, D2, and the third funnel structure, F3, are controlled by a number of voltage sources. For example, a DC voltage source 224 (VS3) supplies a number of DC voltages to the D2 and F3 regions, and a radio frequency voltage source 226 (RF3) supplies a number of radio frequency (RF) voltages to the third ion funnel structure, F3. In the illustrated embodiment, the DC voltage source 224 has a funnel 3 front lens output, F3F, which is electrically connected to the first lens 220 of the third funnel structure, F3, which is also the last or back lens of the second ion drift region, D2. A funnel 3 back lens output, F3B, is electrically connected to the last or back lens 222 of the third funnel structure, F3. The RF voltage source 226 is a conventional RF voltage source, and produces two RF voltages, $\phi_1$ and $\phi_2$. The RF voltage $\phi_1$ is supplied through series capacitors, C, to every other lens of the third funnel structure, F3, and the RF voltage $\phi_2$ is supplied through series capacitors, C, to the remaining lenses of the third funnel structure, F3. Generally, the $\phi_1$ and $\phi_2$ voltages are applied to the third funnel structure, F3 beginning with the first or front lens 220 and ending with the lens prior to the last or back lens 222. As with the RF voltage sources 190 and 210, the voltages $\phi_1$ and $\phi_2$ are, in the illustrated embodiment, 180 degrees out of phase with each other, and in one exemplary embodiment the RF voltage source 226 produces $\phi_1$ and $\phi_2$ voltages of approximately 70 $V_{p-p}$ at 450 kHz although the RF voltage source 226 may alternatively be configured to produce other voltages at other frequencies and/or with other phase relationships to suit alternate implementations of the IMS 10. In any case, the chain of resistors, R, that is connected across the electrically conductive ring members of the first and second drift tube regions, D1 and D2, is continued across each of the electrically conductive ring members of the third ion funnel structure, F3. In one exemplary embodiment, R=5 MΩ, 1%, as described hereinabove, and C=500 pF, 10%, although other values of these components may alternatively be used.

Figure 15:
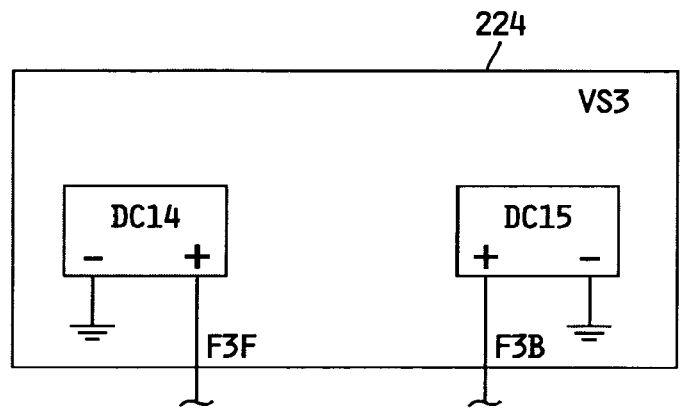
FIG. 15 is a block diagram of one illustrative embodiment of the DC voltage source, VS3, of FIG. 14.

Referring now to FIG. 15, one illustrative embodiment of the DC voltage source 224 (VS3) is shown. In the illustrated embodiment, the DC voltage source 224 includes two individual DC voltage sources, which are conventional in their construction and operation. A first DC voltage source, DC14, has a positive output defining the funnel 3 front lens output, F3F, and a negative output electrically connected to a ground reference. The second DC voltage source, DC15, has a positive output defining the funnel 3 back lens output, F3B, and a negative output electrically connected to the ground reference. The following Table VIII provides example voltage values and/or ranges typical for one specific implementation of the DC voltage source 224, although it will be understood that any one or more of the example values and/or ranges may be modified to suit alternate implementations of the IMS 10.

TABLE VIII

| DC Voltage Source 224 | Voltage Values/Ranges |
| --- | --- |
| DC14 (F3F) | 237.5 volts typical |
| DC15 (F3B) | 22.5 volts typical |

The DC voltage source 224 and the RF voltage source 226 may be controlled to accomplish a number of operational goals. For example, the DC voltage source, DC14, is controlled to maintain a desired electric field, e.g., approximately 12 volts/cm, through the second drift tube region, D2. Likewise, the DC voltage sources, DC14 and DC15 are controlled to maintain a desired electric field, e.g., approximately 17.5 volts/cm, through the third ion funnel structure, F3. The RF voltage source 226 is controlled to focus ions through the third funnel structure, F3, with maximum ion throughput. It will also be appreciated that although the third funnel structure, F3, is not shown or described as including an associated third ion gate structure, the third funnel structure, F3, may alternatively be modified to include such a third ion gate structure. Such a third ion gate structure may be identical or similar to the second ion gate, 200, 201 described hereinabove with respect to FIG. 12, or may alternatively be positioned at or near the end of the third funnel structure, e.g., at or near the last or back lens 222 of the third funnel structure, F3. In any case, such a third ion gate could be operated similarly to the second ion gate in that another programmable delay generator could be electrically connected between the gate 2 output, G2, of the DC voltage source 210 (VS2) and another voltage pulsing source contained within the DC voltage source 224. Via suitable programming of this second programmable delay generator, the third ion gate could be controlled to allow passage out of the second drift tube region, D2, only ions having a predefined mobility or mobility range. Alternatively, the processor 32 could control the timing of control of the third ion gate. In either case, mobility selection could therefore take place not only at the second ion gate, but also at the third if such a third ion gate is provided.

A conventional split-field region is mounted to the end of the second drift tube, D1, and has a conical lens 230 centered over the last lens 222 of the third funnel structure, F3, with the larger, ion inlet end of the conical lens 230 positioned adjacent to the lens 222. A beryllium-copper (BeCu) lens 232 is positioned at the smaller, ion outlet end of the conical lens 230, and a skimmer cone 234 has its smaller, ion inlet end positioned adjacent to the BeCu lens 232 and its larger, ion outlet end opening away from the funnel structure, F3. The third ion activation region, IA3, is defined between the last lens 222 of the third funnel structure, F3, and the BeCu lens 232, and labeled in FIG. 14 as the region 228. The vacuum lines 49 and the buffer gas line 46 illustratively mate with the split-field region as illustrated in FIG. 14. The gas conduit 46 allows a buffer gas, e.g., GAS1 or GAS2, or a mixture of a buffer gas and a doping gas, e.g., GAS1 and GAS2, to enter and fill the cavity of the IMS 10 formed by the drift tube sections $20_1$-$20_7$.

Figure 16:
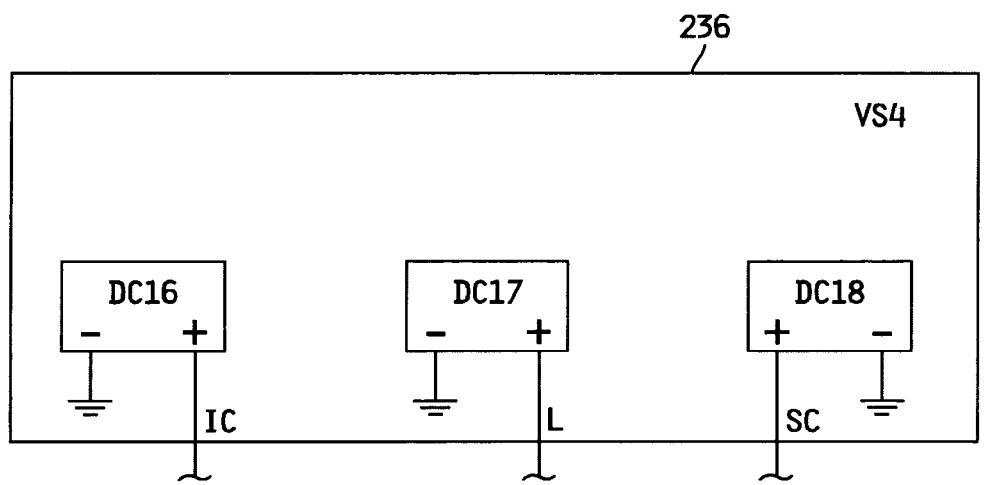
FIG. 16 is a block diagram of one illustrative embodiment of the DC voltage source, VS4, of FIG. 14.

A number of voltages produced by another voltage source 236 (VS4) are used to control operation of the split-field region. Referring to FIG. 16, one illustrative embodiment of the DC voltage source 236 (VS4) is shown. In the illustrated embodiment, the DC voltage source 236 includes three individual DC voltage sources, which are conventional in their construction and operation. A first DC voltage source, DC16, has a positive output defining an inverted cone voltage, IC, which is supplied to the conical lens 230, and a negative output electrically connected to a ground reference. A second DC voltage source, DC17, has a positive output defining a lens voltage, L, that is supplied to the BeCU lens 232, and a negative output electrically connected to the ground reference. The third DC voltage source, DC18, has a positive output defining a skimmer cone voltage, SC, that is supplied to the skimmer cone 234, and a negative output electrically connected to the ground reference. The following Table IX provides example voltage values and/or ranges typical for one specific implementation of the DC voltage source 236, although it will be understood that any one or more of the example values and/or ranges may be modified to suit alternate implementations of the IMS 10.

TABLE IX

| DC Voltage Source 236 | Voltage Values (NACT) | Voltage Ranges (ACT) |
|---|---|---|
| DC16 (IC) | 22.5-250 volts | 1-10 V < DC15 |
| DC17 (L) | 14.8-194.8 volts | 1-300 V < DC16 |
| DC18 (SC) | 14.5 volts | 5-20 V < DC17 |

Ion activation, as this term will be defined hereinafter, can be made to selectively occur within the third ion activation region, IA3, by suitably controlling the magnitude of the electric field within the region 228 via control of the amplitudes of the DC voltage sources DC15 (VS3) and DC16 (VS4). Generally, example voltage values of DC16-DC18 for non-ion activation conditions (NACT) are illustrated in the middle column of Table IX. Example voltage values of these sources for ion activation conditions (ACT) are, in contrast, illustrated in the right-most column of Table IX, in the illustrated embodiment, may be controlled to selectively induce ion activation, as this term will be described hereinafter, within the third ion activation region, IA3.

The exemplary dimensional information, electrical component value information and voltage source information set forth in Tables I-IX and accompanying text above refers to a two-stage IMS 10, i.e., an IMS having two drift tube regions D1 and D2. The two-stages of the IMS 10, i.e., the two drift tube regions D1 and D2, are separated by a gate, funnel and ion activation region, G2/F2/IA2 with a funnel, ion activation and gate region, F1/IA1/G1 supplying ions to the first drift tube region, D1, and with another funnel, F3, and ion activation region, IA3, positioned adjacent to the ion outlet of the IMS 10. The lengths of these various regions of the IMS 10 in this exemplary embodiment are summarized in Table X below, although it will be understood that any one or more of the example lengths may be modified to suit alternate implementations of the IMS 10.

TABLE X

| Region of IMS 10 | Length |
|---|---|
| D1 | 87.1 cm |
| G2/F2/IA2 | 12.7 cm |
| D2 | 68.7 cm |
| F3 | 12.24 cm |

The foregoing structure of the IMS 10 provides for a continuous-cavity IMS 10 that allows the entire instrument 10 to be filled with a buffer gas or mixture of gases. It will be understood, however, that the IMS 10 may alternatively be configured to operate the drift tube regions, D1 and D2, with different buffer gases or gas mixtures and/or to operate the drift tube regions, D1 and D2, at different pressures, and modifications to the IMS 10 to accomplish either of both of these goals would be a mechanical step for a skilled artisan. The structure of the IMS 10 is also scalable, making it possible to add or remove additional funnel/drift tube/ion activation assemblies, creating, for example, a system of multiple drift tube regions in series.

The ion funnels, F1, F2 and F3, provide for radial focusing of the ions to thereby allow high ion transmission through long drift tube regions. Generally, when the DC field in the funnel is at or above the field used in the adjacent drift tube regions, D1 and D2, high resolution mobility separations can be obtained. Simulations of ion tragectories, utilizing a three-dimensional field array, have been conducted and generally demonstrate that as ions travel through a drift tube, e.g., D1 or D2, they diffuse radially outwardly into a sizeable cloud. When such ion clouds pass through a funnel structure of the type illustrated and described herein, e.g., F1, F2 and F3, the diffuse clouds collapse radially inwardly and are transmitted efficiently into the next drift tube region. The simulations also indicate that if the DC fields in the funnel structures, F1, F2 or F3, are higher than in the adjacent drift tube regions, D1 and D2, it is possible to transmit nearly 100% of the ions through the funnel structures, F1, F2 or F3. Alternatively, if the DC fields in the funnel structures, F1, F2 or F3, is below a critical value, ions become increasingly trapped in the funnels. This latter feature makes possible additional operational modes of the IMS 10. For example, combined with a gate that is located at the ion entrance end of a funnel, e.g., the second ion gate and second funnel structure G2/F2 illustrated and described herein, either of the funnel structures, F2 or F3, may be used to trap and therefore accumulate mobility-selected ions from multiple ion packets.

The term "ion activation" has been used herein to identify a process that may be made to selectively occur within any of the ion activation regions, IA1, IA2 and/or IA3. As used herein, "ion activation" is the process of inducing structural changes in at least some ions resulting from collisions of the ions with the buffer gas or gas mixture in the presence of a high electric field. The high electric field may be an AC electric field, as is the case in IA1 as described hereinabove with respect to FIGS. 10 and 11, and/or may be a high DC electric field, as is the case in IA2 and IA3 as described hereinabove with respect to FIGS. 12-16. In any case, the induced structural changes in the ions may take either of two forms. In the presence of sufficiently high electric fields, high energy collisions of ions with the buffer gas or gas mixture result in fragmentation of at least some of the ions, and ion activation under sufficiently high electric field conditions thus corresponds to ion fragmentation. In the presence of elevated electric fields that are not sufficiently high to result in ion fragmentation, collisions of ions with the buffer gas or gas mixture result in conformational changes, i.e., changes in the shape, of at least some of the ions. Ion activation, under electric field conditions that are sufficiently high but not high enough to result in ion fragmentation, thus corresponds to ion conformational changes. In either case, the structural changes induced in at least some of the ions results in different ion mobilities and/or mass-to-charge ratios, which can be discerned when the structurally changed ions pass through a subsequent drift tube region and/or mass spectrometer.

It will be appreciated that the various voltage sources, VS1-VS4 and RF1-RF3, may be controlled to accomplish various goals within the different regions of the illustrated embodiment of the IMS 10. For example, the various voltage sources, VS1-VS4 and RF1-RF3, may be controlled to selectively gate (allow entrance of) ions from the ion source into D1, to selectively induce ion activation within the first funnel and ion activation region, F1/IA1, to selectively gate ions having only a predefined ion mobility or mobility range from D1 into D2, to selectively induce ion activation between D1 and D2, and/or to selectively induce ion activation between D2 and the ion detector 30 (and also between D2 and the mass spectrometer 12). Referring now to FIGS. 17A-17D, examples of four specific operational modes of the IMS 10 are provided, although it will be understood that other operational modes are possible with the IMS 10 as just described.

Figure 17A:
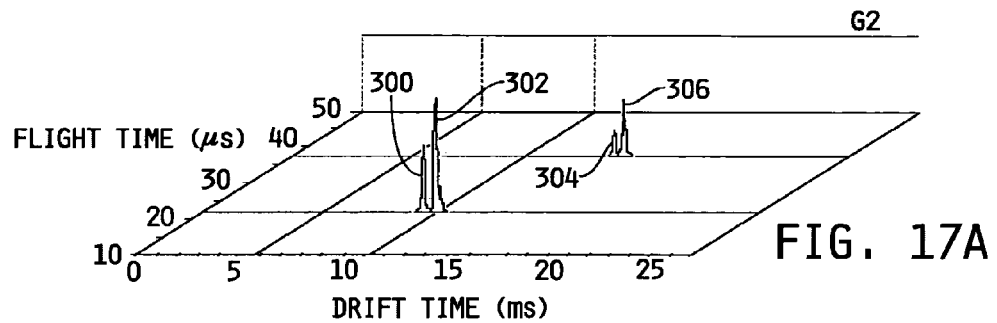
FIG. 17A is a plot of ion drift time vs. ion flight time illustrating one illustrative operational mode of the combination ion mobility spectrometer and mass spectrometer of FIG. 1.

Operational Mode A: measurement of standard nested IMS-MS distributions. Operational mode A of the IMS 10 involves acquisition of nested IMS-MS data, and is illustrated in FIG. 17A. In this mode of operation, ions are electrosprayed into the source region 18 of the IMS 10 via the electrospray ionizer 16, and enter the first funnel and ion activation region, F1/IA1, where they are accumulated. Illustratively, accumulation times may vary from, e.g., 20 to 200 ms. The RF voltage 190 is controlled to focus the accumulated ions, but not to induce ion activation. The voltage pulsing source, P1, is then controlled to deliver short, e.g., 50-100 μs, pulses to the first gate lens 168 to thereby gate (allow entrance of) ions into the first drift tube region, D1. Ion accumulation within, and release from, F1/IA1 is accomplished by raising and lowering the G1 voltage with respect to the drift voltage applied to the first lens 170 of the first drift tube region, D1. The same pulse used on the first gate lens 168 to gate ions into D1 also activates a synchronized voltage pulsing source (not shown) associated with the mass spectrometer 12. As the ion mixture drifts through D1, individual ion components separate in time based on differences in their mobilities. Also, as described hereinabove, the mixture of ions is radially focused as it passes through the funnel structures F2 and F3. Ions that exit the second drift tube region, D2, are focused by the third funnel, F3 into the mass spectrometer 12. In the example shown in FIG. 17A, the result is a conventional nested drift time and time-of-flight dataset having four discernible peaks, 300, 302, 304 and 306. This operational mode may be used for several purposes including, but not limited to, determining the drift times of ions in each drift tube region, D1 and D2, determining the delay time for subsequent ion mobility selection, and determining collision cross sections for precursor ions.

Operational Mode B: selection of a predefined ion mobility or range of ion mobilities. By selectively applying a synchronized delay pulse 308 to G2, as shown by example in FIG. 17B, it is possible to transmit only ions with a specific mobility or range of mobilities from the first drift tube region, D1, into the second drift tube region, D2. With a suitable delay between the pulses applied to G1 and to G2, FIG. 17B demonstrates selection of ions having mobilities around the peak 302 of FIG. 17A. In such cases where only a single ion structure is present the resultant drift time and time-of-flight distribution will contain only a single narrow peak, e.g., peak 302. However, if more than one component is present, it is possible that the mobility-selected ions may separate again in D2. This would be the case, for example, if a distribution of structures was selected that was interconverting slowly (i.e. on the timescales of the measurement). It is also possible that features that are in D1 may be resolvable upon separation in D2. The resolution differences between D1 and D2 can be enhanced by varying the lengths of D1 and D2. For example, a drift region in D2 that is four times longer than the drift region of D1 should have twice the resolving power (assuming identical drift tube fields). On the other hand, a high resolution selection could be obtained by using a D1 region that is much longer than D2.

Figure 17B:
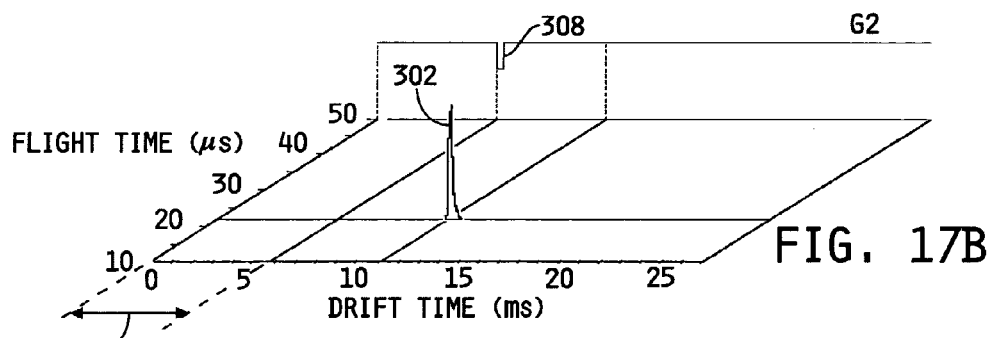
FIG. 17B is a plot of ion drift time vs. ion flight time illustrating another illustrative operational mode of the combination ion mobility spectrometer and mass spectrometer of FIG. 1.
Figure 17C:
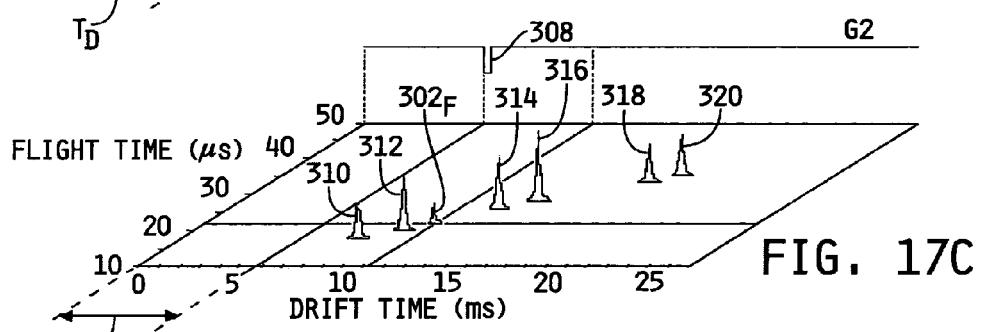
FIG. 17C is a plot of ion drift time vs. ion flight time illustrating yet another illustrative operational mode of the combination ion mobility spectrometer and mass spectrometer of FIG. 1.

Operational Mode C: activation of mobility-selected ions. As noted hereinabove, ion activation may be induced in the ion activation region, IA2. Ions are activated in this region by increasing the voltage between the two drift ring members 202 and 204 that make up IA2. As ions accelerate in this region, they gain energy through collisions with the buffer gas or gas mixture. The ion activation process appears to be highly tunable and reproducible, and under high-energy, e.g. suitably high electric field, conditions it is possible to induce extensive ion fragmentation as illustrated in FIG. 17C. Alternatively, the IA2 region can be operated under relatively low-energy activation conditions that induce a conformational changes in the ions without causing fragmentation, as described hereinabove. A hypothetical distribution illustrating this operational mode under high-energy conditions is shown in FIG. 17C, where the mobility-selected ion distribution 302 has been fragmented into fragment ion components $302_F$, and 310-320. The fragmented ion component $302_F$ represents what it left of the original ion distribution 302 after fragmentation, and the fragment ion components 310-320 represent the various fragments of the original ion distribution 302. Generally, the various fragment components 310-320 from multiply charge precursor ions may have ion mobilities and/or ion mass-to-charge ratios that are different than those of the original ion distribution 302. Subsequent separation in the second drift tube region, D2, and in the mass spectrometer 12 allow the fragments to be discriminated in the resultant drift time and time-of-flight distribution. New conformations that are produced at low-activation energies may also have ion mobilities and/or ion mass-to-charge ratios that are different than those of the original ion distribution 302. Those having higher ion mobilities correspond to ions that have become more compact (e.g., an unfolded structure that collapses) upon activation, and those having lower ion mobilities correspond to ions that have larger cross sections (e.g., folded states that upon activation unfold) upon activation.

Figure 17D:
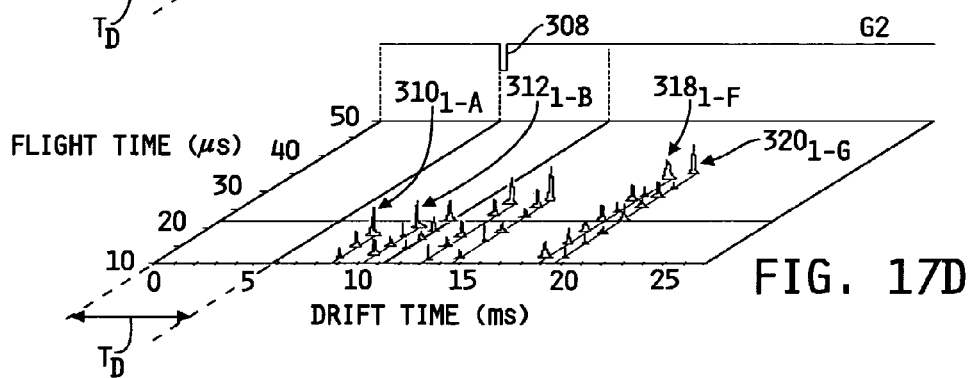
FIG. 17D is a plot of ion drift time vs. ion flight time illustrating a further illustrative operational mode of the combination ion mobility spectrometer and mass spectrometer of FIG. 1.

Operational Mode D: parallel dissociation of fragment ions that were formed from mobility-selected precursors. As noted hereinabove, ion activation may also be induced in the ion activation region, IA3, and this may be selectively carried out with or without prior mobility selection via control of G2 and/or ion activation in the ion activation regions IA1 and/or IA2. A hypothetical distribution illustrating this operational mode under high-energy conditions in IA3 is shown in FIG. 17D, where the mobility-selected ion distribution 302 has been fragmented in IA2 into fragment ion components $302_F$, and 310-320, and the ion fragments $302_F$ and 310-310 have been further fragmented in IA3 into ion fragment sets $310_{1-A}$, $312_{1-B}$, ... $318_{1-F}$, $320_{1-G}$. In this case, fragments that are generated at IA3 are not further separated in time as a function of ion mobility, and fragments generated from a common precursor therefore have identical drift times. However, since the fragment ions generated at IA3 do subsequently pass through the mass spectrometer 12, the fragment ions $310_{1-A}$, $312_{1-B}$, ... $318_{1-F}$, $320_{1-G}$ are separated in time as a function of ion mass-to-charge ratio. This operational mode may accordingly be referred to as parallel collision induced dissociation or some form thereof.

Figure 18:
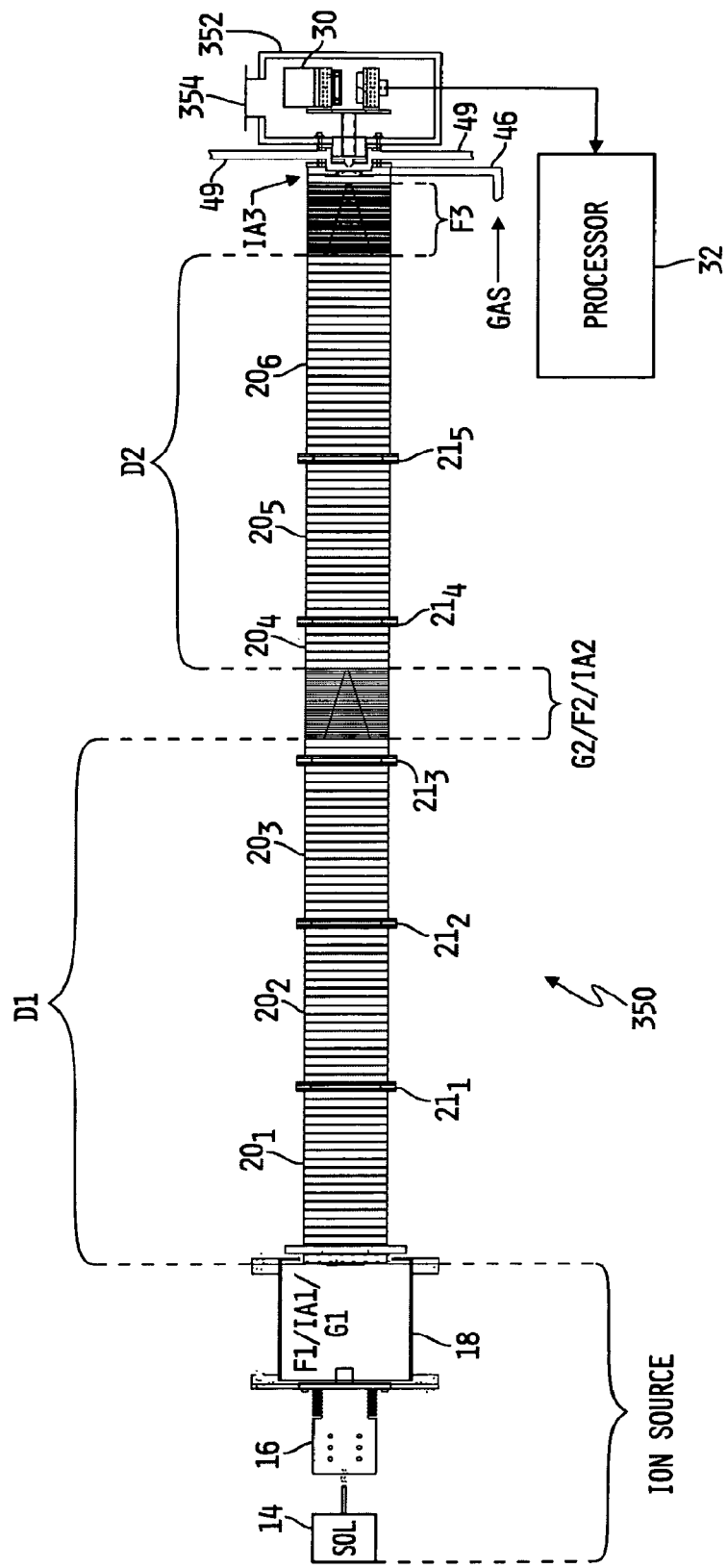
FIG. 18 is a diagrammatic illustration of a stand alone embodiment of the ion mobility spectrometer of FIG. 1.

As briefly described hereinabove with respect to FIG. 1, the present disclosure contemplates embodiments of the IMS 10 that do not include the mass spectrometer 12. An illustrative embodiment of one such ion mobility spectrometer (IMS) 350 is shown in FIG. 18. The IMS 350 illustrated in FIG. 18 is identical in many respects to the IMS 10 illustrated and described herein with respect to FIGS. 1-17D, and like numbers and alphanumeric identifiers are used to identify like components. Like the IMS 10, the IMS 350 includes an ion source, followed by a first ion drift tube region, D1, followed by a gate, funnel and ion activation region, G2/F2/IA2, followed by a second ion drift tube region, D2, followed by another funnel, F3, and an ion activation region, IA3. The ion outlet of the ion activation region IA3 is coupled to a vacuum chamber 352, and a conventional vacuum pump 354 is used to control the vacuum level within the chamber 352 and, in turn, within the IMS 350. The ion detector 30 resides within the vacuum chamber 352, and is electrically connected to the processor 32 as previously described. The gas passageway or conduit 46 may receive a buffer gas or other gas mixture via one or more suitable gas sources such as illustrated in FIG. 1, although such structure is omitted from FIG. 18 for clarity of illustration. It will be understood that the IMS 350 further includes a number of DC and RF voltage source configured to control operation thereof as described hereinabove, although such structure is likewise omitted from FIG. 18 for clarity of illustration. The IMS 350 is operable as described hereinabove with respect to the IMS 10, with the exception that the ion spectral information produced by the processor 32 will necessarily be in one dimension only, i.e., ion drift time, since the instrument depicted in FIG. 18 does not include a mass spectrometer or other ion separation instrument. In this regard, drift time vs. ion intensity plots 400, 402 and 404 are illustrated in FIG. 19 for the three operational modes, A, B and C respectively, of the instrument depicted in FIG. 1 that are illustrated in FIGS. 17A, 17B and 17C respectively.

Figure 19:
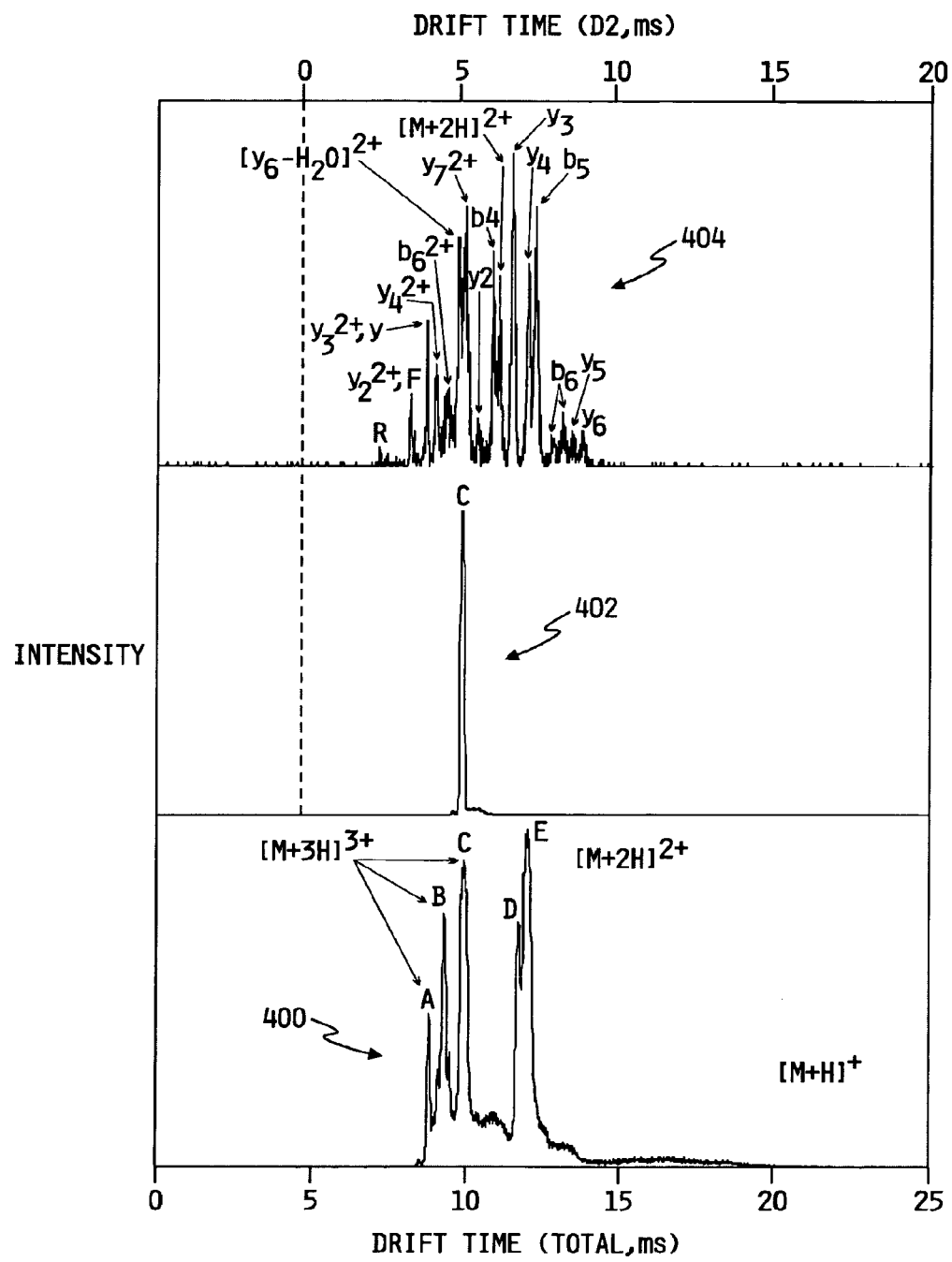
FIG. 19 includes a series of plots of drift time vs. intensity illustrating operation of the ion mobility spectrometer of FIG. 18 under the same operational modes of the combination ion mobility spectrometer and mass spectrometer of FIG. 1 that were illustrated in FIGS. 17A-17C.

The ion intensity plot 400 of FIG. 19 illustrates IMS data for operational mode "A" shown in FIG. 17A and described hereinabove. In this mode of operation, ions are electrosprayed into the source region 18 of the IMS 350 via the electrospray ionizer 16, and enter the first funnel and ion activation region, F1/IA1, where they are accumulated. The RF voltage 190 is controlled to focus the accumulated ions, but not to induce ion activation. The voltage pulsing source, P1, is then controlled to deliver short pulses to the first gate lens 168 to thereby gate (allow entrance of) ions into the first drift tube region, D1. Ion accumulation within, and release from, F1/IA1 is accomplished by raising and lowering the G1 voltage with respect to the drift voltage applied to the first lens 170 of the first drift tube region, D1. As the ion mixture drifts through D1, individual ion components separate in time based on differences in their mobilities. Also, as described hereinabove, the mixture of ions is radially focused as it passes through the funnel structures F2 and F3. Ions that exit the second drift tube region, D2, are focused by the third funnel, F3 into the mass spectrometer 12. The resulting spectrum 400 contains a number of ion mobility peaks, A-E.

The ion intensity plot 402 of FIG. 19 illustrates IMS data for operational mode "B" shown in FIG. 17B and described hereinabove. As previously described, a synchronized delay pulse may be selectively applied to G2 to transmit only ions with a specific mobility or range of mobilities from the first drift tube region, D1, into the second drift tube region, D2. In the illustrated example, the delay was chosen to select ions having mobilities around the peak "C", and the resulting spectrum 402 therefore contains only the single narrow peak, e.g., peak "C."

The ion intensity plot 404 of FIG. 19 illustrates IMS data for operational mode "C" shown in FIG. 17C and described hereinabove. As previously described, the ion activation region, IA2, may be controlled to induce ion fragmentation. In the illustrated example, ions having mobilities around the peak "C" were selected, as described in mode "B" above, and these selected ions were then fragmented in IA2. As the fragmented ions drift through the second ion drift region, D2, the fragments separate according to their ion mobilities. In the illustrated example, the resulting spectrum 404 therefore contains discernible drift times of the various fragments of the mobility-selected ions that were fragmented in IA2. While the ion mobility instrument 350 illustrated in FIG. 18 is capable of operation according to operational mode "D" illustrated and described herein, a plot of this mode is not included in FIG. 19 since ions fragmented in IA3 would not be discernible in a one-dimensional drift time plot because such fragmented ions have no further opportunity to separate in the instrument 350.

Figure 20A:
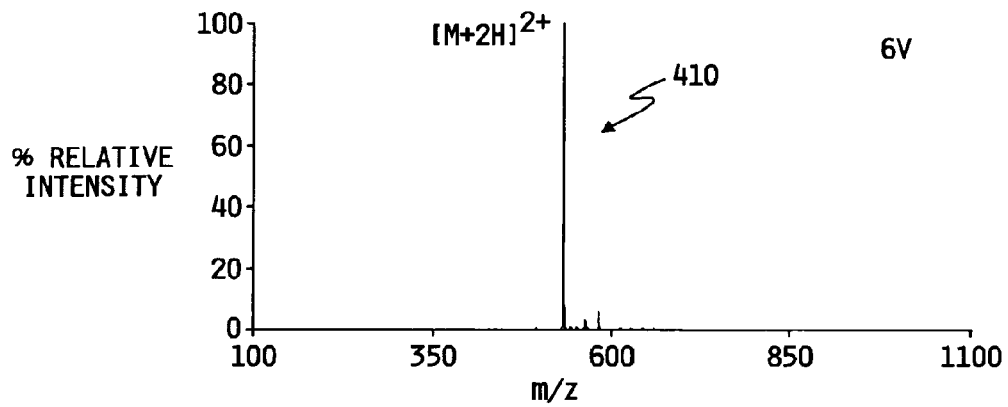
FIG. 20A is a plot of mass-to-charge ratio vs. ion intensity illustrating fragmentation of a $[M+2H]^{2+}$ peptide ion, under one set of electric field conditions, in the second ion activation region of the ion mobility spectrometer of FIG. 1.
Figure 20B:
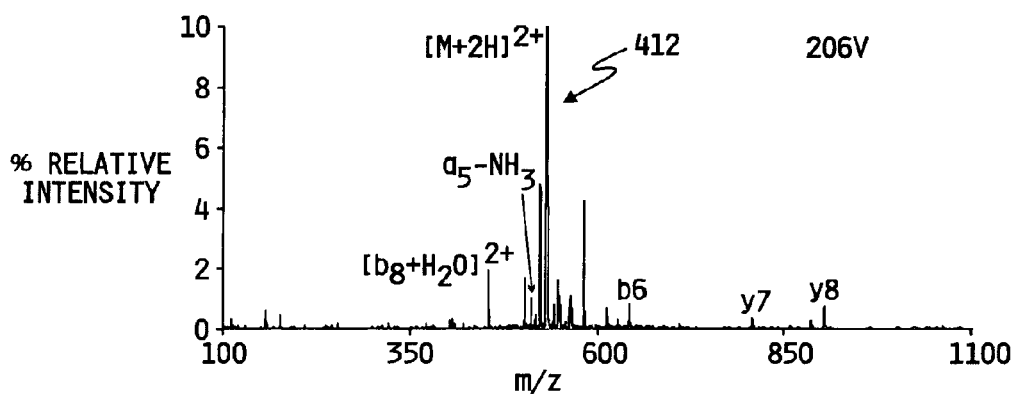
FIG. 20B is a plot of mass-to-charge ratio vs. ion intensity illustrating fragmentation of a $[M+2H]^{2+}$ peptide ion, under another set of electric field conditions, in the second ion activation region of the ion mobility spectrometer of FIG. 1.
Figure 20C:
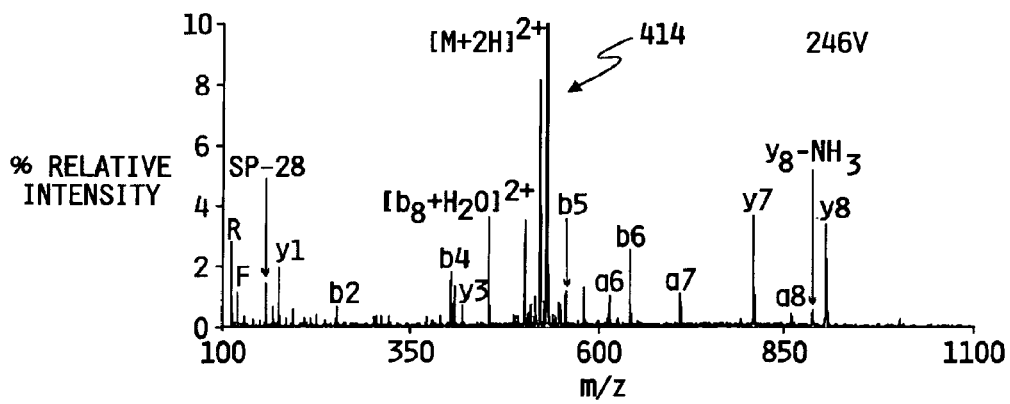
FIG. 20C is a plot of mass-to-charge ratio vs. ion intensity illustrating fragmentation of a [M+2H]$^{2+}$ peptide ion, under yet another set of electric field conditions, in the second ion activation region of the ion mobility spectrometer of FIG. 1.
Figure 20D:
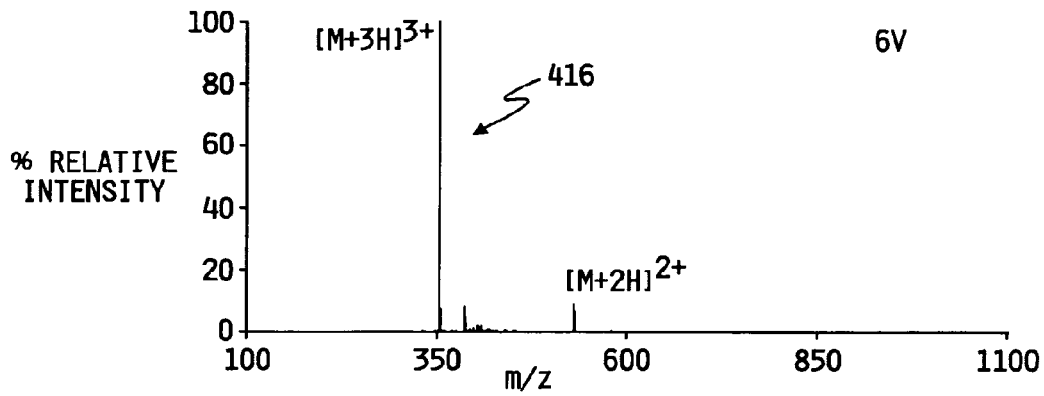
FIG. 20D is a plot of mass-to-charge ratio vs. ion intensity illustrating fragmentation of a [M+3H]$^{3+}$ peptide ion, under one set of electric field conditions, in the second ion activation region of the ion mobility spectrometer of FIG. 1.
Figure 20E:
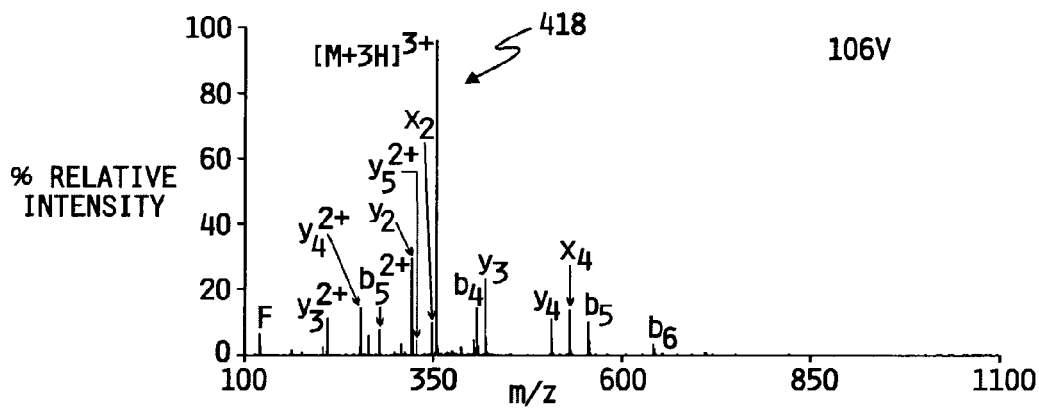
FIG. 20E is a plot of mass-to-charge ratio vs. ion intensity illustrating fragmentation of a [M+3H]$^{3+}$ peptide ion, under another set of electric field conditions, in the second ion activation region of the ion mobility spectrometer of FIG. 1.
Figure 20F:
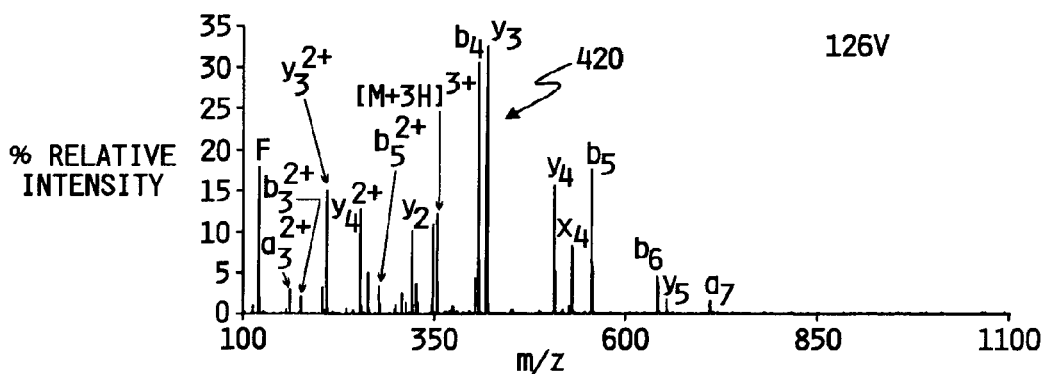
FIG. 20F is a plot of mass-to-charge ratio vs. ion intensity illustrating fragmentation of a [M+3H]$^{3+}$ peptide ion, under yet another set of electric field conditions, in the second ion activation region of the ion mobility spectrometer of FIG. 1.

It has been described hereinabove with respect to FIGS. 12 and 13, and with respect to at least some of the various example operational modes of the IMS 10 and 350, that ion activation may be selectively induced in any of the ion activation regions IA1, IA2 and IA3. By way of example, FIGS. 20A-20F show mass spectra for several different electric field conditions that have been experimentally used to activate $[M+2H]^{2+}$ and $[M+3H]^{3+}$ ions in the second ion activation region 206 (IA2) of the IMS 10. In general, higher-charge state ions can be activated at lower electric fields within IA2 206, a result that can be explained by considering that the activation energy scales with the charge state. The degree of fragmentation for ions of any charge state can be tuned over a substantial range, as illustrated in FIGS. 20A-20F. FIG. 20A, for example, illustrates a mass spectra 410 for $[M+2H]^{2+}$ ions exposed to an electric field within the ion activation region 206 (FIG. 12) established by a voltage differential between the electrically conductive ring members 202 and 204 of approximately 6.0 volts. FIG. 20B illustrates a mass spectra 412 for $[M+2H]^{2+}$ ions exposed to an electric field within the ion activation region 206 established by a voltage differential between the electrically conductive ring members 202 and 204 of approximately 206 volts, and FIG. 20C illustrates a mass spectra 414 for $[M+2H]^{2+}$ ions exposed to an electric field within the ion activation region 206 established by a voltage differential between the electrically conductive ring members 202 and 204 of approximately 246 volts. FIGS. 20A-20C illustrate that as the electric field increases in the ion activation region 206, by increasing the voltage differential between the ring members 202 and 204, fragmentation of $[M+2H]^{2+}$ ions likewise increases. FIGS. 20D, 20E and 20F, in contrast, illustrate mass spectra 416, 418 and 420 respectively for $[M+3H]^{3+}$ ions exposed to an electric field within the ion activation region 206 established by a voltage differential between the electrically conductive ring members 202 and 204 of approximately 6.0 volts, approximately 106 volts and approximately 126 volts respectively. As with the $[M+2H]^{2+}$ ions, FIGS. 20D-20F illustrate that as the electric field increases in the ion activation region 206, by increasing the voltage differential between the ring members 202 and 204, fragmentation of $[M+3H]^{3+}$ ions likewise increases. For any specific set of conditions, fragmentation patterns have been found to be highly reproducible.

Figure 21:
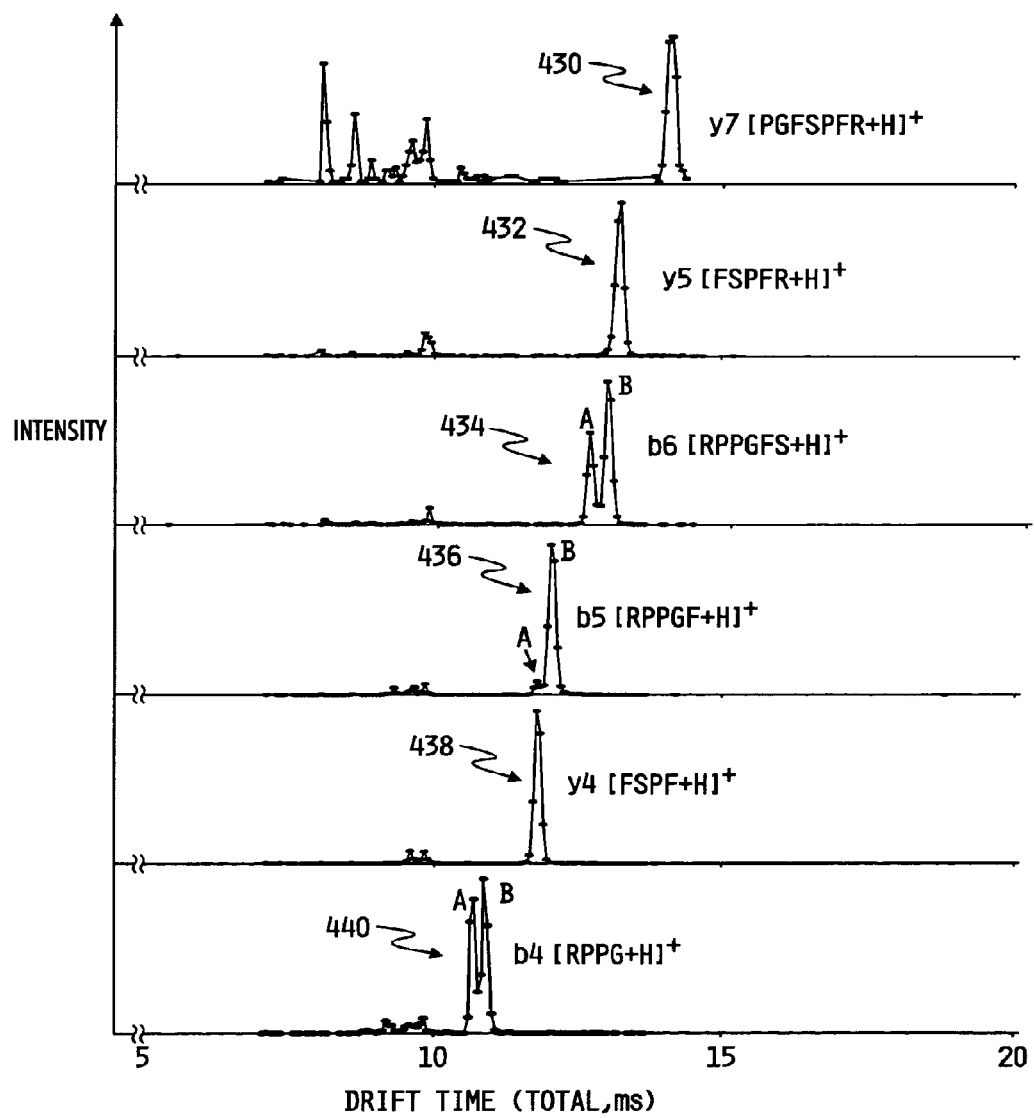
FIG. 21 includes a series of plots of drift time vs. intensity illustrating characteristic structures of ion fragment types produced from selected ions.

Information about mobilities and structures of fragment ions are of interest for a number of fundamental reasons, examples of which include, but should not be limited to, understanding dissociation mechanisms and applied uses, e.g., fragment ion mobilities provide additional constraints for assignment. By way of example, FIG. 21 shows ion mobility distributions for six different fragments of either y-type ions, e.g., mobility distributions 430, 432 and 438, or b-type ions, e.g., mobility distributions 434, 436 and 440. The distributions 430, 432 and 438 for y-type ions each show a single sharp peak, whereas the distributions 434, 436 and 440 for b-type ions each show evidence of two peaks. It can be concluded from FIG. 21 that b-type ion fragments must exist as at least two different conformations. It bears pointing out that, within experimental uncertainty, e.g., about ±10%, the ratio of the two peaks observed in b-type ion fragments appears to be the same, regardless of how the ion fragments are produced (i.e., the distributions appear to be similar at different IA2 activation voltages and the same distributions are obtained when fragmentation is initiated from [M+2H]$^{2+}$ precursors). This suggests that the structures and populations are not influenced by how the dissociation transition state is approached; rather the distribution appears to stabilize both populations after dissociation. It should also be noted that if the peak differences associated with b- and y-type ions (or other ions) are intrinsic to these fragments, the mobility dimension should provide for the ability to assign an m/z peak to a specific fragment type. The ability to distinguish a specific ion type from its mobility (or peak appearance) could greatly facilitate the use of fragmentation data for de novo sequencing.

It was described hereinabove that the third ion activation region, IA3, may be controlled to activate ions generally by disassociating (e.g., fragmenting) ions in the presence of a sufficiently high electric field or by inducing conformational changes in ions in the presence of an electric field that is high enough to induce such changes but not so high as to induce fragmentation. With respect to the example operational mode D, which was illustrated in FIG. 17D, it was described that IA3 may be used more specifically to activate fragments of ion mobility-selected ions that were fragmented in IA2 and that have been subsequently resolved (i.e., separated in time according to ion mobility) in D2. This process may be alternatively identified herein as the generation of secondary, e.g., 2°, fragments from mobility selected and resolved primary, e.g., 1°, ion fragments. A further example demonstrating the generation of such 2° fragment ions is shown in FIGS. 22A, 22B and 22C. FIG. 22A represents a drift time (ion mobility) vs. time-of-flight (ion mass-to-charge ratio) distribution 450 of 1° fragments generated from a distribution of ions that were mobility selected by pulsing G2 at time $t_0$. Secondary or 2° fragments generated from the 1° fragments are also shown in FIG. 22A. The 2° fragments of FIG. 22A along the vertical lines "a" and "b" are reproduced in FIGS. 22B and 22C respectively. It is possible to group the 2° fragments with the appropriate 1° fragment precursor because they have coincident D2 drift times. FIGS. 22B and 22C show example mass spectra for dissociation of the $b_6^{2+}$ and $y_7^{2+}$ 1° fragment precursors respectively. As discussed hereinabove with respect to IA2, fragmentation in the IA3 region is highly tunable and reproducible.

Figure 23:
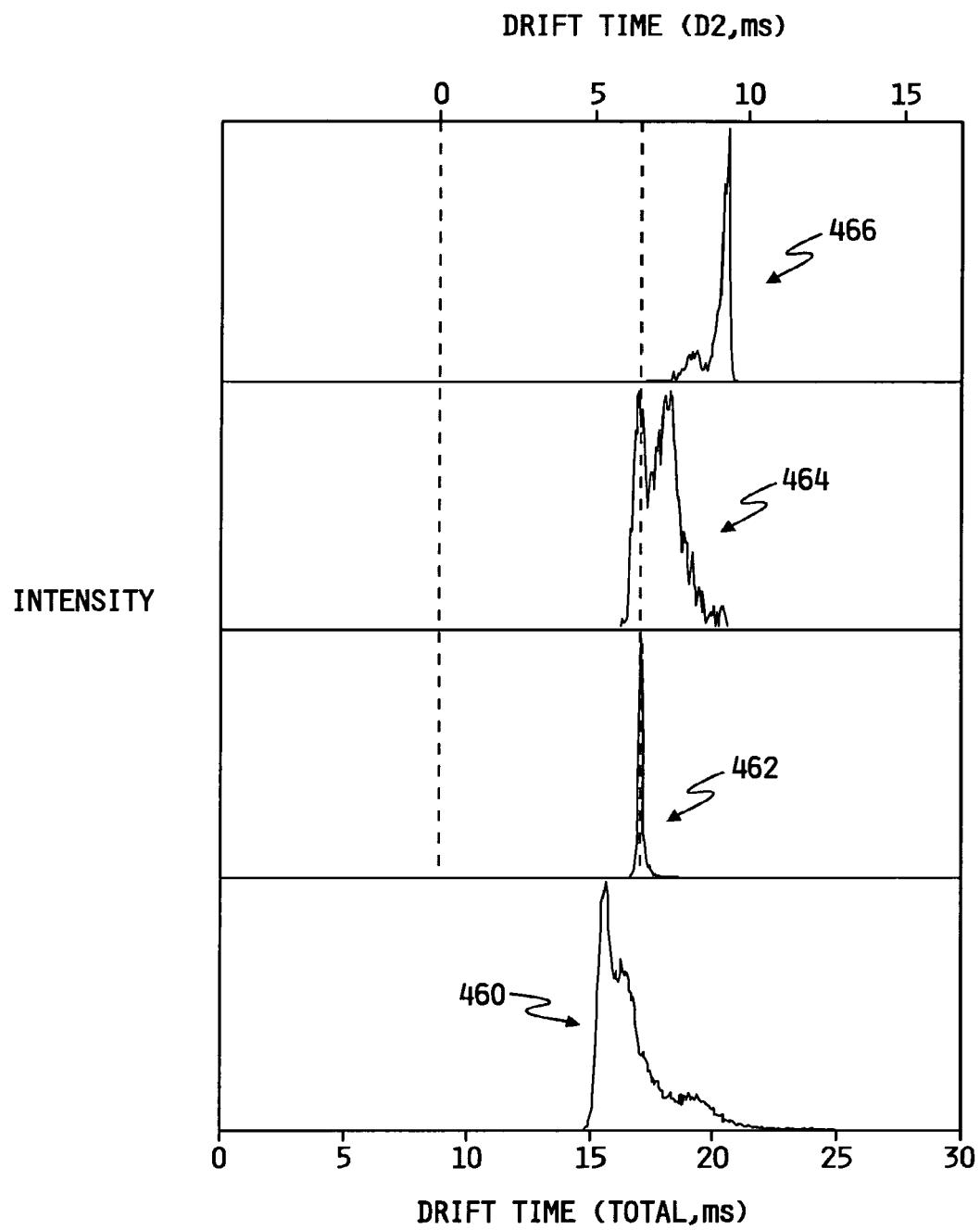
FIG. 23 includes a series of plots of drift time vs. intensity illustrating structural changes induced in a selected ion by exposure to various low-energy electric fields in the second ion activation region of the ion mobility spectrometer of FIG. 18.

Thus far, graphical examples of ion activation that have been provided herein have demonstrated ion disassociated or fragmentation capabilities of the ion activation regions IA2 and IA3. Another type of ion activation that may occur in any of the ion activation regions IA1-1A3 at lower electric fields than those used to disassociate ions was described hereinabove as induced ion structural or conformational changes. To demonstrate this type of analysis, FIG. 23 shows a total drift time (D1 and D2) distribution 460 of an [M+7H]$^{7+}$ protein ion, e.g., Ubiquitin, and a mobility-selected distribution 462 of the same protein ion with no activation in the IA2 region. With no ion activation in the IA2 region, the distribution 462 of the [M+7H]$^{7+}$ protein ion suggests that it typically exists in a compact conformation. With the IA2 region controlled to a low energy ion activation state, e.g., 70.7 volt differential between the electrically conductive rings 202 and 204, a structural change is observed, and the drift time distribution 464 indicates that the [M+7H]$^{7+}$ protein ion exists, under such conditions, in a partially folded state. In contrast, with the IA2 region controlled to another low energy ion activation state, e.g., 105.7 volt differential between the electrically conductive rings 202 and 204, another structural change is observed, and the drift time distribution 466 indicates that the [M+7H]$^{7+}$ protein ion exists, under these conditions, in an elongated state. FIG. 20 thus suggests that under the low-energy activation conditions employed, no fragmentation of the [M+7H]$^{7+}$ protein ion is observed, although different structural changes in the [M+7H]$^{7+}$ protein ion are clearly observed. At ~70 V activation, for example, the compact state 462 can be transformed into a new distribution of states 464. Some of these may be slightly more compact than the initial structure, but a majority of the states appear to occur in partially-folded states. Applying ~106 V to the IA2 region results in a distribution 466 that favors elongated structures.

A buffer gas, e.g., helium, is conventionally used to fill a chamber in which ion fragmentation is to be induced. However, limitations exist in obtaining sufficiently high electric fields in such ion fragmentation regions filled with conventional buffer gases because electrical breakdown of such electric fields typically occur at or below the desired field magnitudes. Consequently, the desired electric field magnitudes for ion fragmentation cannot be sustained in the presence of conventional buffer gases.

It was described hereinabove with respect to FIG. 1, and also throughout this document, that the IMS 10 and/or IMS 350 may be filled with a buffer gas or a gas mixture. By mixing a doping gas with a conventional buffer gas, and providing the mixture gas to an ion fragmentation region, a higher electric field can be sustained than could otherwise be sustained using the buffer gas alone. Thus, when the voltage source coupled to the ion fragmentation region IA1, IA2 or IA3 in the IMS 10 or 350 is controlled to establish an electric field in the ion fragmentation region IA1, IA2 or IA3 that is sufficiently high to fragment ions via collisions with the mixture of the buffer gas, e.g., Gas1, and the doping gas, e.g., Gas2, this field can be sustained without breaking down. Generally, the doping gas is selected such that the magnitude of the electric field that can be sustained in the ion fragmentation region, IA1, IA2 and/or IA3, without breaking down in the presence of the ions and the mixture of the buffer gas and the doping gas is higher than the magnitude of the electric field that can be sustained in the ion fragmentation region, IA1, IA2 and/or IA3, without breaking down in the presence of ions and only the buffer gas. With the ion analysis instruments illustrated and described herein, it has been found that a mixture gas, between approximately 1 mTorr-5 Torr, consisting of approximately 1-5 mole percent of the doping gas and 99-95 mole percent of the buffer gas allows a corresponding increase in the magnitude of the electric field established in the ion activation region, IA1, IA2 and/or IA3, without breaking down, by a factor of 2-3, thereby increasing the fragmentation efficiency of high mass-to-charge ratio ions. One example of a suitable buffer gas is Helium, and a suitable choice for a corresponding doping gas is Nitrogen, although other combinations of buffer and doping gases are contemplated.

It should now be apparent that the IMS 10 and 350 may be controlled to operate in any of a number of different modes via corresponding control of the various voltage sources. In perhaps the simplest case, which corresponds to Operational Mode A described hereinabove, ions are accumulated in the F1/IA1, and the gate, G1, is then controlled to release ions into the first drift tube region, D1, where they separate in time as a function of ion mobility. The gate, G2, is controlled to allow all ions to pass therethrough, so that the ions exiting D1 pass directly into the second drift tube region, D2, where they continue to separate in time as a function of ion mobility. In this mode, none of the ion activation regions IA1, IA2 and IA3 are active, so no ion activation occurs in any of these regions. In perhaps the most complicated case, in contrast, all three ion activation regions are active so that ion activation, e.g., either high-energy fragmentation or lower-energy induced structural changes, occurs in IA1, IA2 and in IA3, and the gate, G2, to the second drift tube region, D2, is controlled to selectively allow passage therethrough only of ions having a selected ion mobility or ion mobility range. In this mode, ions are accumulated and activated in F1/IA1, and the activated ions then pass into the first drift tube region, D1, when the gate, G1, is controlled to release the activated ions from F1/IA1. The activated ions separate in time as a function of ion mobility in the first drift tube region, D1, and the gate, G2, is controlled to allow passage therethrough only of ions having a selected ion mobility or ion mobility range. The mobility-selected, activated ions are then again activated in IA2, and the resulting twice-activated ions separate in time as a function of ion mobility in the second drift tube region, D2. The twice-activated and time-separated ions are then again activated in IA3 before exiting the IMS 10 or 350.

The various ion activation regions IA1, IA2 and IA3, along with the ion gates, G1 and G2, may be controlled in various combinations, and the electric fields induced in any active ion activation region IA1, IA2 and IA3 may be appropriately selected, to operate the IMS 10 or IMS 350 in intermediate modes between the two just described. As an example of one specific intermediate mode, the IMS 10 or 350 may be controlled to accumulate and fragment ions in F1/IA1. The gate, G1, may then be controlled to release the fragmented ions into the first drift tube region where they separate in time as a function of ion mobility. The gate, G2, is then controlled to allow passage therethrough only of an ion fragment or fragments having a selected ion mobility or ion mobility range. The second ion activation region, IA2, is controlled to fragment the mobility-selected ion fragment or fragments, which then separate as a function of ion mobility in the second drift tube, D2, before exiting the IMS 10 or 350.

It will be understood that while the ion mobility spectrometers 10 and 350 have been illustrated and described herein as being two-stage instruments, i.e., two drift tubes, D1 and D2, arranged in series, the present disclosure contemplates that additional drift tube sections may be added to form an N-stage ion mobility spectrometer, wherein N may be any positive integer. Moreover, any of the "N" stages may include any one or combination of an ion funnel structure, an ion gate and an ion activation region. The number of different operational modes that will be available with any such instrument will accordingly increase substantially with each stage added.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:
1. An ion mobility spectrometer comprising:
a source of purely buffer gas,
a drift tube defining a drift tube inlet configured to receive ions and a drift tube outlet, the drift tube receiving the buffer gas therein from the source of buffer gas,
a first ion gate separate from and positioned between the drift tube inlet and the drift tube outlet, the drift tube defining a first drift tube region between the drift tube inlet and the first ion gate, the first drift tube region responsive to a first set of voltage signals to separate ions in time as a function of ion mobility, the first ion gate responsive to a first ion gate control signal to impede passage of ions from the first drift tube region through the first ion gate and to a second ion gate control signal to allow passage of ions from the first drift tube region through the first ion gate,
a first set of voltage sources to produce the first set of voltage signals,
a first ion activation region positioned between the first ion gate and the drift tube outlet, the drift tube defining a second drift tube region between the first ion activation region and the drift tube outlet, the second drift tube region responsive to a second set of voltage signals to separate ions as a function of ion mobility, the first ion activation region responsive to a third set of voltage signals to selectively establish an electric field in the first ion activation region that induces structural changes in at least some of the ions that pass through the first ion gate by inducing changes in the shapes of at least some of the ions via collisions with the buffer gas without fragmenting the at least some of the ions,
a second set of voltage sources to produce the second set of voltage signals,
a third set of voltage sources to produce the third set of voltage signals, and
a processor electrically coupled to the first ion gate and producing the first and second ion gate control signals.

2. The ion mobility spectrometer of claim 1 further comprising:
a first ion funnel positioned between the drift tube inlet and the first ion activation region, the first ion funnel responsive to a fourth set of voltage signals to radially focus ions passing from the first drift tube region into the second drift tube region, the first ion gate coupled to the first ion funnel, and
a fourth set of voltage sources to produce the fourth set of voltage signals.

3. The ion mobility spectrometer of claim 2 wherein the first ion funnel defines an ion inlet and an ion outlet such that ions passing from the first drift tube region to the second drift tube region enter the ion inlet of the first ion funnel and exit the ion outlet of the first ion funnel,
and wherein the first ion gate is positioned at the ion inlet of the first ion funnel.

4. The ion mobility spectrometer of claim 3 wherein the first ion activation region is positioned adjacent to the ion outlet of the first ion funnel.

5. The ion mobility spectrometer of claim 2 further comprising:
a second ion funnel positioned in the second drift tube region adjacent to the drift tube outlet, the second ion funnel responsive to a fifth set of voltage signals to radially focus ions passing from the second drift tube region through the drift tube outlet, and
a fifth set of voltage sources to produce the fifth set of voltage signals.

6. The ion mobility spectrometer of claim 5 further comprising a second ion gate coupled to the second ion funnel, the second ion gate responsive to a third ion gate control signal to impede passage of ions through the second ion funnel and to a fourth ion gate control signal to allow passage of ions through the second ion funnel, wherein the processor is electrically coupled to the second ion gate and produces the third and fourth ion gate control signals.

7. The ion mobility spectrometer of claim 6 further comprising:
a second ion activation region positioned between the second ion funnel and the drift tube outlet, the second ion activation region responsive to a sixth set of voltage signals to selectively induce structural changes in at least some of the ions that pass through the second ion funnel, and
a sixth set of voltage sources to produce the sixth set of voltage signals.

8. The ion mobility spectrometer of claim 7 wherein the second ion activation region is responsive to the sixth set of voltage signals to selectively establish an electric field in the second ion activation region that induces structural changes in the at least some of the ions that pass through the second ion funnel by fragmenting the at least some of the ions via collisions with the buffer gas.

9. The ion mobility spectrometer of claim 7 wherein the second ion activation region is responsive to the sixth set of voltage signals to selectively establish an electric field in the second ion activation region that induces structural changes in the at least some of the ions that pass through the second ion funnel by inducing changes in the shapes of at least some of the ions via collisions with the buffer gas without fragmenting the at least some of the ions.

10. The ion mobility spectrometer of claim 7 further comprising an ion source region including:
an ion source to generate ions, and
a third ion funnel responsive to a seventh set of voltage signals to radially focus ions generated by the ion source and to direct the radially focused ions into the drift tube inlet, and
a seventh set of voltage sources to produce the seventh set of voltage signals.

11. The ion mobility spectrometer of claim 10 further comprising a third ion gate coupled to the third ion funnel, the third ion gate responsive to a fifth ion gate control signal to impede passage of ions through the third ion funnel and to a sixth ion gate control signal to allow passage of ions through the third ion funnel,
wherein the processor is electrically coupled to the third ion gate and produces the fifth and sixth ion gate control signals.

12. The ion mobility spectrometer of claim 11 further comprising:
a third ion activation region within the third ion funnel, the third ion activation region responsive to an eighth set of voltage signals to selectively induce structural changes in at least some of the ions that pass through the third ion funnel, and
an eighth set of voltage sources to produce the eighth set of voltage signals.

13. The ion mobility spectrometer of claim 12 wherein the third ion activation region is responsive to the eighth set of voltage signals to selectively establish an electric field in the third ion activation region that induces structural changes in the at least some of the ions that pass through the third ion funnel by fragmenting the at least some of the ions via collisions with the buffer gas.

14. The ion mobility spectrometer of claim 12 wherein the third ion activation region is responsive to the eighth set of voltage signals to selectively establish an electric field in the third ion activation region that induces structural changes in the at least some of the ions that pass through the third ion funnel by inducing changes in the shapes of at least some of the ions via collisions with the buffer gas without fragmenting the at least some of the ions.

15. The ion mobility spectrometer of claim 10 wherein the third ion funnel has one end defining a first opening with a first cross-sectional area and an opposite end defining a second opening with a second cross-sectional area smaller than the first cross-sectional area, the third ion funnel receiving generated ions via the first opening and supplying ions to the drift tube inlet via the second opening, the third ion funnel defining a cavity between the first and second openings responsive to the seventh set of voltage signals to radially focus ions between the first and second openings.

16. The ion mobility spectrometer of claim 1 further comprising an ion detector positioned to detect ions exiting the drift tube outlet and produce electrical signals indicative thereof.

17. The ion mobility spectrometer of claim 16 wherein the processor is electrically coupled to the ion detector and processes the electrical signals produced by the ion detector to determine corresponding ion mobility spectral information.

18. The ion mobility spectrometer of claim 1 further comprising an ion mass spectrometer positioned to receive ions exiting the drift tube outlet, the ion mass spectrometer configured to separate in time as a function of ion mass-to-charge ratio at least some of the ions exiting the drift tube outlet.

19. The ion mobility spectrometer of claim 18 further comprising an ion detector positioned to detect ions exiting the ion mass spectrometer and produce electrical signals indicative thereof.

20. The ion mobility spectrometer of claim 19 wherein the processor is electrically coupled to the ion detector and processes the electrical signals produced by the ion detector to determine ion spectral information as a function of ion mobility and of ion mass-to-charge ratio.

21. The ion mobility spectrometer of claim 10 wherein the ion source includes a protein solution,
and wherein the ion source generates protein ions from the protein solution.

22. An ion mobility spectrometer comprising: a drift tube defining a drift tube inlet configured to receive ions and a drift tube outlet, the drift tube defined by a plurality of joined electrically conductive rings and electrically insulating rings with adjacent ones of the electrically conductive rings separated by a different one of the electrically insulating rings, the plurality of electrically conductive rings and electrically insulating rings each defining an opening through which ions pass, the openings defined by the plurality of electrically conductive rings and the electrically insulating rings being aligned to form [a continuous cavity, without a flow restriction orifice, defining] an ion drift path from the drift tube inlet to the drift tube outlet,
a first ion funnel formed by a first subset of the electrically conductive rings and electrically insulating rings that define the drift tube, the first subset including a first electrically conductive ring that defines an ion inlet of the first ion funnel and a last electrically conductive ring that defines an ion outlet of the first ion funnel, the first ion funnel separate from and positioned between the drift tube inlet and the drift tube outlet, the first ion funnel responsive to a first set of voltage signals to radially focus ions passing therethrough,
a first set of voltage sources to produce the first set of voltage signals,
a first ion gate formed on one of the plurality of electrically conductive rings that define the first ion funnel, the first ion gate responsive to a first ion gate control signal to impede passage of ions through the first ion funnel and to a second ion gate control signal to allow passage of ions through the first ion funnel, and a first ion activation region defined between the last electrically conductive ring of the first ion funnel and a next adjacent one of the electrically conductive rings of the drift tube, the first ion activation region responsive to a second set of voltage signals to selectively induce structural changes in at least some of the ions that pass through the first ion gate without fragmenting the at least some of the ions, a second set of voltage sources to produce the second set of voltage signals, and a processor electrically coupled to the first ion gate and producing the first and second ion gate control signals.

23. The ion mobility spectrometer of claim 22 further comprising:

a second ion funnel formed by a second subset of the electrically conductive rings and electrically insulating rings that define the drift tube, the second subset including a first electrically conductive ring that defines an ion inlet of the second ion funnel and a last electrically conductive ring that defines an ion outlet of the second ion funnel, the second ion funnel separate from the first ion funnel and positioned with the ion outlet of the second ion funnel adjacent to the drift tube outlet, the second ion funnel responsive to a third set of voltage signals to radially focus ions passing therethrough, a third set of voltage sources to produce the third set of voltage signals, a second ion gate formed on one of the plurality of electrically conductive rings that define the second ion funnel, the second ion gate responsive to a third ion gate control signal to impede passage of ions through the second ion funnel and to a fourth ion gate control signal to allow passage of ions through the second ion funnel, and a second ion activation region defined between the last electrically conductive ring of the second ion funnel and a next adjacent one of the electrically conductive rings of the drift tube, the second ion activation region responsive to a fourth set of voltage signals to selectively induce structural changes in at least some of the ions that pass through the second ion gate, and a fourth set of voltage sources to produce the fourth set of voltage signals, wherein the processor produces the third and fourth ion gate control signals.

24. The ion mobility spectrometer of claim 22 further comprising an ion source region including:

an ion source to generate ions, a second ion funnel responsive to a third set of voltage signals to radially focus ions generated by the ion source and to direct the radially focused ions into the drift tube inlet, and a third set of voltage sources to produce the third set of voltage signals.

25. The ion mobility spectrometer of claim 24 further comprising a second ion gate coupled to the second ion funnel, the second ion gate responsive to a third ion gate control signal to impede passage of ions through the second ion funnel and to a fourth ion gate control signal to allow passage of ions through the second ion funnel, wherein the processor produces the third and fourth ion gate control signals.

26. The ion mobility spectrometer of claim 25 further comprising a second ion activation region within the second ion funnel, the second ion activation region responsive to a fourth set of voltage signals to selectively induce structural changes in at least some of the ions that pass through the second ion funnel, and a fourth set of voltage sources to produce the fourth set of voltage signals.

* * * * *